(12) United States Patent
Doddrell et al.

(10) Patent No.: US 7,088,099 B2
(45) Date of Patent: Aug. 8, 2006

(54) CORRECTION OF MAGNETIC RESONANCE IMAGES

(75) Inventors: David M. Doddrell, Brisbane (AU); Huawei Zhao, Brisbane (AU)

(73) Assignee: The University of Queensland, Brisbane (AU)

( * ) Notice: Subject to any disclaimer, the term of this patent is extended or adjusted under 35 U.S.C. 154(b) by 318 days.

(21) Appl. No.: 10/744,593

(22) Filed: Dec. 23, 2003

(65) Prior Publication Data

US 2005/0024051 A1 Feb. 3, 2005

Related U.S. Application Data

(63) Continuation of application No. PCT/AU03/001707, filed on Dec. 22, 2003.

(51) Int. Cl.
*G01V 3/00* (2006.01)

(52) U.S. Cl. ..................... 324/309; 324/307
(58) Field of Classification Search ............ 324/309, 324/307, 318, 300; 600/410; 428/172
See application file for complete search history.

(56) References Cited

U.S. PATENT DOCUMENTS

| | | | | |
|---|---|---|---|---|
| 5,260,116 A | * | 11/1993 | Hamanaka et al. | 428/172 |
| 5,289,127 A | * | 2/1994 | Doddrell et al. | 324/314 |
| 6,252,401 B1 | | 6/2001 | Werthner et al. | 324/309 |
| 6,501,273 B1 | | 12/2002 | Krieg et al. | 324/309 |
| 6,636,756 B1 | | 10/2003 | Zhu | 600/410 |
| 2002/0093334 A1 | | 7/2002 | Zhu | |

OTHER PUBLICATIONS

Bakker CJ, Moerland MA, Bhagwandien R, Beersma R. "Analysis of machine–dependent and object–induced geometric distortion in 2DFT MR imaging." *Magn Reson Imaging*. 1992;10(4):597–608.

Chang H, Fitzpatrick JM. "A technique for accurate magnetic resonance imaging in the presence of field inhomogeneities." *IEEE Trans. Med. Imaging*, 11: 319–329, 1992.

Chen NK, Wyrwicz AM. "Optimized distortion corretcion technique for echo planar imaging." *Magn Reson Med*. Mar. 2001;45(3):525–8.

(Continued)

*Primary Examiner*—Brij B Shrivastav
(74) *Attorney, Agent, or Firm*—Maurice M. Klee

(57) ABSTRACT

Spatial encoding in magnetic resonance imaging (MRI) techniques is achieved by sampling the signal as a function of time in the presence of magnetic field gradients, e.g., X, Y, and Z gradients. The gradient magnets have in the past been assumed to generate a linear gradient, and typical image reconstruction techniques have relied upon this assumption. However, to achieve high speed performance, gradient magnets often sacrifice linearity for speed. This non-linearity, in turn, results in distorted images, the distortion often being sufficiently large to compromise the usefulness of MRI images for stereotaxy or longitudinal studies, where precise volumetric information is required. The disclosure provides practical methods for correcting distorted images resulting from such non-linearity in the gradient fields, as well as distortions resulting from translational, rotational, and/or winding/design errors in the field generating devices. The methods employ spherical harmonic expansions of the gradient fields and fast Fourier transform techniques to provide well-corrected images without undue computational burdens.

135 Claims, 16 Drawing Sheets

OTHER PUBLICATIONS

Collins DL, Evans AC. "Animal: validation and applications of non–linear registration–based segmentation." *Int J Pattern Recog and Art Intell*, 1997: 11:1271–1293.

Cusack R, Brett M, Osswald K. "An evaluation of the use of magnetic field maps to undistort echo–planar images." *Neuroimage*. Jan. 2003;18(1):127–42.

Eccles CD, Crozier S, Westphal M, Doddrell DM. "Temporal spherical–harmonic expansion and compensation of eddy–current fields produced by gradient pulses." *Journal of Magnetic Resonance*, A 103: 135–141, 1993.

Fransson A, Andreo P, Potter R. "Aspects of MR image distortions in radiotherapy treatment planning." *Strahlenther Onkol*. Feb. 2001;177(2):59–73.

Langlois S, Desvignes M, Constans JM, Revenu M. "MRI geometric distortion: a simple approach to correcting the effects of non–linear gradient fields." *J Magn Reson Imaging*. Jun. 1999;9(6):821–31.

Liu H, "An efficient geometric image distortion correction method for a biplanar planar gradient coil." *Magnetic Resonance Materials in Physics, Biology and Medicine*, 10: 75–79, 2000.

Maurer CR Jr, Aboutanos GB, Dawant BM, Gadamsetty S, Margolin RA, Maciunas RJ, Fitzpatrick JM. "Effect of geometrical distortion correction in MR on image registration accuracy." *J Comput Assist Tomogr*. Jul.–Aug. 1996;20(4):666–79.

Mizowaki T, Nagata Y, Okajima K, Murata R, Yamamoto M, Kokubo M, Hiraoka M, Abe M. "Development of an MR simulator: experimental verification of geometric distortion and clinical application." *Radiology*. Jun. 1996;199(3):855–60.

Mizowaki T, Nagata Y, Okajima K, Kokubo M, Negoro Y, Araki N, Hiraoka M. "Reproducibility of geometric distortion in magnetic resonance imaging based on phantom studies." *Radiother Oncol*. Nov. 2000;57(2):237–42.

Moerland MA, Beersma R, Bhagwandien R, Wijrdeman HK, Bakker CJ. "Analysis and correction of geometric distortions in 1.5 T magnetic resonance images for use in radiotherapy treatment planning." *Phys Med Biol*. Oct. 1995;40(10):1651–1664.

Schad L, Lott S, Schmitt F, Sturm V, Lorenz WJ. "Correction of spatial distortion in MR imaging: a prerequisite for accurate stereotaxy." *J Comput Assist Tomogr*. May–Jun. 1987;11(3):499–505.

Schad LR, Ehricke HH, Wowra B, Layer G, Engenhart R, Kauczor HU, Zabel HJ, Brix G, Lorenz WJ. "Correction of spatial distortion in magnetic resonance angiography for radiosurgical treatment planning of cerebral arteriovenous malformations." *Magn Reson Imaging*. 1992;10(4):609–21.

Tanner SF, Finnigan DJ, Khoo VS, Mayles P, Dearnaley DP, Leach MO. "Radiotherapy planning of the pelvis using distortion corrected MR images: the removal of system distortions." *Phys Med Biol*. Aug. 2000;45(8):2117–32.

Woo JH, Kim YS, Kim SI. "The correction of MR images distortion with phantom studies." *Stud Health Technol Inform*. 1999;62:388–9.

Yu C, Petrovich Z, Apuzzo ML, Luxton G. "An image fusion study of the geometric accuracy of magnetic resonance imaging with the Leksell stereotactic localization system." *J Appl Clin Med Phys*. 2001 Winter;2(1):42–50.

* cited by examiner (a)         (b)

CORRECTION OF MAGNETIC RESONANCE IMAGES

I. FIELD OF THE INVENTION

This invention relates to magnetic resonance imaging (MRI). In particular, the invention is directed to the use of spherical harmonic deconvolution methods to compensate for the effects on MRI images of (i) non-linear gradients (hereinafter referred to as the "non-linear problem"), (ii) misalignments of the symmetry points of one or more of the MR system's field generating devices, i.e., the main ($B_0$) magnet, the X-gradient magnet, the Y-gradient magnet, and the Z-gradient magnet (hereinafter referred to as the "non-coincident center problem"), (iii) deviations from ideal geometric alignment of the field generating devices (hereinafter referred to as the "axes misalignment problem"), and (iv) winding and/or design errors of the field generating devices (hereinafter referred to as the "winding error problem").

II. BACKGROUND OF THE INVENTION

The quality of images in magnetic resonance imaging is dependent upon the homogeneity of the respective instrumental components used to generate the image. Much attention has been given to the design and development of magnets having the necessary homogeneity over the imaging volume. Variations in magnetic field homogeneity manifest themselves as image distortions and intensity variation from the true values. Radio frequency (rf) coil inhomogeneity results in non-uniform excitation of the nuclear spins resulting in intensity variations, while deviation from linearity of the gradient field from application of the pulsed field gradients induces image translation and distortions.

More specifically, the quality of a magnetic resonance image is dependent upon the accuracy by which physical position is spatially encoded. As MRI data is now used routinely for stereotaxy, longitudinal studies of atrophy and functional studies, ensuring images have no distortion and inhomogeneity is critical. The principal machine dependant sources of this inhomogeneity previously recognized in the art are eddy currents, gradient non-linearity, $B_0$ and $B_1$ inhomogeneity. See Tanner S F, Finnigan D J, Khoo V S, Mayles P, Dearnaley D P, Leach M O. Radiotherapy planning of the pelvis using distortion corrected MR images: the removal of system distortions. Phys Med Biol. 2000 August; 45(8):2117–32.

As discussed in detail below, the present invention in accordance with certain of its aspects is directed to an analytical approach for calculating and removing the effects of non-linear gradients. Non-linear gradients have been addressed because of the recent interest in short-bore high-speed gradients.

In particular, there has been recent significant interest in the development of gradients having rise times less than 200 μseconds. Although peripheral nerve stimulation is a limiting feature of short rise times, such gradients have found use in high-speed echo planar imaging (EPI) of the heart and diffusion tensor imaging of the brain. To achieve short rise times and to avoid peripheral nerve stimulation, gradient designers have restricted the length of the gradients and limited the number of turns. These limitations, although suitable for the implementation of pulse sequences having the desired speed, have the undesired consequence of increased non-linearity in the gradient fields. The result is distorted images.

More particularly, non-linear pulsed field gradients induce image distortions due to incorrect spatial encoding of the signal. If we assume field gradients are linear, it follows that k-space is sampled linearly and thus a fast Fourier transform (FFT) is suitable for reconstruction. However, any deviation from linearity in the gradients results in non-linear data sampling and subsequent errors in image spatial encoding. A non-linear Fourier transformation would allow this data to be correctly transformed to an image. Unfortunately, non-linear Fourier transformation greatly increases computation time by $N/\log_2 N$, relative to a FFT, making real-time image generation computationally prohibitive.

As discussed fully below, the present invention in accordance with certain of its aspects addresses this problem and provides a general analytical solution to correct image distortions induced by gradient non-linearity which: (1) is applicable to any gradient configuration, (2) is robust, and (3) importantly, maintains the FFT as the method for image reconstruction.

Mapping and correcting of MRI distortions has been previously considered in the art and attempts have been made to correct the image distortion induced by the non-linearity of the gradients produced by the gradient coils. Two early papers by Schad et al discuss "pincushion" effects seen with 2D phantoms. See Schad L, Lott S, Schmitt F, Sturm V, Lorenz W J. Correction of spatial distortion in MR imaging: a prerequisite for accurate stereotaxy. J Comput Assist Tomogr. 1987 May–June; 11(3):499–505; and Schad L R, Ehricke H H, Wowra B, Layer G, Engenhart R, Kauczor H U, Zabel H J, Brix G, Lorenz W J. Correction of spatial distortion in magnetic resonance angiography for radiosurgical treatment planning of cerebral arteriovenous malformations. Magn Reson Imaging. 1992; 10(4):609–21.

Subsequent schemes include:

(1) using a stereotaxic frame as a reference marker (see Maurer C R Jr, Aboutanos G B, Dawant B M, Gadamsetty S, Margolin R A, Maciunas R J, Fitzpatrick J M. Effect of geometrical distortion correction in MR on image registration accuracy. J Comput Assist Tomogr. 1996 July–August; 20(4):666–79; and Moerland M A, Beersma R, Bhagwandien R, Wijrdeman H K, Bakker C J. Analysis and correction of geometric distortions in 1.5 T magnetic resonance images for use in radiotherapy treatment planning. Phys Med Biol. 1995 October; 40(10):1651–4);

(2) comparing phantom images from CT and MRI (see Fransson A, Andreo P, Potter R. Aspects of MR image distortions in radiotherapy treatment planning. Strahlenther Onkol. 2001 February; 177(2):59–73; and Yu C, Petrovich Z, Apuzzo M L, Luxton G. An image fusion study of the geometric accuracy of magnetic resonance imaging with the Leksell stereotactic localization system. J Appl Clin Med Phys. 2001 Winter; 2(1):42–50); and (3) imaging specific MRI phantoms that typically consist of an array of tubes filled with a suitable contrast agent (see Bakker C J, Moerland M A, Bhagwandien R, Beersma R. Analysis of machine-dependent and object-induced geometric distortion in 2DFT MR imaging. Magn Reson Imaging. 1992; 10(4):597–608; Mizowaki T, Nagata Y, Okajima K, Murata R, Yamamoto M, Kokubo M, Hiraoka M, Abe M. Development of an MR simulator: experimental verification of geometric distortion and clinical application. Radiology. 1996 June; 199(3):855–60; Woo J H, Kim Y S, Kim S I. The correction of MR images distortion with phantom studies. Stud Health Technol Inform. 1999; 62:388–9.; and Tanner et al., supra).

A later Mizowaki et al paper (Mizowaki T, Nagata Y, Okajima K, Kokubo M, Negoro Y, Araki N, Hiraoka M. Reproducibility of geometric distortion in magnetic resonance imaging based on phantom studies. Radiother Oncol. 2000 November; 57(2):237–42) alludes to an important problem with phantom studies; after assessing the reproducibility of their own phantom based correction, the authors conclude that such correction may be only applicable in limited situations.

Field mapping is another approach to determining distortion via induced phase shift (see Chang H, Fitzpatrick J M. A technique for accurate magnetic resonance imaging in the presence of field inhomogeneities. IEEE Trans. Med. Imaging, 11: 319–329, 1992; Chen N K, Wyrwicz A M. Optimized distortion correction technique for echo planar imaging. Magn Reson Med. 2001 March; 45(3):525–8; and Cusack R, Brett M, Osswald K. An evaluation of the use of magnetic field maps to undistort echo-planar images. Neuroimage. 2003 January; 18(1):127–42). In particular, the Chang et al. approach relies on the acquisition of two images using different gradient strengths. From the induced phase shift across the difference image a distortion map of the gradient field can be calculated and the images corrected. Other correction schemes have been proposed for particular problems including a post-processing method for correcting distortions induced when using bi-planar gradients (see Liu H, An efficient geometric image distortion correction method for a biplanar planar gradient coil. Magnetic Resonance Materials in Physics, Biology and Medicine, 10: 75–79, 2000). Regardless, these approaches are of limited use in attempting to discern, model or correct distortion due to part of the MRI system in isolation, specifically, the gradients.

In a recent paper (see Langlois S, Desvignes M, Constans J M, Revenu M. MRI geometric distortion: a simple approach to correcting the effects of non-linear gradient fields. J Magn Reson Imaging. 1999 June; 9(6):821–31), a method has been suggested for the correction of both the intensity variations and geometric distortions induced by non-linear gradients based on treating gradient coils as either an opposed Helmoltz pair for the Z-gradient and a Golay arrangement for the transverse gradients. However, this approach treats the non-linear component of the gradient field as a constant for the intensity correction and demonstrates correction of the non-linear induced distortion by correcting a large phantom (a cube of approximately 20 cm length). It is also assumed that for the chosen gradient geometry only second order terms are important. Whilst this approach is useful for gradients with a significant length to diameter ratio (>2), it is of limited use with current high-speed gradients with significant higher order gradient field impurities.

In a recent patent (see Krieg R, Schreck O. U.S. Pat. No. 6,501,273, issued Dec. 31, 2002), it has been suggested that spherical harmonics may be useful in developing a general robust method, but none is given. Another patent application (see Zhu Y, U.S. Patent Application Publication No. US 2002/0093334, dated Jul. 18, 2002) has suggested a method to reconstruct k-space based upon an assumed non-linearity. The method proposed involves approximately $10^{14}$ triple integrations and thus is of limited practical value. Indeed, this patent publication highlights one of the primary deficiencies in the art—namely, the failure to realize that any method, which is of practical value, must use the FFT as its basis.

From the foregoing, it can be seen that there exists an established need in the art for a general method for correcting image distortions due to gradient non-linearity. In particular, a need exists for a method that is based on a rigorous approach to the problem allowing clinicians confidence in their image interpretation.

This invention in accordance with certain of its aspects provides such a general method to correct image distortions induced by gradient non-linearity. Significantly, the method is applicable to any gradient configuration.

In addition to the problem of non-linearity, in the course of developing the analytical techniques described below, it was discovered that the field generating devices of a typical MRI system can have (i) substantially displaced symmetry points, i.e., the symmetry points do not share a common center (the non-coincident center problem), and (ii) substantial deviations from ideal geometric alignment, i.e., the individual Cartesian coordinate systems associated with the individual field generating devices, in addition to having displaced centers, can also be rotated relative to each other and/or relative to the overall Cartesian coordinate system of the MRI system (the axes misalignment problem). Such translational and rotational misalignments in and of themselves produce distortions in MR images. Winding and/or design errors for the field generating devices are another source of distortion (the winding error problem). In accordance with others of its aspects, the present invention also addresses the problems associated with these sources of distortion.

III. SUMMARY OF THE INVENTION

This invention provides methods for correcting distortions of MR images due to gradient non-linearities in a nuclear magnetic resonance (NMR) tomography apparatus and/or distortions due to translational and/or rotational misalignments of the field generating devices of such apparatus and/or distortions due to errors in the winding and/or design of the field generating devices. The apparatus typically comprises a magnet (with shim coils as required) for generating a substantially constant main ($B_0$) magnetic field in a volume of interest, as well as gradient coils for generating gradient magnetic fields, as is known in the art. The method comprises the initial step of deconvolving the main magnetic field. Preferably, the magnetic field is deconvolved using a bases set of spherical harmonics, but other suitable bases sets can be used. The deconvolution is performed using an origin defined by the MRI apparatus, e.g., the center of the image region.

The gradient coils are then preferably excited individually, i.e., one at a time, using a constant current. Typically, a low current is applied in order not to burn out the coils. For each constantly excited gradient coil, the magnetic field is deconvolved again preferably using the same origin. As the gradient field is intended to be linear, for a perfect gradient magnet having its symmetry point and axes coincident with the origin and its associated axes, a single harmonic coefficient should result from the deconvolution, e.g., the a(1,1) coefficient for the X-gradient magnet, the b(1,1) coefficient for the Y-gradient magnet, and the a(1,0) coefficient for the Z-gradient magnet (hereinafter referred to as the "primary coefficients"). The harmonics of the main magnet (optionally shimmed as necessary) obtained from the first deconvolution are then subtracted, in order to obtain the effect of just the gradient and its impurities and/or alignment errors. The result is a set of spherical harmonic coefficients for the gradient coil, i.e., the "a" and "b" coefficients for the coil discussed below and referred to in the claims. The presence of coefficients with substantial values other than the primary coefficients is indicative of non-linearities in the gradient magnets and/or non-coincident symmetry points, and/or rotated axes, and/or winding or design errors.

Although it is preferred to obtain spherical harmonic coefficients for each gradient coil separately, in some cases, the symmetry of the system will permit the use of spherical harmonic coefficients obtained for one of the gradient coils for another coil. For example, for $B_0$ directed along the z-axis of an x,y,z-coordinate system and for x-gradient, y-gradient, and z-gradient coils having symmetry points at the same or effectively the same location as (i) the main ($B_0$) coil (after any shimming), (ii) one another, and (iii) the center of the image region, and for well-aligned axes for the field generating devices and low levels of winding/design errors, measurements may only be needed for the z-gradient coil and one of the x and y coils, with the spherical harmonic coefficients for the measured x or y coil being used for the non-measured coil. Similarly, it is most preferred to obtain spherical harmonic coefficients for each individual MRI machine as installed and shimmed. However, generic coefficients obtained for a representative sample of a particular series or model of MRI machine may be used if desired. Along these same lines, theoretical coefficients, as opposed to measured coefficients, can be used, but are not preferred.

As a general rule, the more measurements made, e.g., measurements for each of the x, y, and z gradient coils, and the more the measurements are for a specific machine, e.g., for an individual machine after installation and shimming, the better the correction of gradient-based distortion. However, notwithstanding this general rule, the invention will still be of benefit even if the sets of spherical harmonic coefficients used are not the optimum coefficients. In the end, all that is required to apply the corrective techniques of the invention is a set of spherical harmonic coefficients, however obtained, for each of the gradient magnets used to produce the MRI image which is to be corrected. In practice, these sets will be stored in a look-up table, e.g., on the hard drive of a computer system, for use in performing the corrective methods of the invention.

In its typical embodiment, the invention comprises acquiring time domain data using gradients which exhibit one or more of the non-linear, non-coincident center, axes misalignment, or winding error problems and then transforming the uncorrected time domain data using a fast Fourier transformation to provide a distorted image in image space. As the origin or cause of the distortion is known (namely, the non-primary harmonics calculated above), they are then used to correct the image space image.

More particularly, in accordance with a first aspect (see generally, the left column of FIG. 8), the invention provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function $\rho(x,y,z)$ from the MR data set by a process which comprises performing a three dimensional fast Fourier transform on said data set; and (C) producing a corrected image function $\rho(x',y',z')$ from the uncorrected image function $\rho(x,y,z)$, where the coordinates $(x',y',z')$ represent a corrected position in the x,y,z-coordinate system for the value of the image function at $(x,y,z)$, said $(x',y',z')$ coordinates being determined using an iterative mapping which employs coefficients of spherical harmonic expansions for the magnetic fields produced by the X, Y, and Z gradient magnets (the "spherical harmonic coefficients").

Preferably, the iterative mapping is of the form of equation (21) below and employs a "quitting" parameter of the type set forth in equation (22). A suitable value for the quitting parameter is, for example, $10^{-3}$, which is sufficiently small to provide a correct image appearance. Generally, the smaller the quitting parameter, the longer the correction takes to perform. For example, about 3 iterations are needed to achieve the $10^{-3}$ criterion with a computation time of about 2 seconds. Increasing the computation time to, for example, 2.5 seconds would easily achieve a lower value, e.g., $10^{-4}$. In general, between two and four iterations are preferred as a reasonable compromise between computation time and satisfactory image correction. Other quitting parameters and iteration numbers can, of course, be used in the practice of this aspect of the invention or other aspects which involve iterations and/or quitting parameters.

In accordance with a second aspect (see generally, the middle column of FIG. 8), the invention provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function $\rho(x,y,z)$ from the MR data set by a process which comprises performing a three dimensional fast Fourier transform on said data set; and (C) producing a corrected image function $\rho(x',y',z')$ from the uncorrected image function $\rho(x,y,z)$, where the coordinates $(x',y',z')$ represent a corrected position in the x,y,z-coordinate system for the value of the image function at $(x,y,z)$, said $(x',y',z')$ coordinates being determined by solving a system of non-linear equations so that an error function $f(x',y',z')$ satisfies the relationship:

$$\|f(x',y',z')\| \leq \epsilon,$$

where $\epsilon$ is a predetermined constant;

wherein the system of non-linear equations employs coefficients of spherical harmonic expansions for the magnetic fields produced by the X, Y, and Z gradient magnets (the "spherical harmonic coefficients").

Preferably, the system of non-linear equations is solved iteratively (e.g., using a Levenberg-Marquardt non-linear curve fitting technique or a non-linear minimization technique) using ($x_0'=x$, $y_0'=y$, $z_0'=z$) as the initial ($x',y',z'$)

values and an error function and system of non-linear equations of the form:

$$f(x', y', z') = \begin{cases} f_X(x', y', z') = B_X^{LN}(r', \theta', \phi') - xG_X^L \cong 0 \\ f_Y(x', y', z') = B_Y^{LN}(r', \theta', \phi') - yG_Y^L \cong 0 \\ f_Z(x', y', z') = B_Z^{LN}(r', \theta', \phi') - zG_Z^L \cong 0 \end{cases}$$

where:
(a) (x', y', z') values and (r', θ', φ') values are related by:

$$\begin{cases} r' = \sqrt{x'^2 + y'^2 + z'^2} \\ \theta' = \tan^{-1}\left(\frac{\sqrt{x'^2 + y'^2}}{z'}\right) \\ \phi' = \tan^{-1}\left(\frac{y'}{x'}\right) \end{cases}$$

(b) the $a_{V(n,m)}$ and $b_{V(n,m)}$ used in the expression for $B_{V(n,m)}(r',\theta',\phi')$ (see below) are the spherical harmonic coefficients, where the subscript V is one of X, Y, and Z;

(c) ($G_X^L = a_{X(1,1)}$, $G_Y^L = b_{Y(1,1)}$, $G_Z^L = a_{Z(1,0)}$) represent the linear parts of the gradients ($G_X$, $G_Y$, $G_Z$) of the magnetic fields produced by the X, Y, and Z gradient magnets, respectively; and $$\begin{cases} B_X^{LN}(r', \theta', \phi') = \sum_{n=0}^{\infty} \sum_{m} B_{X(n,m)}(r', \theta', \phi') \\ B_Y^{LN}(r', \theta', \phi') = \sum_{n=0}^{\infty} \sum_{m} B_{Y(n,m)}(r', \theta', \phi') \\ B_Z^{LN}(r', \theta', \phi') = \sum_{n=0}^{\infty} \sum_{m} B_{Z(n,m)}(r', \theta', \phi') \end{cases}$$

represent the linear and non-linear parts of the magnetic fields produced by the X, Y, and Z gradient magnets, where:
(i) m and n are the indices of the summations and satisfy the relationship m≦n; and
(ii) $B_{V(n,m)}(r',\theta',\phi')$ is given by:

$$B_{V(n,m)}(r',\theta',\phi') = r'^n [a_{V(n,m)}\cos(m\phi') + b_{V(n,m)}\sin(m\phi')]P_{(n,m)}(\cos\theta')$$

where the $P_{(n,m)}(\cos\theta')$ are associated Legendre functions and the subscript V is one of X, Y, and Z.

It should be noted that if each of the gradient magnets and the main ($B_0$) magnet (after any shimming) are effectively free of the non-coincident center problem, the axes misalignment problem, and the winding error problem (hereinafter referred to as the "base case"), then the summation in subparagraph (d) can begin with n=1 rather than n=0 if desired, since the lower order terms will be equal to, or effectively equal to, zero, i.e., their magnitudes will be zero or numerically small relative to other terms.

In these preferred embodiments, E preferably satisfies the relationship:

$$\epsilon = R_{es} \times 10^{-3}$$

where $R_{es}$ is the resolution of the image given by:

$$R_{es} = A_{image}/N_{pix},$$

where $A_{image}$ is the area of the image (e.g., a two-dimensional image on a display screen) and $N_{pix}$ is total number of pixels making up the image.

As with the first aspect of the invention, larger or smaller values of ε can be used in the practice of the invention, with larger values leading to reduced computation time and smaller values to increased time.

In accordance with the foregoing first and second aspects of the invention, the data space preferably comprises one of:
(a) k-space;
(b) time space;
(c) phase space;
(d) frequency space;
(e) time space along at least one coordinate direction and phase space along at least one other coordinate direction; or
(f) time space along at least one coordinate direction and frequency space along at least one other coordinate direction.

The first and second aspects of the invention have been described above in terms of correcting 3D imaging where the imaging coordinate system corresponds to the x,y,z-coordinate system. These aspects of the invention can also be used In the case of arbitrary 3D imaging, i.e., 3D imaging where the imaging coordinates are oriented in an arbitrary way with respect to the x,y,z-coordinate system. Such arbitrary 3D imaging can be of benefit in, for example, avoiding artifacts in brain images, specifically, in avoiding artifacts associated with the presence of air in nasal structures. The arbitrary 3D imaging is achieved in practice by selecting values for the X, Y, and Z gradient magnets which cause the imaging volume to have associated therewith a Cartesian coordinate system which is rotated relative to the x,y,z-coordinate system.

The relevant geometry is shown in FIG. 1A, where ($\zeta_1,\zeta_2,\zeta_3$) represent the arbitrary coordinates, with $\zeta_1$ and $\zeta_2$ being perpendicular to one another and intersecting at O, and $\zeta_3$ being an axis that passes through O and is perpendicular to the plane defined by $\zeta_1$ and $\zeta_2$. In this figure, θ(0≦θ≦π) is the angle between O$\zeta_3$ and OZ, ψ (0≦ψ<2π) is the angle between OA and OX, and φ (0≦φ<2π) is the angle between OA and O$\zeta_1$, where OA is the intersection of the plane O$\zeta_1\zeta_2$ and the plane OXY.

The coordinate transformation between the x,y,z-coordinate system and the ($\zeta_1,\zeta_2,\zeta_3$) coordinate system can be written as:

$$r = A\zeta \text{ and } \zeta = A^{-1}r$$

where $$r = [x, y, z]^T,$$

$$\zeta = [\zeta_1, \zeta_2, \zeta_3]^T,$$

$$A = \begin{bmatrix} c_{11} & c_{12} & c_{13} \\ c_{21} & c_{22} & c_{23} \\ c_{31} & c_{32} & c_{33} \end{bmatrix},$$

and $c_{11} = \cos\psi\cos\phi - \cos\theta\sin\psi\sin\phi,$ $c_{21} = -\cos\psi\sin\phi - \cos\theta\sin\psi\cos\phi,$ $c_{31} = \sin\theta\sin\psi,$ $c_{12} = \sin\psi\cos\phi - \cos\theta\cos\psi\sin\phi,$ $c_{22} = -\sin\psi\sin\phi + \cos\theta\cos\psi\cos\phi,$ $c_{32} = -\sin\theta\cos\psi,$ $c_{32} = -\sin\theta\cos\psi,$ $c_{23} = \sin\theta\cos\phi;$ and $c_{33} = \cos\theta$ and $C_{11}=\cos\psi\cos\phi-\cos\theta\sin\psi\sin\phi$, $C_{21}=-\cos\psi\cos\phi-\cos\theta\sin\psi\sin\phi$, $C_{31}=\sin\phi\sin\psi$, $C_{12}=\sin\psi\cos\phi-\cos\theta\cos\psi\sin\phi$, $C_{22}=-\sin\psi\sin\phi+\cos\theta\cos\psi\cos\phi$, $C_{32}=-\sin\theta\cos\psi$, $C_{32}=-\sin\theta\cos\psi$, $C_{32}=\sin\theta\cos\phi$;

$C_{32}=\cos\theta$, are the directional cosines.

The equations $r=A\zeta$ and $\zeta=A^{-1}r$ provide a complete relationship between the coordinate system r and the coordinate system $\zeta$.

For such an arbitrarily oriented 3D image, the correction is performed by:

(1) taking an arbitrarily orientated image in the $\zeta$ coordinate system;

(2) transforming from $\zeta$ coordinate system to the r coordinate system using the $r=A\zeta$; transformation;

(3) correcting the image in the r coordinate system using the correction methods of either the first or second aspects of the invention; and (4) transforming back from the r coordinate system to the $\zeta$ coordinate system using the $\zeta=A^{-1}r$ transformation.

Thereafter, the corrected image can be displayed in the $\zeta$ coordinate system.

In accordance with a third aspect (see generally, the right column of FIG. 8), the invention provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets, where the MR data set is of the form $s(m_X\Delta t_X, m_Y\Delta t_Y, m_Z\Delta t_Z)$ where:

(i) $m_X$, $m_Y$ and $m_Z$ are indices for the data points in the x, y, and z directions, respectively; and (ii) $\Delta t_X$, $\Delta t_Y$ and $\Delta t_Z$ are equivalent time steps in the x, y, and z directions, respectively;

(B) producing an uncorrected image function $\rho(l_X\Delta\omega_X^L, l_Y\Delta\psi_Y^L, l_Z\Delta\omega_Z^L)$ from the MR data set by a process which comprises performing a three dimensional fast Fourier transform on said data set, said uncorrected image function being in frequency space at a set of frequency points given by $(l_X\Delta\omega_X^L, l_Y\Delta\omega_Y^L, l_Z\Delta\omega_Z^L)$ where:

(i) $l_X$, $l_Y$ and $l_Z$ are indices for the frequency points in the $\omega_X^L$, $\omega_Y^L$ and $\omega_Z^L$ directions, respectively;

(ii) $\Delta\omega_X^L$, $\Delta\omega_Y^L$ and $\Delta\omega_Z^L$ are frequency steps in the $\omega_X^L$, $\omega_Y^L$ and $\omega_Z^L$ directions, respectively;

(iii) $\omega_X^L=\gamma xG_X^L$, $\omega_Y^L=\gamma yG_Y^L$, $\omega_Z^L=\gamma zG_Z^L$, where:

(a) $\gamma$ is a constant; and (b) $G_X^L$, $G_Y^L$, and $G_Z^L$ represent the linear parts of the gradients ($G_X$, $G_Y$, $G_Z$) of the magnetic fields produced by the X, Y, and Z gradient magnets, respectively;

(iv) the ranges of $l_X$, $l_Y$, and $l_Z$ are selected so that $l_X\cdot\Delta\omega_X^L$, $l_Y\cdot\Delta\omega_Y^L$, and $l_Z\cdot\Delta\omega_Z^L$ respectively span the frequency ranges that would arise from the X, Y, and Z gradient magnets if those magnets produced purely linear gradient fields in the x, y, and z directions of the x,y,z-coordinate system (e.g., the ranges of $l_X$, $l_Y$, and $l_Z$ are selected based on the number of image points in each of the x, y, and z directions); and (v) the fast Fourier transform is of the form:

$$\rho(l_X\Delta\omega_X^L, l_Y\Delta\omega_Y^L, l_Z\Delta\omega_Z^L) = \sum_{m_X}\sum_{m_Y}\sum_{m_Z} s(m_X\Delta t_X, m_Y\Delta t_Y, m_Z\Delta t_Z)$$

$$e^{i(l_X\Delta\omega_X^L\cdot m_X\Delta t_X + l_Y\Delta\omega_Y^L\cdot m_Y\Delta t_Y + l_Z\Delta\omega_Z^L\cdot m_Z\Delta t_Z)}$$

$$\Delta t_X\Delta t_Y\Delta t_Z$$

(C) producing a corrected image function $\rho(x',y',z')$ at $(x',y',z')$ in the x,y,z-coordinate system from the uncorrected image function $\rho(l_X\Delta\omega_X^L, l_Y\Delta\omega_Y^L, l_Z\Delta\omega_Z^L)$ using an interpolation function L in frequency space of the form:

$$\rho(\omega_X^N, \omega_Y^N, \omega_Z^N) = L(\omega_X^N, \omega_Y^N, \omega_Z^N, \rho(l_X\Delta\omega_X^L, l_Y\Delta\omega_Y^L, l_Z\Delta\omega_Z^L))$$

where:

(i) $\omega_X^N$, $\omega_Y^N$, and $\omega_Z^N$ are each a function of $(x',y',z')$; and (ii) $\rho(\omega_X^N, \omega_Y^N, \omega_Z^N)$ equals the desired $\rho(x',y',z')$;

wherein $G_X^L$, $G_Z^L$, $G_Z^L$, $\omega_X^N$, $\omega_Y^N$, and $\omega_Z^N$ are determined using coefficients of spherical harmonic expansions for the magnetic fields produced by the X, Y, and Z gradient magnets (the "spherical harmonic coefficients").

The quantities $\Delta t_X$, $\Delta t_Y$ and $\Delta t_Z$ are referred to above as "equivalent time steps" for the following reasons. To encode a spatial position a gradient is used. If it is the read gradient, the time issue does not arise as time is determined by the sampling rate of the analog to digital converter (ADC). But this only encodes one direction, e.g., the y-direction. One must then ask how the other directions are encoded, e.g., the x-direction.

In the original spin warp experiment proposed by Ernst in 1976, the second gradient (the phase gradient) (and the third gradient) were applied at constant gradient strength and 256 time increments of each gradient were acquired. If the gradient strength is G and the time increment t, this means that 256 applications of the x gradient with gradient strength G but with time increasing from $0\cdot t\cdot G$ to $255\cdot t\cdot G$ were acquired, each being followed by a constant read gradient to give the xy encoding. The phase shift for a point with x-coordinate x was thus $x\cdot G\cdot n\cdot t$, where n is the step in time. Multiplying this by $\gamma$ gives the phase shift in units of radians.

But the same result is achieved if the gradient is stepped for a fixed on time, call this T. If g is the gradient step size, then the phase shift after the $n^{th}$ incrementation of a constant gradient step is $n\cdot g\cdot T\cdot x$. That is, $n\cdot g\cdot x\cdot T=x\cdot G\cdot n\cdot t$. Thus, the same phase encoding results whether time is incremented for a constant gradient or a gradient is incremented for constant time. It is in this sense that the phrase "equivalent time" is used in the above description of the third aspect of the invention and in the claims.

Certain preferred embodiments of this aspect of the invention are characterized by the following:

(a) $a_{V(n,m)}$ and $b_{V(n,m)}$ are the spherical harmonic coefficients, where the subscript V is one of X, Y, and Z;

(b) $G_X^L=a_{X(1,1)}$, $G_Y^L=b_{Y(1,1)}$, and $G_Z^L=a_{Z(1,0)}$; and (c) $\omega_X^N$, $\omega_Y^N$, and $\omega_Z^N$ are given by:

$$\begin{cases} \omega_X^N = \gamma(x' + \eta_X(x', y', z'))G_X^L \\ \omega_Y^N = \gamma(y' + \eta_Y(x', y', z'))G_Y^L \\ \omega_Z^N = \gamma(z' + \eta_Z(x', y', z'))G_Z^L \end{cases}$$

where $\eta_X(x',y',z')$, $\eta_Y(x',y',z')$ and $\eta_Z(x',y',z')$ are given by:

$$\begin{cases} \eta_X(x', y', z') = \dfrac{B_X^N(r', \theta', \phi')}{G_X^L} \\ \eta_Y(x', y', z') = \dfrac{B_Y^N(r', \theta', \phi')}{G_Y^L} \\ \eta_Z(x', y', z') = \dfrac{B_Z^N(r', \theta', \phi')}{G_Z^L} \end{cases}$$

where $$\begin{cases} B_X^N(r', \theta', \phi') = B_{X(0,0)}(r', \theta', \phi') + B_{X(1,0)}(r', \theta', \phi') + \sum_{n=2}\sum_m B_{X(n,m)}(r', \theta', \phi') \\ B_Y^N(r', \theta', \phi') = B_{Y(0,0)}(r', \theta', \phi') + B_{Y(1,0)}(r', \theta', \phi') + \sum_{n=2}\sum_m B_{Y(n,m)}(r', \theta', \phi') \\ B_Z^N(r', \theta', \phi') = B_{Z(0,0)}(r', \theta', \phi') + B_{Z(1,1)}(r', \theta', \phi') + \sum_{n=2}\sum_m B_{Z(n,m)}(r', \theta', \phi') \end{cases}$$

represent the non-linear parts of the magnetic fields produced by the X, Y, and Z gradient magnets, where:

(i) m and n are the indices of the summations and satisfy the relationship $m \leq n$;

(ii) $B_{V(n,m)}(r',\theta',\phi')$ is given by:

$$B_{V(n,m)}(r',\theta',\phi') = r'^n[a_{V(n,m)}\cos(m\phi') + b_{V(n,m)}\sin(m\phi')]P_{(n,m)}(\cos\theta')$$

where the $P_{(n,m)}(\cos\theta')$ are associated Legendre functions and the subscript V is one of X, Y, and Z; and (iii) $(x', y', z')$ values and $(r', \theta', \phi')$ values are related by:

$$\begin{cases} r' = \sqrt{x'^2 + y'^2 + z'^2} \\ \theta' = \tan^{-1}\left(\dfrac{\sqrt{x'^2 + y'^2}}{z'}\right) \\ \phi' = \tan^{-1}\left(\dfrac{y'}{x'}\right) \end{cases}$$

For the base case, the first two terms of each of the expressions set forth above for the non-linear parts of the magnetic fields produced by the X, Y, and Z gradient magnets are zero or effectively zero.

In other preferred embodiments, the interpolation function L is a sinc function such that:

$$L(\omega_X^N, \omega_Y^N, \omega_Z^N, \rho(l_X\Delta\omega_X^L, l_Y\Delta\omega_Y^L, l_Z\Delta\omega_Z^L)) = \sum_{l_Z}\sum_{l_Y}\sum_{l_X} \rho(l_X\Delta\omega_X^L, l_Y\Delta\omega_Y^L, l_Z\Delta\omega_Z^L)\,\text{sinc}\left(\dfrac{\omega_X^N}{\Delta\omega_X^L} - l_X, \dfrac{\omega_Y^N}{\Delta\omega_Y^L} - l_Y, \dfrac{\omega_Z^N}{\Delta\omega_Z^L} - l_Z\right)$$

In still further preferred embodiments, the interpolation function L is of the form:

$$L(\omega_X^N, \omega_Y^N, \omega_Z^N, \rho(l_X\Delta\omega_X^L, l_Y\Delta\omega_Y^L, l_Z\Delta\omega_Z^L)) = \sum_{l_Z}\sum_{l_Y}\sum_{l_X} C_{(l_X,l_Y,l_Z)}\psi_{X(l_X)}(\omega_X^N)\psi_{Y(l_Y)}(\omega_Y^N)\psi_{Z(l_Z)}(\omega_Z^N)$$

where:

(a) $\psi_{X(l_X)}$, $\psi_{Y(l_Y)}$ and $\psi_{Z(l_Z)}$ are orthogonal bases functions; and (b) the $C_{(l_X,l_Y,l_Z)}$ are coefficients which satisfy the matrix equation:

$$AC = \rho$$

where the vector C is of the form:

$$C = [C_{(1,1,1)}\ C_{(2,1,1)}\ \ldots\ C_{(l_X,l_Y,l_Z)}]^T$$

the vector $\rho$ is of the form:

$$\rho = [\rho(\omega_{X(1)}^L, \omega_{Y(1)}^L, \omega_{Z(1)}^L)\ \rho(\omega_{X(2)}^L, \omega_{Y(1)}^L, \omega_{Z(1)}^L)\ \ldots\ \rho(\omega_{X(l_X)}^L, \omega_{Y(l_Y)}^L, \omega_{Z(l_Z)}^L)]^T$$

and the matrix A is of the form:

$$\begin{bmatrix} \beta_{(1,1)} & \beta_{(1,2)} & \cdots & \beta_{(1,q)} \\ \beta_{(2,1)} & \beta_{(2,2)} & \cdots & \beta_{(2,q)} \\ \vdots & \vdots & \ddots & \vdots \\ \beta_{(q,1)} & \beta_{(q,2)} & \cdots & \beta_{(q,q)} \end{bmatrix}$$

where $\beta_{(1,1)} = \psi_{X(1)}(\omega_{X(1)}^L)\psi_{Y(1)}(\omega_{Y(1)}^L)\psi_{Z(1)}(\omega_{Z(1)}^L)$, $\beta_{(1,2)} = \psi_{X(2)}(\omega_{X(1)}^L)\psi_{Y(1)}(\omega_{Y(1)}^L)\psi_{Z(1)}(\omega_{Z(1)}^L)$, $\vdots$ $\beta_{(1,q)} = \psi_{X(l_X)}(\omega_{X(1)}^L)\psi_{Y(l_Y)}(\omega_{Y(1)}^L)\psi_{Z(l_Z)}(\omega_{Z(1)}^L)$;

$\beta_{(2,1)} = \psi_{X(1)}(\omega_{X(2)}^L)\psi_{Y(1)}(\omega_{Y(1)}^L)\psi_{Z(1)}(\omega_{Z(1)}^L)$, $\beta_{(2,2)} = \psi_{X(2)}(\omega_{X(2)}^L)\psi_{Y(1)}(\omega_{Y(1)}^L)\psi_{Z(1)}(\omega_{Z(1)}^L)$, $\vdots$ $\beta_{(2,q)} = \psi_{X(l_X)}(\omega_{X(2)}^L)\psi_{Y(l_Y)}(\omega_{Y(1)}^L)\psi_{Z(l_Z)}(\omega_{Z(1)}^L)$;

$\vdots$ $\beta_{(q,1)} = \psi_{X(1)}(\omega_{X(l_X)}^L)\psi_{Y(1)}(\omega_{Y(l_Y)}^L)\psi_{Z(1)}(\omega_{Z(l_Z)}^L)$, $\beta_{(q,2)} = \psi_{X(2)}(\omega_{X(l_X)}^L)\psi_{Y(1)}(\omega_{Y(l_Y)}^L)\psi_{Z(1)}(\omega_{Z(l_Z)}^L)$, $\beta_{(q,q)} = \psi_{X(l_X)}(\omega_{X(l_X)}^L)\psi_{Y(l_Y)}(\omega_{Y(l_Y)}^L)\psi_{Z(l_Z)}(\omega_{Z(l_Z)}^L)$, where $q \leq [l_X \times l_Y \times l_Z]_{max}$.

In connection with these embodiments:

(a) the interpolation preferably comprises Lagrange's interpolation, Newton interpolation, finite difference interpolation, Hermite interpolation, spline interpolation, or combinations thereof; and/or (b) the interpolation is applied to:

(i) all of the data points obtained by performing the three dimensional fast Fourier transform on the MR data set; or (ii) a subset of the data points obtained by performing the three dimensional fast Fourier transform on the MR data set, said subset being in the vicinity of a region of interest of the object being imaged.

As with the first and second aspects of the invention, the third aspect of the invention can be employed to achieve corrected images for arbitrary 3D imaging. In terms of frequencies, the transformations are as follows:

$$\omega_{(X,Y,Z)} = A\omega_{(\zeta_1,\zeta_2,\zeta_3)}, \text{ and}$$

$$\omega_{(\zeta_1,\zeta_2,\zeta_3)} = A^{-1}\omega_{(X,Y,Z)},$$

where $\omega_{(X,Y,Z)} = [\omega_X, \omega_Y, \omega_Z]^T$,
$\omega_{(\zeta_1,\zeta_2,\zeta_3)} = [\omega_{\zeta_1}, \omega_{\zeta_2}, \omega_{\zeta_3}]^T$, and
A is the same as above.

The correction for this case is performed by:

(1) taking an arbitrarily orientated image in terms of the frequencies $\omega_{(\zeta_1,\zeta_2,\zeta_3)}$;

(2) transforming from the $\omega_{(\zeta_1,\zeta_2,\zeta_3)}$ frequencies to the $\omega_{(X,Y,Z)}$ frequencies using the $\omega_{(X,Y,Z)} = A\omega_{(\zeta_1,\zeta_2,\zeta_3)}$ transformation;

(3) correcting the image in the $\omega_{(X,Y,Z)}$ frequency space using the correction methods of the third aspect of the invention; and (4) transforming from the $\omega_{(X,Y,Z)}$ frequencies back to the $\omega_{(\zeta_1,\zeta_2,\zeta_3)}$ frequencies using the $\omega_{(\zeta_1,\zeta_2,\zeta_3)} = A^{-1}\omega_{(X,Y,Z)}$ transformation.

Thereafter, the corrected image can be displayed in the $\zeta$ coordinate system.

In accordance with each of the first, second, and third aspects of the invention, $\rho(x',y',z')$ is preferably displayed as a corrected image. Even more preferably, as illustrated in FIG. 9, an image function $\rho(x'',y'',z'')$ having uniform pixel dimensions is produced from $\rho(x',y',z')$ by performing an interpolation of the form:

$$\rho(x'',y'',z'') = H(x'',y'',z'',\rho(x',y',z'))$$

where H is an interpolation function and (x'',y'',z'') are uniformly distributed point coordinates in the x,y,z-coordinate system. Examples of suitable interpolation procedures include: Lagrange interpolation, Newton interpolation, finite differences interpolation, Hermite interpolation, spline interpolation, or combinations thereof. Once computed, the image function $\rho(x'',y'',z'')$ is preferably displayed as a corrected image. In the case of case of arbitrary 3D imaging, the interpolation can be performed on the corrected image either before or after the back transformation step.

The foregoing three aspects of the invention relate to three dimensional imaging. The following three aspects relate to two dimensional slice imaging. In overview, the fourth, fifth, and sixth aspects employ correction techniques which generally correspond to those of the first, second, and third aspects, respectively, but in two dimensions, rather than three. FIG. 1B shows the coordinate nomenclature employed in the discussion of these two-dimensional aspects of the invention.

As in the first three aspects of the invention, the magnetic resonance imaging system for the fourth, fifth, and sixth aspects of the invention defines an origin of an (x, y, z) coordinate system (the "x,y,z-coordinate system") and comprises X, Y and Z gradient magnets which produce magnetic fields having gradients ($G_X$, $G_Y$, $G_Z$), respectively.

Based on the geometry of FIG. 1B, the slice select gradient for an oblique slice can be defined as:

$$G_3 = (p_{X3}G_X, p_{Y3}G_Y, p_{Z3}G_Z)$$

where ($p_{X3}$, $p_{Y3}$, $p_{Z3}$) are gradient strength coefficients of the X, Y, and Z gradient magnets ($G_X$, $G_Y$, $G_Z$), respectively, $|G_3| = \sqrt{(p_{X3}G_X)^2 + (p_{Y3}G_Y)^2 + (p_{Z3}G_Z)^2}$ is the slice selection gradient amplitude, and the axis direction of that gradient is:

$$\hat{\zeta}_3 = (\sin\theta_3\cos\phi_3, \sin\theta_3\sin\phi_3, \cos\theta_3)$$

where $$\theta_3 = \tan^{-1}\frac{\sqrt{(p_{X3}G_X)^2 + (p_{Y3}G_Y)^2}}{p_{Z3}G_Z}, \text{ and}$$

$$\phi_3 = \tan^{-1}\left(\frac{p_{Y3}G_Y}{p_{X3}G_X}\right).$$

Transverse, coronal, and sagittal slices then correspond to:

Transverse:

$(p_{X3}, p_{Y3}, p_{Z3}) = (0, 0, 1)$ $G_3 = (0, 0, G_Z)$ $|G_3| = |G_Z|$ $\hat{\zeta}_3 = \hat{z}$;

Coronal:

$(p_{X3}, p_{Y3}, p_{Z3}) = (0, 1, 0)$ $G_3 = (0, G_Y, 0)$ $|G_3| = |G_Y|$ $\hat{\zeta}_3 = \hat{y}$;

Sagittal:

$(p_{X3}, p_{Y3}, p_{Z3}) = (1, 0, 0)$ $G_3 = (G_X, 0, 0)$ $|G_3| = |G_X|$ $\hat{\zeta}_3 = \hat{x}$.

Again based on the geometry of FIG. 1B, the phase encoding gradient for an oblique slice can be defined as:

$$G_2 = (p_{X2}G_X, p_{Y2}G_Y, p_{Z2}G_Z) \text{ such that } \hat{\zeta}_3 \cdot \hat{\zeta}_2 = 0,$$

where ($p_{X2}$, $p_{Y2}$, $p_{Z2}$) are gradient strength coefficients of the X, Y and Z gradient magnets ($G_X$, $G_Y$, $G_Z$), respectively, $|G_2| = \sqrt{(p_{X2}G_X)^2 + (p_{Y2}G_Y)^2 + (p_{Z2}G_Z)^2}$ is the phase encoding gradient amplitude, and the axis direction of that gradient is:

$$\hat{\zeta}_2 = (\sin\theta_2\cos\phi_2, \sin\theta_2\sin\phi_2, \cos\theta_2)$$

where $$\theta_2 = \tan^{-1}\frac{\sqrt{(p_{X2}G_X)^2 + (p_{Y2}G_Y)^2}}{p_{Z2}G_Z}, \text{ and}$$

$$\phi_2 = \tan^{-1}\left(\frac{p_{Y2}G_Y}{p_{X2}G_X}\right).$$

Finally, based on FIG. 1B, the read gradient for an oblique slice can be defined as:

$$G_1 = (p_{X1}G_X, p_{Y1}G_Y, p_{Z1}G_Z), \text{ such that } \hat{\zeta}_3 \cdot \hat{\zeta}_1 = 0,$$

where ($p_{X1}$, $P_{Y1}$, $p_{Z1}$) are gradient strength coefficients of the X, Y and Z gradient magnets ($G_X$, $G_Y$, $G_Z$), respectively, $|G_1|=\sqrt{(p_{X1}G_X)^2+(p_{Y1}G_Y)^2+(p_{Z1}G_Z)^2}$ is the read gradient amplitude, and the axis direction of that gradient is $$\hat{\zeta}_1 = (\sin\theta_1\cos\phi_1, \sin\theta_1\sin\phi_1, \cos\theta_1)$$

where $$\theta_1 = \tan^{-1}\frac{\sqrt{(p_{X1}G_X)^2+(p_{Y1}G_Y)^2}}{p_{Z1}G_Z}, \text{ and}$$

$$\phi_1 = \tan^{-1}\left(\frac{p_{Y1}G_Y}{p_{X1}G_X}\right).$$

The coordinate system ($\zeta_1$, $\zeta_2$, $\zeta_3$) defined in this way can be seen to be a linear combination of the X, Y and Z gradient magnets ($G_X$, $G_Y$, $G_Z$) in the coordinate system (x, y, z). The new coordinate system ($\zeta_1$, $\zeta_2$, $\zeta_3$) has the same origin as the (x, y, z) coordinate system and the transformations between the coordinate systems can be written as:

$$r = r_0 + A \cdot (\zeta - \zeta_0), \text{ and}$$

$$\zeta = \zeta_0 + A^{-1}(r - r_0),$$

where A is a slice rotation matrix given by:

$$A = \begin{bmatrix} \sin\theta_1\cos\phi_1 & \sin\theta_1\sin\phi_1 & \cos\theta_1 \\ \sin\theta_2\cos\phi_2 & \sin\theta_2\sin\phi_2 & \cos\theta_2 \\ \sin\theta_3\cos\phi_3 & \sin\theta_3\sin\phi_3 & \cos\theta_3 \end{bmatrix}$$

$A^{-1}$ is the inverse of the matrix, and $$r=(x,y,z)^T,$$

$$r_0=(x_0,y_0,z_0)^T,$$

$$\zeta=(\zeta_1,\zeta_2,\zeta_3)^T, \text{ and}$$

$$\zeta_0=(0,0,\zeta_3)^T.$$

In this transformation, $r_0=(x_0,y_0,z_0)^T$ is the slice position in the (x, y, z) coordinate system with:

$$(x_0,y_0,z_0)=(\zeta_3 \sin\theta_3 \cos\phi_3, \zeta_3 \sin\theta_3 \sin\phi_3, \zeta_3 \cos\theta_3),$$

and $(0,0,\zeta_3)$ is the slice position along the slice axis $\hat{\zeta}_3$ in the ($\zeta_1$, $\zeta_2$, $\zeta_3$) coordinate system, with:

$$\zeta_3=\sqrt{x_0^2+y_0^2+z_0^2}.$$

As discussed above, the linear parts of the gradient fields of the X, Y, and Z gradient magnets in the x,y,z-coordinate system are given by ($G_X^L=a_{X(1,1)}$, $G_Y^L=b_{Y(1,1)}$, $Z_X^L=a_{Z(1,0)}$). The linear parts of the $G_1$ and $G_2$ gradients (also referred to herein and in the claims as, respectively, the "$G_1$ gradient" and the "$G_2$ gradient," or collectively as the "gradients ($G_1$, $G_2$)") can be written as:

$$G_1^L = G_1^L \cdot \hat{\zeta}_1 = p_{X1}a_{X(1,1)}+p_{Y1}a_{Y(1,1)}+p_{Z1}a_{Z(1,0)}$$

$$G_2^L = G_2^L \cdot \hat{\zeta}_2 = p_{X2}a_{X(1,1)}+p_{Y2}a_{Y(1,1)}+p_{Z2}a_{Z(1,0)}.$$

In terms of the foregoing nomenclature, the invention in accordance with a fourth aspect provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice (e.g., a transverse, coronal, sagittal, or oblique slice) of the object in two dimensions in data space using a linear combination of the X, Y, and Z gradient magnets;

(B) producing an uncorrected image function $\rho(\zeta_1,\zeta_2)$ from the MR data set by a process which comprises performing a two dimensional fast Fourier transform on said data set, where $\zeta_1$ and $\zeta_2$ are read and phase encoding coordinates, respectively, of a ($\zeta_1,\zeta_2,\zeta_3$) coordinate system as defined above;

(C) producing a corrected image function $\rho(\zeta_1',\zeta_2')$ from the uncorrected image function $\rho(\zeta_1,\zeta_2)$, where the coordinates ($\zeta_1',\zeta_2'$) represent a corrected position in the ($\zeta_1,\zeta_2,\zeta_3$) coordinate system for the value of the image function at ($\zeta_1,\zeta_2$), said ($\zeta_1',\zeta_2'$) coordinates being determined using an iterative mapping which employs coefficients of spherical harmonic expansions for the magnetic fields produced by the X, Y, and Z gradient magnets (the "spherical harmonic coefficients").

In certain preferred embodiments of this aspect of the invention, the iterative mapping is of the form:

$$\begin{cases} \zeta_1' = \zeta_1 - \eta_1(\zeta_1',\zeta_2') \\ \zeta_2' = \zeta_2 - \eta_2(\zeta_1',\zeta_2') \end{cases}$$

where $$\begin{cases} \zeta_{1(1)}' = \zeta_1 - \eta_1(\zeta_1,\zeta_2) \\ \zeta_{2(1)}' = \zeta_2 - \eta_2(\zeta_1,\zeta_2) \end{cases}, \begin{cases} \zeta_{1(2)}' = \zeta_1 - \eta_1(\zeta_{1(1)}',\zeta_{2(1)}') \\ \zeta_{2(2)}' = \zeta_2 - \eta_2(\zeta_{1(1)}',\zeta_{2(1)}') \end{cases}, \ldots,$$

$$\begin{cases} \zeta_{1(n)}' = \zeta_1 - \eta_1(\zeta_{1(n-1)}',\zeta_{2(n-1)}') \\ \zeta_{2(n)}' = \zeta_2 - \eta_2(\zeta_{1(n-1)}',\zeta_{2(n-1)}') \end{cases}$$

where n is the iteration number and $\eta_1(\zeta_1,\zeta_2)=\eta_1(\zeta_1,\zeta_2,\zeta_3)$ and $\eta_2(\zeta_1,\zeta_2)=\eta_2(\zeta_1,\zeta_2,\zeta_3)$ are given by:

$$\begin{cases} \eta_1(\zeta_1,\zeta_2,\zeta_3) = \dfrac{B_1^N(r,\theta,\phi)}{G_1^L \cdot \hat{\zeta}_1} \\ \eta_2(\zeta_1,\zeta_2,\zeta_3) = \dfrac{B_2^N(r,\theta,\phi)}{G_2^L \cdot \hat{\zeta}_2} \end{cases}$$

where (a) r, θ and φ are defined relative to the same origin as the $\zeta_1$, $\zeta_2$ and $\zeta_3$ coordinate system and are given by:

(i) $r = r_0 + A \cdot (\zeta - \zeta_0)$; and (ii) $\left(r = \sqrt{x^2+y^2+z^2}, \theta = \tan^{-1}\left(\dfrac{\sqrt{x^2+y^2}}{z}\right), \phi = \tan^{-1}\left(\dfrac{y}{x}\right)\right)$;

(b) ($G_1^L$, $G_2^L$) represent the linear part of the gradients ($G_1$, $G_2$) of the magnetic fields produced by the X, Y, and Z gradient magnets; and (c)

$$\begin{cases} B_1^N(r,\theta,\phi) = p_{X1}\left(B_{X(0,0)}(r,\theta,\phi) + B_{X(1,0)}(r,\theta,\phi) + \sum_{n=2}\sum_m B_{X(n,m)}(r,\theta,\phi)\right) + p_{Y1}\left(B_{Y(0,0)}(r,\theta,\phi) + B_{Y(1,0)}(r,\theta,\phi) + \sum_{n=2}\sum_m B_{Y(n,m)}(r,\theta,\phi)\right) + \\ p_{Z1}\left(B_{Z(0,0)}(r,\theta,\phi) + B_{Z(1,1)}(r,\theta,\phi) + \sum_{n=2}\sum_m B_{Z(n,m)}(r,\theta,\phi)\right) \\ B_2^N(r,\theta,\phi) = p_{X2}\left(B_{X(0,0)}(r,\theta,\phi) + B_{X(1,0)}(r,\theta,\phi) + \sum_{n=2}\sum_m B_{X(n,m)}(r,\theta,\phi)\right) + p_{Y2}\left(B_{Y(0,0)}(r,\theta,\phi) + B_{Y(1,0)}(r,\theta,\phi) + \sum_{n=2}\sum_m B_{Y(n,m)}(r,\theta,\phi)\right) + p_{Z2}\left(B_{Z(0,0)}(r,\theta,\phi) + B_{Z(1,1)}(r,\theta,\phi) + \sum_{n=2}\sum_m B_{Z(n,m)}(r,\theta,\phi)\right) \end{cases}$$

represent the non-linear parts of the magnetic fields produced by the X, Y, and Z gradient magnets; where (i) m and n are the indices of the summations and satisfy the relationship m≤n;

(ii) the $B_{V(n,m)}(r,\theta,\phi)$ are given by:

$$B_{V(n,m)}(r,\theta,\phi) = r^n[a_{V(n,m)}\cos(m\phi) + b_{V(n,m)}\sin(m\phi)]P_{(n,m)}(\cos\theta),$$

where the $P_{(n,m)}(\cos\theta)$ are the associated Legendre functions and the subscript V is one of X, Y, and Z; and (iii) $a_{V(n,m)}$ and $b_{V(n,m)}$ are the spherical harmonic coefficients, where again, the subscript V is one of X, Y, and Z.

For the base case, the magnitudes of the X(0,0), X(1,0), Y(0,0), Y(1,0), and Z(0,0) field components are zero or effectively zero.

Preferably, the iterative mapping is continued until the following condition is satisfied:

$$\frac{\sqrt{(\zeta'_{1(n)} - \zeta'_{1(n-1)})^2 + (\zeta'_{2(n)} - \zeta'_{2(n-1)})^2}}{\sqrt{(\zeta'_{1(n)} - \zeta_1)^2 + (\zeta'_{2(n)} - \zeta_2)^2}} \leq \varepsilon$$

where, for example, $\varepsilon = 10^{-3}$. In such a case, the number of iterations is typically between 2 and 4.

In accordance with a fifth aspect, the invention provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice (e.g., a transverse, coronal, sagittal, or oblique slice) of the object in two dimensions in data space using a linear combination of the X, Y, and Z gradient magnets;

(B) producing an uncorrected image function $\rho(\zeta_1, \zeta_2)$ from the MR data set by a process which comprises performing a two dimensional fast Fourier transform on said data set, where $\zeta_1$ and $\zeta_2$ are read and phase encoding coordinates, respectively, of a $(\zeta_1, \zeta_2, \zeta_3)$ coordinate system as defined above;

(C) producing a corrected image function $\rho(\zeta_1', \zeta_2')$ from the uncorrected image function $\rho(\zeta_1, \zeta_2)$, where the coordinates $(\zeta_1', \zeta_2')$ represent a corrected position in the $(\zeta_1, \zeta_2, \zeta_3)$ coordinate system for the value of the image function at $(\zeta_1, \zeta_2)$, said $(\zeta_1', \zeta_2')$ coordinates being determined by solving a system of non-linear equations so that an error function $f(\zeta_1', \zeta_2')$ satisfies the relationship:

$$\|f(\zeta_1', \zeta_2')\| \leq \varepsilon$$

where $\varepsilon$ is a predetermined constant;

wherein the system of non-linear equations employs coefficients of spherical harmonic expansions for the magnetic fields produced by the X, Y, and Z gradient magnets (the "spherical harmonic coefficients").

Preferably, the system of non-linear equations is solved iteratively (e.g., using a Levenberg-Marquardt non-linear curve fitting technique or a non-linear minimization technique) using $\zeta'_{1(0)} = \zeta_1$ and $\zeta'_{2(0)} = \zeta_2$ as the initial $(\zeta'_1, \zeta'_2)$ values and an error function and system of non-linear equations of the form:

$$f(\zeta_1', \zeta_2') = \begin{cases} f_1(\zeta_1', \zeta_2', \zeta_3') = B_1^{LN}(r', \theta', \phi') - G_1^L \cdot \zeta_1 \cong 0 \\ f_2(\zeta_1', \zeta_2', \zeta_3') = B_2^{LN}(r', \theta', \phi') - G_2^L \cdot \zeta_2 \cong 0 \end{cases}$$

where:

(a) (r', θ', φ') and ($\zeta_1'$, $\zeta_2'$, $\zeta_3'$) values are related by:

$$\left(r' = \sqrt{x'^2 + y'^2 + z'^2}, \theta' = \tan^{-1}\left(\frac{\sqrt{x'^2 + y'^2}}{z'}\right), \phi' = \tan^{-1}\left(\frac{y'}{x'}\right)\right)$$

and $$r' = r_0' + A \cdot (\zeta' - \zeta_0')$$

(b) ($G_1^L$, $G_2^L$) represent the linear part of the gradients ($G_1$, $G_2$) of the magnetic fields produced by the X, Y, and Z gradient magnets; and (c)

$$\begin{cases} B_1^{LN}(r,\theta,\phi) = p_{X1}\left(\sum_{n=0}\sum_m B_{X(n,m)}(r,\theta,\phi)\right) + p_{Y1}\left(\sum_{n=0}\sum_m B_{Y(n,m)}(r,\theta,\phi)\right) + p_{Z1}\left(\sum_{n=0}\sum_m B_{Z(n,m)}(r,\theta,\phi)\right) \\ B_2^{LN}(r,\theta,\phi) = p_{X2}\left(\sum_{n=0}\sum_m B_{X(n,m)}(r,\theta,\phi)\right) + p_{Y2}\left(\sum_{n=0}\sum_m B_{Y(n,m)}(r,\theta,\phi)\right) + p_{Z2}\left(\sum_{n=0}\sum_m B_{Z(n,m)}(r,\theta,\phi)\right) \end{cases}$$

represent the linear and non-linear parts of the magnetic fields produced by the X, Y, and Z gradient magnets, where (i) m and n are the indices of the summations and satisfy the relationship m≤n;

(ii) the $B_{V(n,m)}(r',\theta',\phi')$ are given by:

$$B_{V(n,m)}(r',\theta',\phi') = r'^n[a_{V(n,m)}\cos(m\phi') + b_{V(n,m)}\sin(m\phi')]P_{(n,m)}(\cos\theta')$$

where the $P_{(n,m)}(\cos\theta')$ are the associated Legendre functions and the subscript V is one of X, Y, and Z; and (iii) $a_{V(n,m)}$ and $b_{V(n,m)}$ are the spherical harmonic coefficients, where again, the subscript V is one of X, Y, and Z.

For the base case, the summations in subparagraph (c) can begin with n=1 rather than n=0 if desired.

As in the second aspect of the invention, $\varepsilon$ preferably satisfies the relationship:

$$\varepsilon = R_{es} \times 10^{-3}$$

where $R_{es}$ is the resolution of the image given by:

$$R_{es} = A_{image}/N_{pix},$$

where $A_{image}$ is the area of the image and $N_{pix}$ is total number of pixels making up the image.

In accordance with a sixth aspect, the invention provides a method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice (e.g., a transverse, coronal, sagittal, or oblique slice) of the object in two dimensions in data space using a linear combination of the X, Y, and Z gradient magnets, where the MR data set is of the form $s(m_1 \Delta t_1, m_2 \Delta t_2)$ where:

(i) $m_1$ and $m_2$ are respectively indices for the k-space data points in the $\hat{\zeta}_1$ and $\hat{\zeta}_2$ directions defined above; and (ii) $\Delta t_1$ and $\Delta t_2$ are respectively equivalent time steps in k-space for the $\hat{\zeta}_1$ and $\hat{\zeta}_2$ directions defined above, where equivalent time has the meaning discussed above in connection with the third aspect of the invention;

(B) producing an uncorrected image function $\rho(l_1 \Delta \omega_1^L, l_2 \Delta \omega_2^L)$ from the MR data set by a process which comprises performing a two dimensional fast Fourier transform on said data set, said uncorrected image function being in frequency space at a set of frequency points given by $(l_1 \Delta \omega_1^L, l_2 \Delta \omega_2^L)$ where:

(i) $l_1$ and $l_2$ are indices for the frequency points in the $\omega_1^L$ and $\omega_2^L$ directions, respectively;

(ii) $\Delta \omega_1^L$ and $\Delta \omega_2^L$ are frequency steps in the $\omega_1^L$ and $\omega_2^L$ directions, respectively;

(iii) $\omega_1^L = \gamma G_1^L \cdot \hat{\zeta}_1$, $\omega_2^L = \gamma G_2^L \cdot \hat{\zeta}_2$, where:

(a) $\gamma$ is a constant; and (b) ($G_1^L$, $G_2^L$) represent the linear parts of the gradients ($G_1$, $G_2$) of the magnetic fields produced by the X, Y, and Z gradient magnets;

(iv) the range of $l_1$ is selected so that $l_1 \cdot \Delta \omega_1^L$ spans the frequency range that would arise from the $G_1$ gradient if that gradient were purely linear in the $\hat{\zeta}_1$ direction and the range of $l_1$ is selected so that $l_1 \cdot \Delta \omega_1^L$ spans the frequency range that would arise from the $G_2$ gradient if that gradient were purely linear field in the $\hat{\zeta}_2$ direction; and (v) the fast Fourier transform is of the form:

$$\rho(l_1 \Delta \omega_1^L, l_2 \Delta \omega_2^L) = \sum_{m_2} \sum_{m_1} s(m_1 \Delta t_1, m_2 \Delta t_2) e^{i(l_1 \Delta \omega_1^L \cdot m_1 \Delta t_1 + l_2 \Delta \omega_2^L \cdot m_2 \Delta t_2)} \Delta t_1 \Delta t_2$$

(C) producing a corrected image function $\rho(\zeta_1', \zeta_2')$ in frequency space at $(\zeta_1', \zeta_2', \zeta_3')$ in the $(\zeta_1, \zeta_2, \zeta_3)$ coordinate system from the uncorrected image function $\rho(l_1 \Delta \omega_1^L, l_2 \Delta \omega_2^L)$ using an interpolation function L in frequency space of the form:

$$\rho(\omega_1^N(\zeta_1', \zeta_2', \zeta_3'), \omega_2^N(\zeta_1', \zeta_2', \zeta_3')) = L(\omega_1^N, \omega_2^N, \rho(l_1 \Delta \omega_1^L, l_2 \Delta \omega_2^L))$$

where:

(i) $\rho(\omega_1^N(\zeta_1', \zeta_2', \zeta_3'), \omega_2^N(\zeta_1', \zeta_2', \zeta_3'))$ is the desired $\rho(\zeta_1', \zeta_2')$; and (ii) $G_1^L, G_2^L, \omega_1^N(\omega_1^N(\zeta_1', \zeta_2', \zeta_3'))$, and $\omega_2^N(\zeta_1', \zeta_2', \zeta_3')$ are determined using coefficients of spherical harmonic expansions for the magnetic fields produced by the X, Y, and Z gradient magnets (the "spherical harmonic coefficients").

Certain preferred embodiments of this aspect of the invention are characterized by the following:

(a) $a_{V(n,m)}$ and $b_{V(n,m)}$ are the spherical harmonic coefficients, where the subscript V is one of X, Y, and Z;

(b) $G_1^L = p_{X1} a_{X(1,1)} + p_{Y1} a_{Y(1,1)} + p_{Z1} a_{Z(1,0)}$, and $$G_2^L = p_{X2} a_{X(1,1)} + p_{Y2} a_{Y(1,1)} + P_{Z2} a_{Z(1,0)};$$ and (c) $\omega_1^N(\zeta_1', \zeta_2', \zeta_3')$ and $\omega_2^N(\zeta_1', \zeta_2', \zeta_3')$ are given by:

$$\begin{cases} \omega_1^N(\zeta_1', \zeta_2', \zeta_3') = \gamma(\zeta_1' + \eta_1(\zeta_1', \zeta_2', \zeta_3'))(G_1^L \cdot \hat{\zeta}_1) \\ \omega_2^N(\zeta_1', \zeta_2', \zeta_3') = \gamma(\zeta_2' + \eta_2(\zeta_1', \zeta_2', \zeta_3'))(G_2^L \cdot \hat{\zeta}_2) \end{cases}$$

where $\eta_1(\zeta_1', \zeta_2', \zeta_3')$ and $\eta_2(\zeta_1', \zeta_2', \zeta_3')$ are given by:

$$\begin{cases} \eta_1(\zeta_1', \zeta_2', \zeta_3') = \dfrac{B_1^N(r', \theta', \phi')}{G_1^L \cdot \hat{\zeta}_1} \\ \eta_2(\zeta_1', \zeta_2', \zeta_3') = \dfrac{B_2^N(r', \theta', \phi')}{G_2^L \cdot \hat{\zeta}_2} \end{cases}$$

where $$\begin{cases} B_1^N(r, \theta, \phi) = p_{X1}\left(B_{X(0,0)}(r, \theta, \phi) + B_{X(1,0)}(r, \theta, \phi) + \sum_{n=2}\sum_m B_{X(n,m)}(r, \theta, \phi)\right) + \\ \qquad p_{Y1}\left(B_{Y(0,0)}(r, \theta, \phi) + B_{Y(1,0)}(r, \theta, \phi) + \sum_{n=2}\sum_m B_{Y(n,m)}(r, \theta, \phi)\right) + \\ \qquad p_{Z1}\left(B_{Z(0,0)}(r, \theta, \phi) + B_{Z(1,1)}(r, \theta, \phi) + \sum_{n=2}\sum_m B_{Z(n,m)}(r, \theta, \phi)\right) \\ B_2^N(r, \theta, \phi) = p_{X2}\left(B_{X(0,0)}(r, \theta, \phi) + B_{X(1,0)}(r, \theta, \phi) + \sum_{n=2}\sum_m B_{X(n,m)}(r, \theta, \phi)\right) + \\ \qquad p_{Y2}\left(B_{Y(0,0)}(r, \theta, \phi) + B_{Y(1,0)}(r, \theta, \phi) + \sum_{n=2}\sum_m B_{Y(n,m)}(r, \theta, \phi)\right) + \\ \qquad p_{Z2}\left(B_{Z(0,0)}(r, \theta, \phi) + B_{Z(1,1)}(r, \theta, \phi) + \sum_{n=2}\sum_m B_{Z(n,m)}(r, \theta, \phi)\right) \end{cases}$$

represent the non-linear parts of the magnetic fields produced by the X, Y, and Z gradient magnets, where:
(i) m and n are the indices of the summations and satisfy the relationship $m \leq n$;
(ii) $B_{V(n,m)}(r',\theta',\phi')$ is given by:

$$B_{V(n,m)}(r',\theta',\phi') = r'^n [a_{V(n,m)} \cos(m\phi') + b_{V(n,m)} \sin(m\phi')] P_{(n,m)}(\cos \theta')$$

where the $P_{(n,m)}(\cos \theta')$ are associated Legendre functions and the subscript V is one of X, Y, and Z; and
(iii) $(r', \theta', \phi')$ and $(\zeta_1', \zeta_2', \zeta_3')$ values are related by:

$$\left( r' = \sqrt{x'^2 + y'^2 + z'^2}, \; \theta' = \tan^{-1}\left(\frac{\sqrt{x'^2 + y'^2}}{z'}\right), \; \phi' = \tan^{-1}\left(\frac{y'}{x'}\right) \right)$$

and $$r' = r_0' + A \cdot (\zeta' - \zeta_0').$$

For the base case, the magnitudes of the X(0,0), X(1,0), Y(0,0), Y(1,0), and Z(0,0) field components are zero or effectively zero.

In other preferred embodiments, the interpolation function L is a sinc function such that:

$$L(\omega_1^N, \omega_2^N, \rho(l_1 \Delta \omega_1^L, l_2 \Delta \omega_2^L)) = \sum_{l_2} \sum_{l_1} \rho(l_1 \Delta \omega_1^L, l_2 \Delta \omega_2^L) \operatorname{sinc}\left( \frac{\omega_1^N}{\Delta \omega_1^L} - l_1, \frac{\omega_2^N}{\Delta \omega_2^L} - l_2 \right)$$

In still further preferred embodiments, the interpolation function L is of the form:

$$L(\omega_1^N, \omega_2^N, \rho(l_1 \Delta \omega_1^L, l_2 \Delta \omega_2^L)) = \sum_{l_2} \sum_{l_1} C_{(l_1, l_2)} \psi_{1(l_1)}(\omega_1^N) \psi_{2(l_2)}(\omega_2^N)$$

where:
(a) $\psi_{1(l_1)}$ and $\psi_{2(l_2)}$ are orthogonal bases functions; and
(b) the $C_{(l_1, l_2)}$ are coefficients which satisfy the matrix equation:

$$AC = \rho$$

where the vector C is of the form:

$$C = [C_{(1,1)} C_{(2,1)} \ldots C_{(l_1, l_2)}]^T$$

the vector $\rho$ is of the form:

$$\rho = [\rho(\omega_{1(1)}^L, \omega_{2(1)}^L) \rho(\omega_{1(2)}^L, \omega_{2(1)}^L) \ldots \rho(\omega_{1(l_1)}^L, \omega_{2(l_2)}^L)]^T$$

and the matrix A is of the form:

$$\begin{bmatrix} \psi_{1(1)}(\omega_{1(1)}^L)\psi_{2(1)}(\omega_{2(1)}^L) & \psi_{1(2)}(\omega_{1(1)}^L)\psi_{2(1)}(\omega_{2(1)}^L) & \cdots & \psi_{1(l_1)}(\omega_{1(1)}^L)\psi_{2(l_2)}(\omega_{2(1)}^L) \\ \psi_{1(1)}(\omega_{1(2)}^L)\psi_{2(1)}(\omega_{2(1)}^L) & \psi_{1(2)}(\omega_{1(2)}^L)\psi_{2(1)}(\omega_{2(1)}^L) & \cdots & \psi_{1(l_1)}(\omega_{1(2)}^L)\psi_{2(l_2)}(\omega_{2(1)}^L) \\ \vdots & \vdots & \ddots & \vdots \\ \psi_{1(1)}(\omega_{1(l_1)}^L)\psi_{2(1)}(\omega_{2(l_2)}^L) & \psi_{1(2)}(\omega_{1(l_1)}^L)_2\psi_{2(1)}(\omega_{2(l_2)}^L) & \cdots & \psi_{1(l_1)}(\omega_{1(l_1)}^L)\psi_{2(l_2)}(\omega_{2(l_2)}^L) \end{bmatrix}$$

In connection with these embodiments:
(a) the interpolation preferably comprises Lagrange's interpolation, Newton interpolation, finite difference interpolation, Hermite interpolation, spline interpolation, or combinations thereof; and/or (b) the interpolation is applied to:
(i) all of the data points obtained by performing the two dimensional fast Fourier transform on the MR data set; or
(ii) a subset of the data points obtained by performing the two dimensional fast Fourier transform on the MR data set, said subset being in the vicinity of a region of interest of the object being imaged.

As with the first, second, and third aspects of the invention, $\rho(\zeta_1', \zeta_2')$ is preferably displayed as a corrected image. Even more preferably, an image function $\rho(\zeta_1'', \zeta_2'')$ having uniform pixel dimensions is produced from $\rho(\zeta_1', \zeta_2')$ by performing an interpolation of the form:

$$\rho(\zeta_1'', \zeta_2'') = H(\zeta_1'', \zeta_2'', \rho(\zeta_1', \zeta_2'))$$

where H is an interpolation function and $(\zeta_1'', \zeta_2'')$ are uniformly distributed point coordinates in the $(\zeta_1, \zeta_2, \zeta_3)$ coordinate system. Examples of suitable interpolation procedures include: Lagrange interpolation, Newton interpolation, finite differences interpolation, Hermite interpolation, spline interpolation, or combinations thereof. Once computed, the image function $\rho(\zeta_1'', \zeta_2'')$ is preferably displayed as a corrected image.

As discussed in detail above, in accordance with each of the foregoing six aspects of the invention, the spherical harmonic coefficients are preferably obtained by operating each of the gradient magnets separately at a constant current, although, if desired, less than all of the magnets can be actually measured and/or theoretical values for some or all of the magnets can be used. In practice, the harmonic coefficients of the X, Y, and Z gradient coils are preferably stored in the computer system used to process the magnetic resonance images so that they are readily available for use in image correction calculations.

Also for each of the foregoing six aspects, the following should be noted:

(1) The origin of the x,y,z-coordinate system defined by the magnetic resonance imaging system will generally be at the center of the image region, but can be at other locations if desired (see Section (V) (E) below). By using this origin to determine the spherical harmonic coefficients for both the main magnet and the gradient magnets, the inhomogeneity in the field produced by the main magnet, as represented by the spherical harmonic coefficients determined for that magnet, can be readily taken into account in determining the non-linearities of the gradient magnets by simply subtracting the coefficients for the main magnet from the coefficients for the gradient magnets on a coefficient-by-coefficient basis, e.g., the a(0,0) coefficient for the main magnet can be subtracted from the a(0.0) coefficients for each of the X, Y, and Z gradient magnets and so forth. This subtraction also automatically incorporates in the lower order coefficients for the gradient magnets information regarding any non-coincident center, axes misalignment, and/or winding error problems that may exist.

(2) The corrected images provided by the invention are in general not completely free of distortions. In particular, those corrected images may still contain some distortions due to non-linearities in the gradient magnets or from other sources in the MR system.

(3) In correcting image distortions in accordance with the foregoing aspects of the invention, it is assumed that any extra shimming that may be required to satisfy field requirements for image generation in an initially shimmed magnet is much smaller than the gross effect of the inhomogeneities, misalignments, and/or winding errors in the gradient fields.

It should also be noted that the image correction techniques set forth above are most effective in correcting image distortions arising from 3D acquisitions using phase encoding in the slice direction. This method does not provide complete distortion correction for 2D acquisitions because during the slice formation, a non-ideal gradient field will influence which spins are excited and whether these spins belong in the slice of interest. Looked at another way, for a 2D acquisition, the methods described above can be considered as correcting in plane distortions, but not the slice selection problem.

As discussed above and illustrated in the examples (see, in particular, the harmonic coefficients of Tables 2A, 2B, and 2C), it has been discovered in accordance with the invention that gradient magnets are characterized by substantial harmonic coefficients corresponding to the X(0,0), X(1,0), Y(0,0), Y(1,0), and/or Z(0,0) field components. That is, actual gradient magnets do not, in general, satisfy the conditions of the "base case" discussed above.

More generally, each of the field generating devices, i.e., the main ($B_0$) magnet and each of the three gradient magnets, has a symmetry point which defines an axis system for the device. In the case of the main magnet, the field is symmetric about the symmetry point, whereas for the gradient magnets it is asymmetric.

For the main magnet, the symmetry point can be considered the center point of the magnet's bore specified by the manufacturer of the main coil (or the main coil bundles). The magnet's bore will typically be considered as lying along the z-axis. This center point is a calculated point and during the wire winding process and/or cooling of the magnet to superconducting temperatures, the calculated symmetry point may move. Nevertheless, for whole body magnets, this method is usually employed. In some cases, the symmetry point for the main magnet is found by measurement, specifically, by plotting the resonance frequency (and thus the field) along the z-axis and taking the spatial mid-point of the resulting plot.

Whatever method is used to determine the symmetry point of the main magnet along the z-axis (hereinafter referred to as "$O_{Bz}$"), the y-axis for the main magnet is then typically considered to be that axis which for a horizontal magnet is in the vertical direction and passes through $O_{Bz}$, while the x-axis is typically that axis which passes through $O_{Bz}$ and is perpendicular to both the z and y axes.

For any one of the gradient magnets, its symmetry point can be co-centered with $O_{Bz}$ by noting that if $O_{Bz}$ and $O_{Gz}$ (for example) are co-centered, then if Gz is energized with current there will be no shift (that is frequency change) of the signal from a small test sample (containing water, say) placed at the coincident symmetry points when the sign of the current in the gradient magnet is reversed in direction.

Because of manufacturing considerations, including tolerances, it is highly unlikely in an MRI system for the four symmetry points $O_{Bz}$, $O_{Gz}$, $O_{Gy}$, $O_{Gx}$ to all be coincident with the origin of the MRI system. This results in a(0,0) and/or b(0,0) terms in harmonic expansions for the field generating devices whose symmetry points do not lie at the origin. In addition, there can be cross terms of the same order, i.e., a(1,0) and/or b(1,0) terms arising from winding/design errors and/or the fact that the x and y axes for the gradient magnets are rotated relative to the overall Cartesian coordinates of the MRI system.

Significantly, in the prior art, these lower order terms were specifically thought to be of no consequence. See U.S. Pat. No. 6,501,273 referred to above.

Thus, in accordance with a seventh aspect, the invention corrects gradient-based distortions in MR images by taking into account, at least to some extent, in the correction process, translational and/or rotational misalignments of the symmetry points and/or associated axes of the field generating devices of the MRI system, i.e., the system's main magnet and its X, Y, and Z gradient magnets, as well as winding and/or design errors in such devices.

Look at another way, this aspect of the invention takes into account the translational and/or rotational misalignment of the symmetry point and/or associated axes of least one of the field generating devices with the symmetry point and/or associated axes of at least one other of the field generating devices. This correction is above and beyond the correction of any basic inhomogeneity in the field generating devices themselves. That is, although the field generating devices in themselves may generate fields which are effectively homogeneous, i.e., a symmetric field in the case of the main magnet or an asymmetric field in the case of a gradient field, there can still be distortions in the resulting images because of translational and/or rotational misalignment of the symmetry points and/or associated axes of the generating devices. The present invention recognizes and addresses this problem so as to produce magnetic resonance images having reduced levels of distortion.

This aspect of the invention is preferably put into practice by, for example, including X(0,0), X(1,0), Y(0,0), Y(1,0), and/or Z(0,0) field components in the harmonic expansions for the fields produced by the gradient magnets and/or the main magnet and then using those harmonic expansions to produce corrected images in accordance with, for example, the first through sixth aspects of the invention. Other approaches for correcting distortions can be used in accordance with this aspect of the invention if desired.

More particularly, harmonic coefficients corresponding to, for example, the X(0,0), X(1,0), Y(0,0), Y(1,0), and/or Z(0,0) field components are determined and are used in correcting MR images. For example, numerical values for these coefficients or numerical values for parameters determined using these coefficients can be stored in a computer memory and then used in correcting the images.

The seventh aspect of the invention can thus be summarized as a method for forming an image of an object using a magnetic resonance imaging system which defines an origin of a coordinate system and comprises (i) a main magnet and (ii) X, Y and Z gradient magnets, said method comprising:

(A) acquiring a magnetic resonance signal data set (the "MR data set") for the object in data space (e.g., a three dimensional or a two dimensional data set) using the X, Y, and Z gradient magnets;

(B) producing an uncorrected image function from the MR data set (preferably using a fast Fourier transform); and (C) producing a corrected image function from the uncorrected image function using at least one coefficient (and preferably, more than one, e.g., at least one of the X-gradient magnet coefficients, at least one of the Y-gradient magnet coefficients, and/or at least one of the Z-gradient magnet coefficients) selected from the group consisting of:

(i) the spherical harmonic coefficients a(0,0), b(0,0), a(1, 0), b(1,0) and b(1,1) for the X-gradient magnet or corresponding coefficients that arise if a basis set other than spherical harmonics is used to solve Laplace's equation;

(ii) the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation; and (iii) the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

The coefficients having the largest magnitudes will have the largest effects in correcting the image, and thus at least those larger coefficients are preferably used in performing the image correction of step (C). Such larger coefficients can be selected by examining a table such as Table 2 for the coefficients with the largest magnitudes and then using those coefficients in step (C), beginning first with the largest 2 or 3 coefficients and continuing on from there as desired. Although using just the largest coefficients will work successfully, in general, using all of the above-listed coefficients is preferred since the additional computation time will, in general, be minimal.

Preferably, one or more (or all) of the above coefficients is stored in a computer memory (or a value derived therefrom is stored in a computer memory) and retrieved from the memory during the production of the corrected image function from the uncorrected image function in step (C).

Additional features and advantages of the invention are set forth in the detailed description which follows, and in part will be readily apparent to those skilled in the art from that description or recognized by practicing the invention as described herein. The accompanying drawings are included to provide a further understanding of the invention, and are incorporated in and constitute a part of this specification. It is to be understood that both the foregoing general description and the following detailed description are merely exemplary of the invention, and are intended to provide an overview or framework for understanding the nature and character of the invention.

IV. BRIEF DESCRIPTION OF THE DRAWINGS

FIG. 3a shows a perfect sphere and FIG. 3b shows the resultant distorted image caused by non-linear gradients having the harmonics of Table 1A.

FIG. 4a shows the three dimensional geometrically distorted image in r=(x,y,z) space and FIG. 3b shows a corrected image in r'=(x',y',z') space. The corrected image is obtained using the harmonics of Table 1A.

FIG. 11a shows the X-gradient field, FIG. 11b shows the Y-gradient field (same as X but 90° rotated), and FIG. 11c shows the Z-gradient field. The values of the coefficients for the dominant harmonics for these field distributions are listed in Table 1A.

FIGS. 12a, 12b, and 12c show the results for the X-gradient, Y-gradient, and Z-gradient, respectively.

Figure 13:
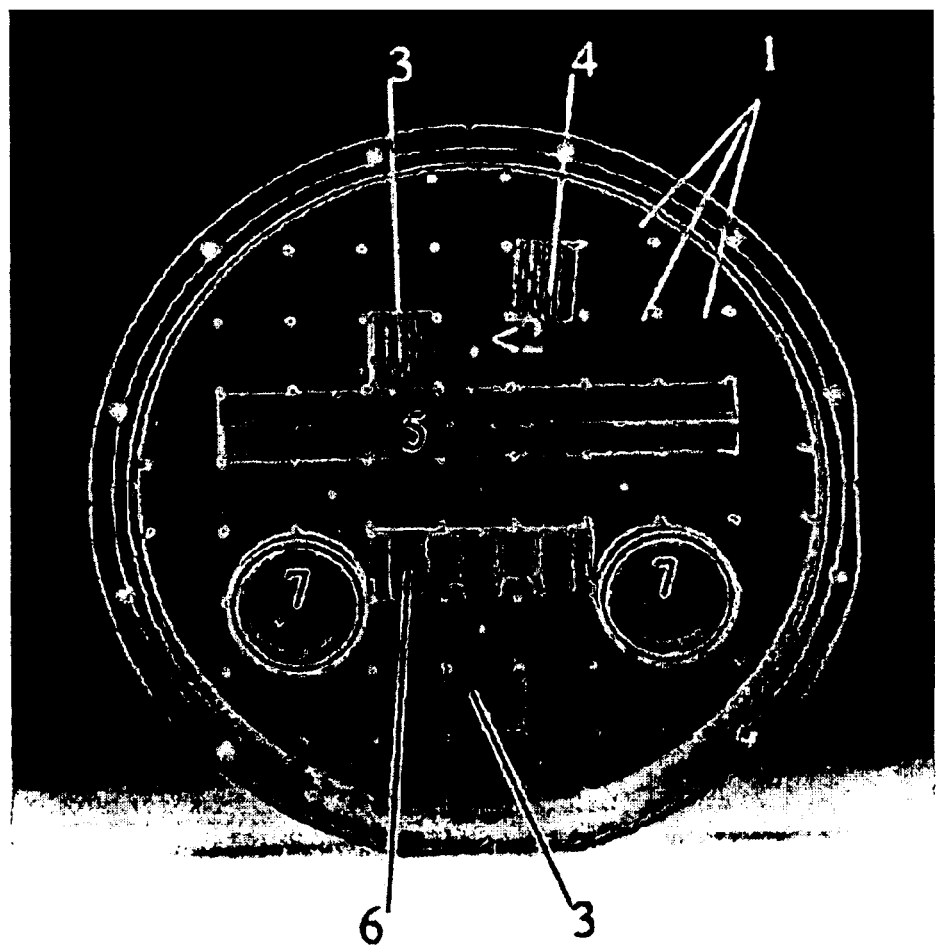

FIG. 13 illustrates a BRUKER quality control assurance phantom. The grid markers are shown at position 1 and can be seen throughout the phantom. The other markers shown by the numbers 2 through 7 are for quality control purposes for other specific pulse sequences.

Figure 14:
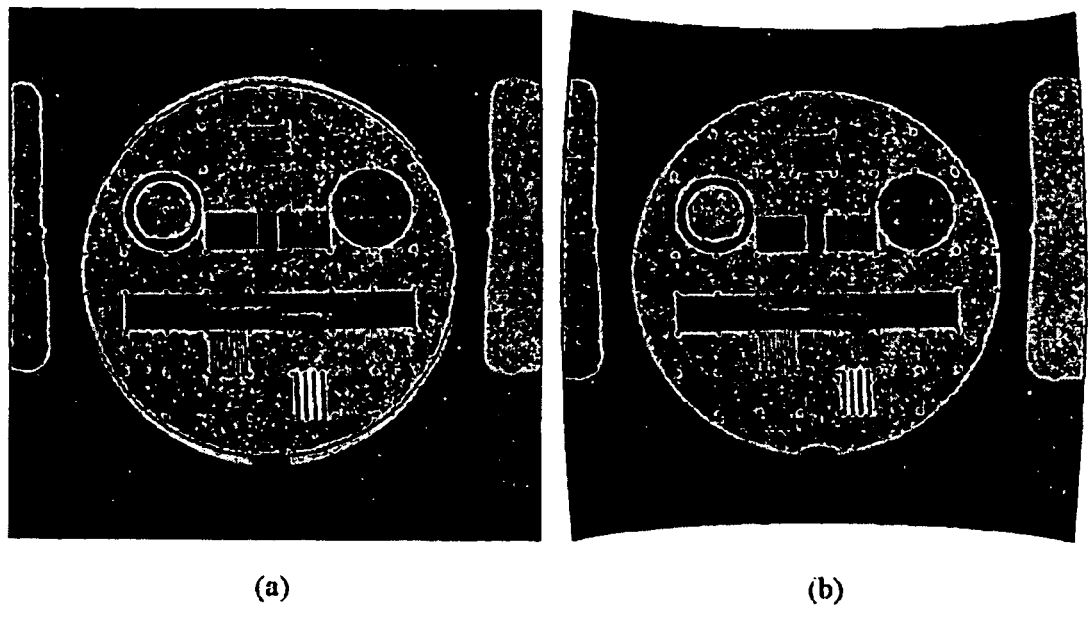

FIG. 14 illustrates the original image (FIG. 14a) of the phantom of FIG. 13 and the corrected image (FIG. 14b) obtained in accordance with the invention, where the phantom's center was at the center of the imaging domain.

Figure 15:
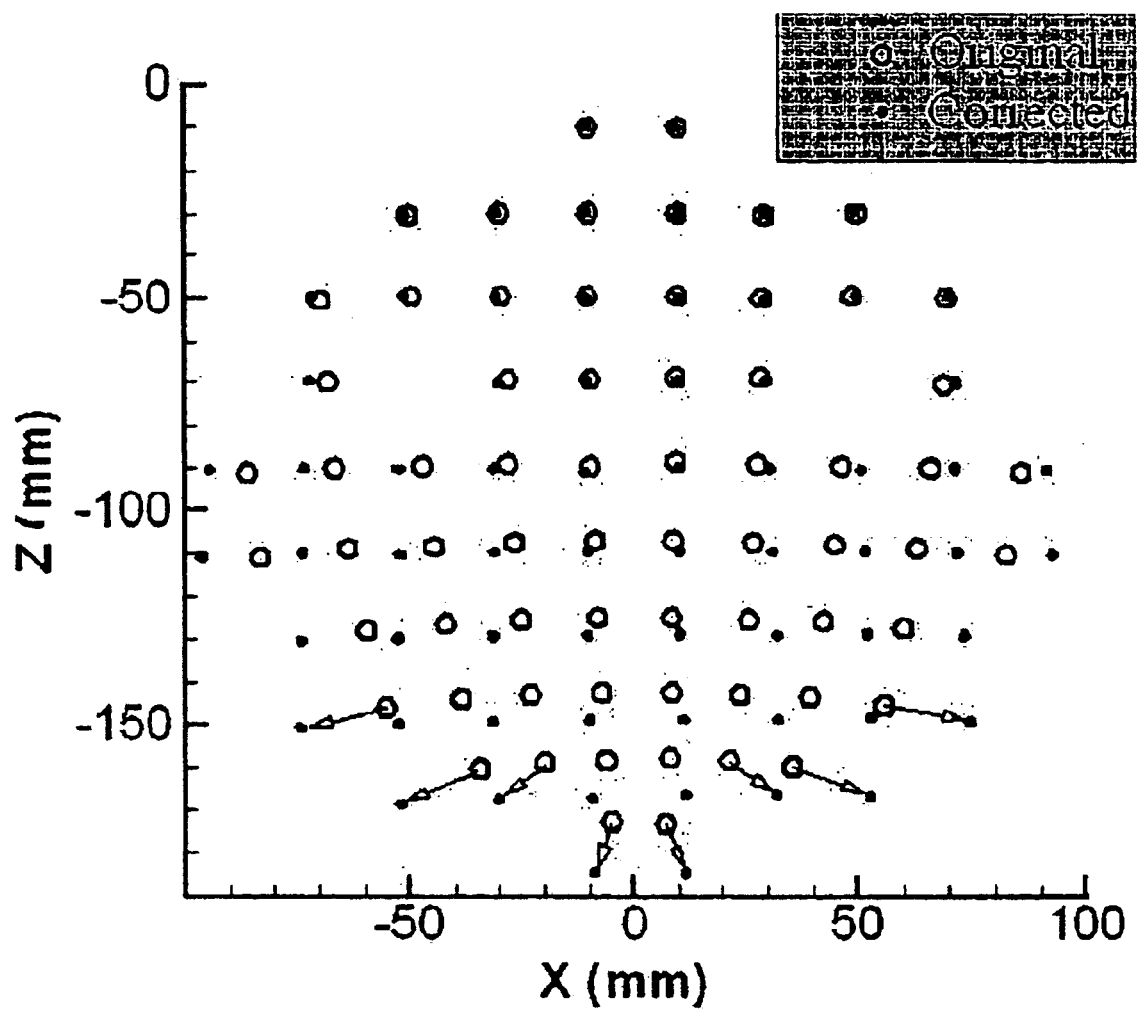

FIG. 15 illustrates the spatial positions of the grid points measured in the XZ plane using the phantom shown in FIG. 13. The open circles are the measured positions while the dots are corrected positions using the harmonic correction method of the invention and the coefficients of Table 1A. The dimensions are in mm.

Figure 16:
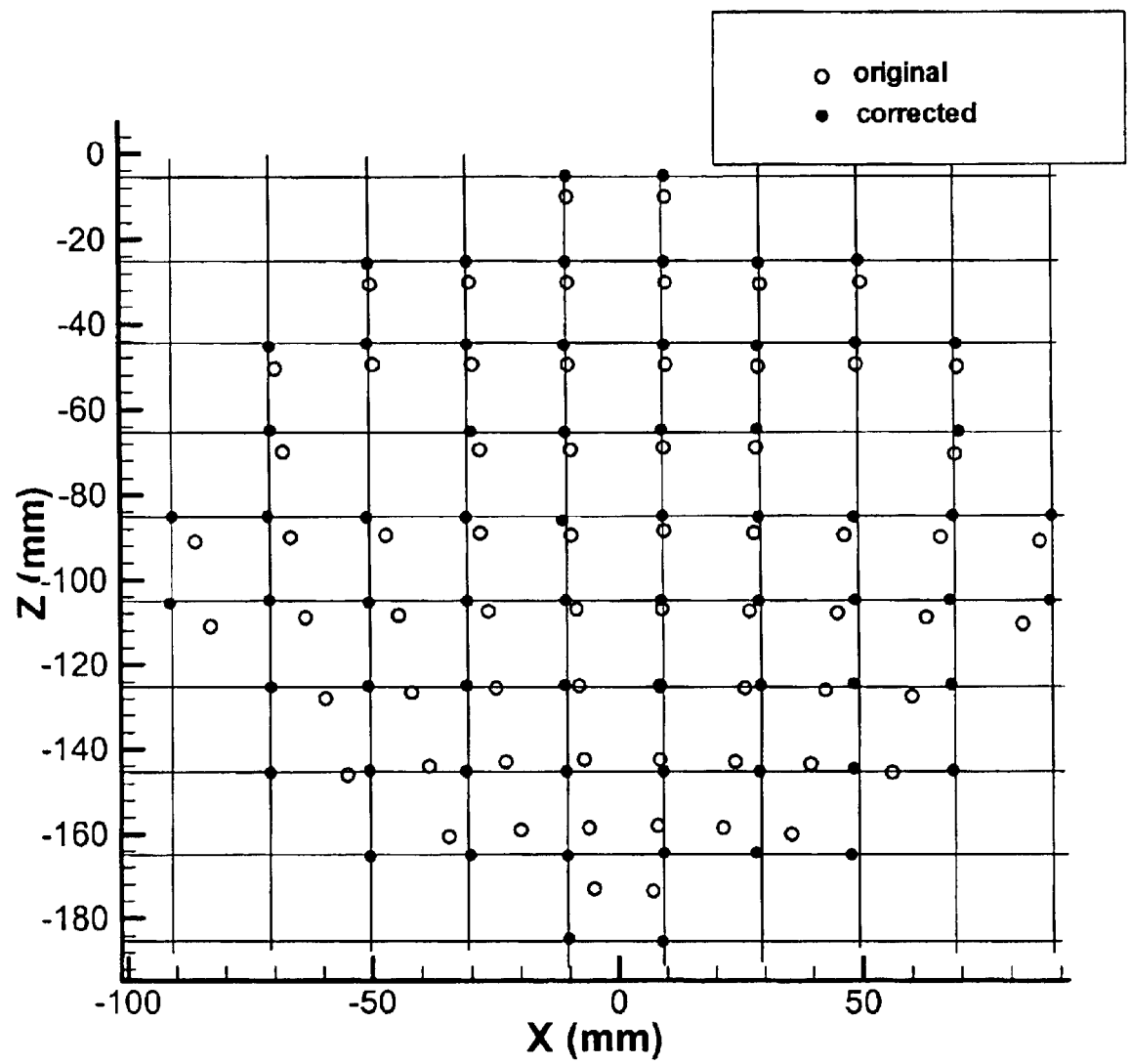

FIG. 16 illustrates the spatial positions of the grid points measured in the XZ plane using the phantom shown in FIG. 13. The open circles are the measured positions while the dots are corrected positions using the harmonic correction method of the invention and the coefficients of Tables 2A, 2B, and 2C. The dimensions are in mm.

V. DETAILED DESCRIPTION OF THE INVENTION

A. Magnetic Resonance Imaging

In magnetic resonance imaging (MRI), the image or image space (r=(x,y,z)) and the data or "k" space (k=($k_x$,$k_y$, $k_z$)) are connected by Fourier transformation. During a pulse sequence, magnetic field gradients play the crucial role of generating k-space coverage. The signal from a single rf excitation of the whole sample in the presence of a set of three orthogonal gradients may be written as the three-dimensional Fourier transform $$s(k) = \int \rho(r) e^{-i2\pi k \cdot r} d^3 r \qquad (1)$$

where s(k) is the signal in k-space and ρ(r) is the spin density in image space. The reconstructed image, $\hat{\rho}(r)$, is the inverse Fourier transform of the measured data, $s_m(k)$ $$\hat{\rho}(r) = \int s_m(k) e^{i2\pi k \cdot r} d^3 k \qquad (2)$$

The three implicitly time dependent components of k are related to the respective gradient-component integrals $$k_x = \gamma \int 'G_x(r,t')dt'$$
$$k_y = \gamma \int 'G_y(r,t')dt'$$
$$k_z = \gamma \int 'G_z(r,t')dt' \qquad (3)$$

where $\gamma$ is a constant and $(G_x, G_y, G_z)$ are the gradient components.

Unless the gradient field is linear, the gradient field is also a function of the non-linear components and thus dependent on the position vector, r=(x,y,z). In standard MR imaging methods, the time domain signals are sampled at a single time rate and k-space is sampled based upon assumed linear gradient fields being applied. Consequently, the image space is encoded as frequency.

If the gradient field is non-linear in the image space, this data acquisition method will result in geometrically distorted images because the frequency encoding is non-linear. That is, the non-linear gradient field distribution is directly mapped into the image resulting in distortion. Knowing the exact gradient field profiles is thus central to solving this geometric image distortion problem.

B. Describing the Gradient Field Distribution

Accurately describing the gradient field distribution is not a simple task. Even for the same design of gradient coil, winding errors may induce variation from the predicted field.

As discussed above, the optimum method is to measure the actual field strength produced by the particular gradient coil set at a finite number of points in the image space. A function can be then constructed to describe accurately the field distribution.

In general, any base function (for example, spherical harmonics, cylindrical harmonics, elliptical harmonics, etc) that satisfies Laplace's equation $\nabla^2 B_x = 0$ can be used. In particular, such functions can be used to express $B_x$ in the form:

$$B_x(x_1, x_2, x_3) = \sum_i c_i \beta_i(x_1, x_2, x_3),$$

where $(x_1, x_2, x_3)$ is a particular coordinate system, β is the bases of the function that satisfies Laplace's equation, and c is the coefficient generated in the expansion.

The preferred approach is to expand the field using spherical harmonics as the basis function. See Eccles C D, Crozier S, Westphal M, Doddrell D M. Temporal spherical-harmonic expansion and compensation of eddy-current fields produced by gradient pulses. Journal of Magnetic Resonance, A 103: 135–141, 1993.

The field $B_Z$ generated by a gradient coil can be written in spherical coordinates as:

$$B_{V(n,m)}(r,\theta,\phi) = r^n [a_{V(n,m)} \cos(m\phi) + b_{V(n,m)} \sin(m\phi)] P_{(n,m)}(\cos\theta) \qquad (4)$$

where $B_{V(n,m)}(r,\theta,\phi)$ is a spherical harmonics expansion of order n and degree m of the particular $B_Z$ gradient field (V=X, Y, and Z, for the x, y, and z gradient fields, respectively), $a_{V(n,m)}$ and $b_{V(n,m)}$ are the spherical harmonic coefficients, $P_{(n,m)}(\cos\theta)$ are the associated Legendre functions, and r is the radial distance from the origin of the MRI system. With a finite number of terms, the summation of the equation (4) is only an approximation of the true gradient field Bz.

Figure 1A:
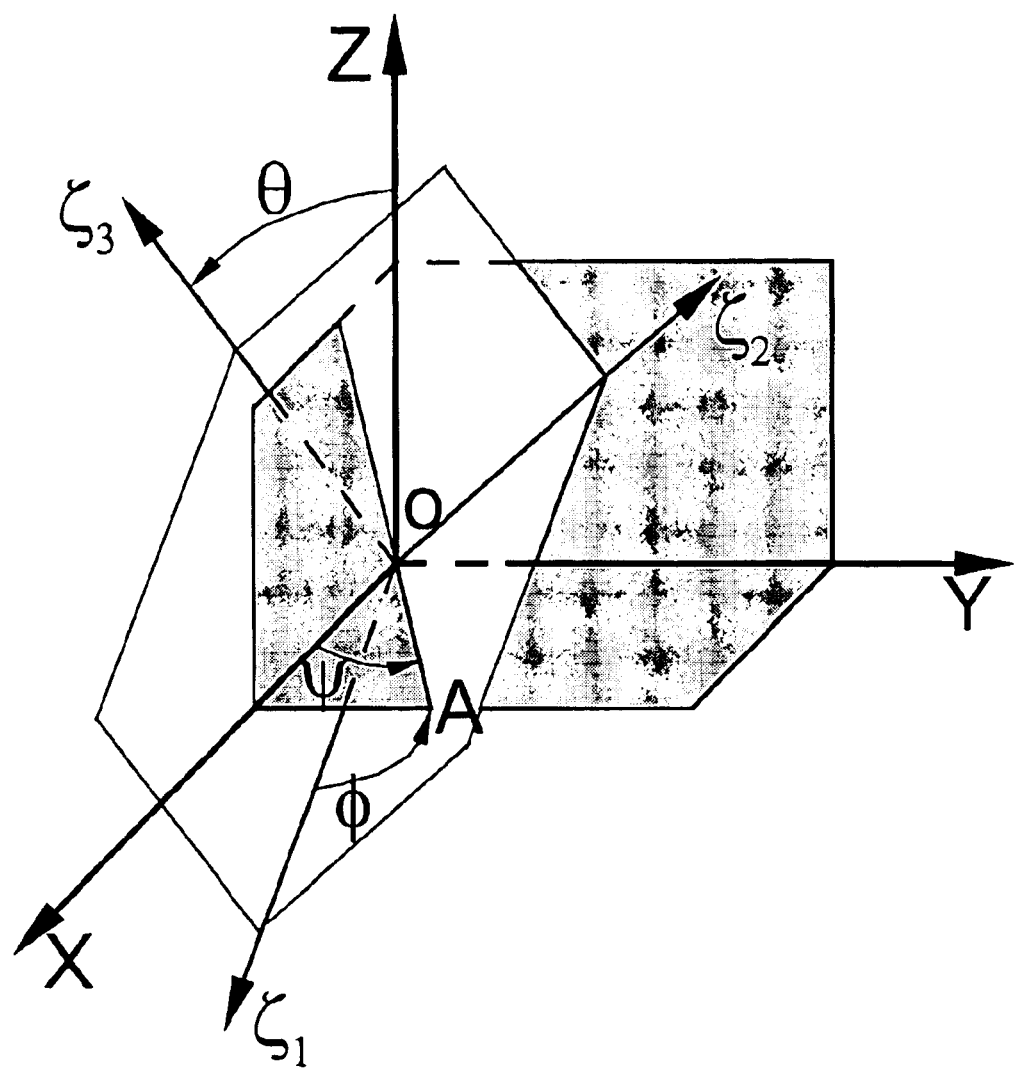
FIG. 1A is a schematic drawing showing a representative coordinate system for describing arbitrarily-oriented 3D imaging.
Figure 1B:
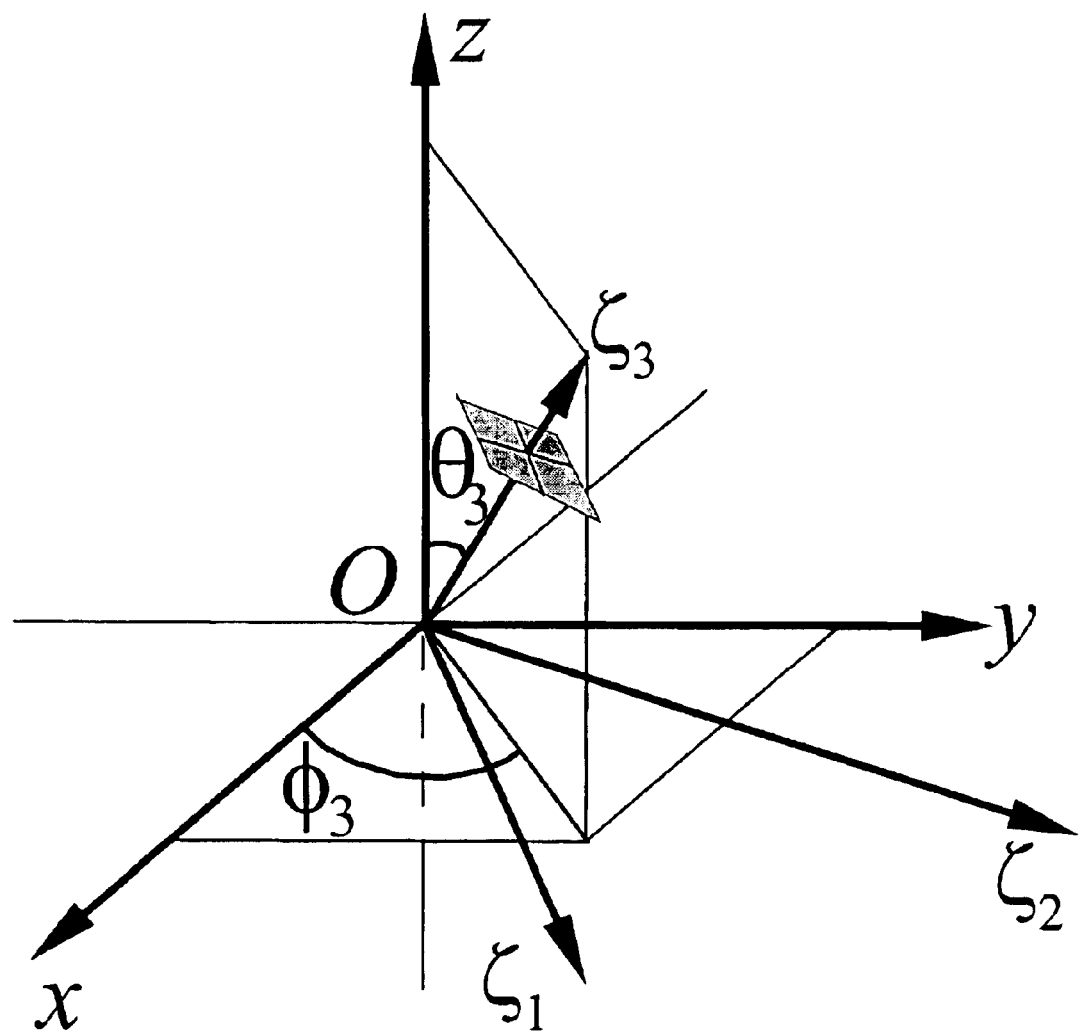
FIG. 1B is a schematic drawing showing a representative coordinate system for describing the spatial orientation of an oblique slice.
Figure 2A:
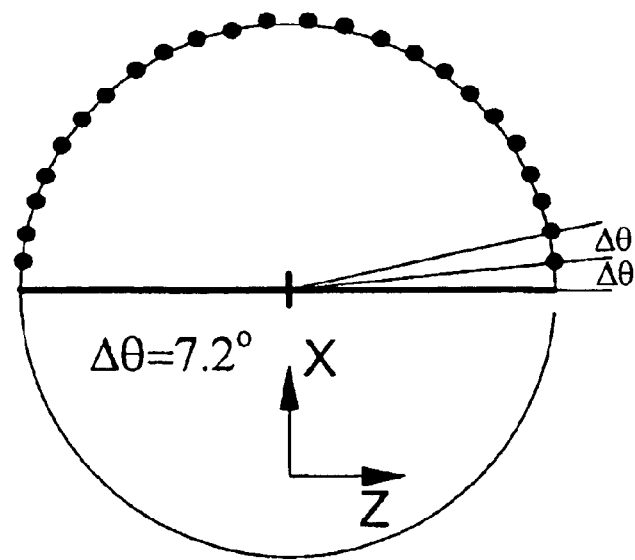
FIG. 2A illustrates representative sample positions for 24 longitudinal planes and FIG. 2B shows representative azimuthal rotations. The dots in these figures are the field measurement positions.
Figure 2B:
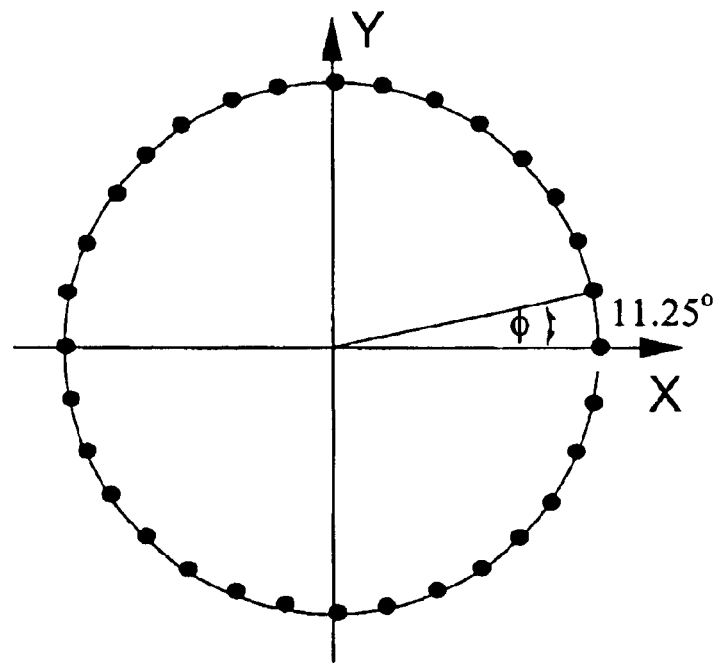

The methodology for using spherical harmonics deconvolution to describe magnetic field impurities has been previously described in the Eccles et al. reference cited above. In general, a multi-plane sampling of the DSV (diameter spherical volume) is performed in order to ensure over-sampling and accurate estimation of the required gradient impurities. Magnets are usually mapped with up to 24 planes yielding harmonics to 23rd order. Depending on the gradient set and the design parameters employed, gradient impurities can extend to 7th order requiring at least an 8-plane plot. FIGS. 2A and 2B illustrate suitable field measurement positions for mapping main magnet and gradient fields.

Figure 2C:
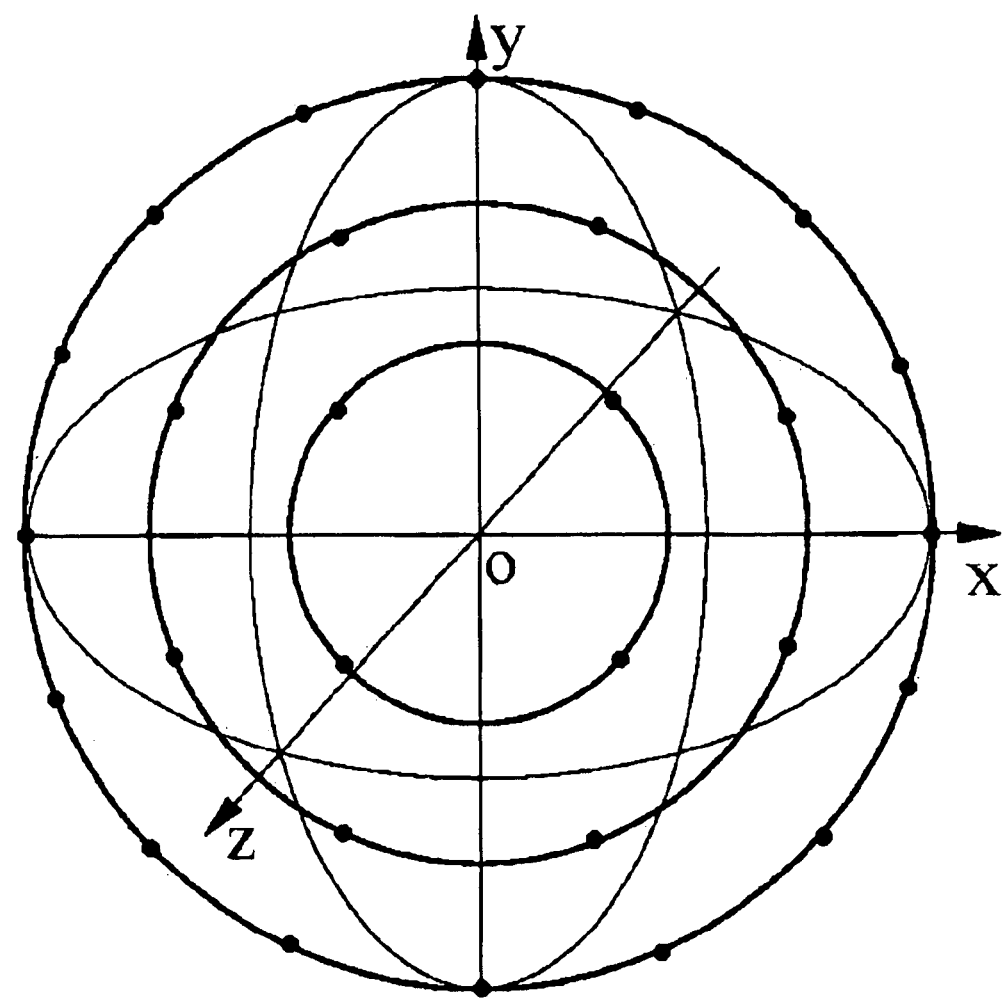
FIG. 2C illustrates sample positions employed for optimal spherical harmonic analysis of the gradient field if the deconvolution is performed to lower order than 8. The dots in the figure show the sample positions.

It is convenient to approximate the distribution of the gradient field over the imaging volume such that the maximum error in the approximate gradient field is below a predetermined value (see below). If the deconvolution is performed to lower order than 8, it is more accurate to sample the image volume as shown in FIG. 2C, where the dots represent sample points.

A non-linear best fitting method can be used to solve for the coefficients $a_{V(n,m)}$ and $b_{V(n,m)}$, ensuring that the reproduced field $\tilde{B}_X$ and the true field $B_X$ have a relationship $$|\tilde{B}_X(r) - B_X(r)|_{max} \leq \epsilon, \quad r \in D_{dsv}$$

where $D_{dsv}$ represents a domain of the dsv that covers the image space and ε is an error parameter that preferably is less than 5%. Note that here, dsv refers to the diameter spherical volume of the gradient, not the main magnetic field.

As mentioned above, even for the same design of a gradient coil, winding errors will induce variation from the predicted field so that as a general proposition, it will be, at least to some extent, inaccurate to simply use a theoretical field expansion based on the winding patterns of the gradient coils to correct image distortion. Nevertheless, if desired, the present invention can be practiced with a theoretical field expansion. However, the preferred approach is to measure the actual field strengths produced by a particular gradient coil set at a finite number of points in the image space and then, using this sampling, to construct a function, specifically, a spherical harmonic expansion, that accurately describes the measured field distribution.

C. Gradient Field, Image Space, and K-Space

Once knowledge of the gradient field $B_X(r)$ is established, the gradient can be defined as $$G_\upsilon(r) \equiv \frac{\partial Bz_\upsilon(r)}{\partial \upsilon} \equiv \frac{\partial Bz_\upsilon^L(\upsilon)}{\partial \upsilon} + \frac{\partial Bz_\upsilon^N(r)}{\partial \upsilon} \equiv G_\upsilon^L + G_\upsilon^N(r) \qquad (5)$$

where υ∈(x,y,z), $Bz_\upsilon$ is total gradient field that is generated by a particular coil component, $Bz_\upsilon^L$ is the linear gradient field that has only the desired first order harmonic for the Cartesian coordinate υ, $Bz_\upsilon^N$ is the non-linear gradient field defined by the higher order harmonics, $G_\upsilon(r)$ represents a particular gradient component, $G_\upsilon^L$ is a constant that represents the linear gradient generated by current in the coil, and $G_\upsilon^N(r)$ is a function of the spatial function that represents the non-linear contribution to the gradient field. It is not possible experimentally to generate a perfectly linear gradient in the free space, therefore, $G_\upsilon^N$ always exists.

During the MR acquisition, the actually time dependent gradient can be present as:

$$G_\upsilon(r)\xi_\upsilon(t) = [G_\upsilon^L + G_\upsilon^N(r)]\xi_\upsilon(t) \quad (6)$$

where $\xi_\upsilon(t)$ is a function of the time that controls all the gradient component activity, including the gradient pulse sequence time length, gradient switching, and increments of any phase encoding gradient strength. The set $\{\xi_x(t), \xi_y(t), \xi_z(t)\}$ leads to a completed coverage of k-space. In equation (6), it is important to note that non-linear gradients behavior is independent of the $\xi_\upsilon(t)$, which means the geometric image distortion is the same, i.e., constant, no matter how the k-space is covered (sampled). This is covered in more detail in the Appendix set forth below, which analyzes the effect of incrementing a phase encoding gradient to sample a particular direction in k-space.

The gradient field produced by a gradient coil can be expressed in terms of its linear and non-linear gradients as:

$$B_x^\upsilon(r) = (\upsilon + \eta_\upsilon(r))G_\upsilon^L, \text{ where } \eta_\upsilon(r) = \frac{Bz_\upsilon^N(r)}{G_\upsilon^L} \quad (7)$$

The Larmor frequency of spins precessing in such a magnetic field is:

$$\omega_G(r,t) = \gamma[(x+\eta x(r))G_x^L\xi_x(t) + (y+\eta_y(r))G_y^L\xi_y(t) + (z+\eta_z(r))G_z^L\xi_z(t)] \quad (8)$$

Equation (8) links the position of spins at a particular location along some direction and their rates of precession at that location in space. Such a linkage is known as frequency encoding along the particular direction.

Equations (1) and (2) then become:

$$s(k) = \int \rho(r') e^{-i2\pi k \cdot r'} d^3 r', \quad (9)$$

$$\hat{\rho}(r') = \int s_m(k) e^{i2\pi k \cdot r'} d^3 k \quad (10)$$

where $$r' = (x', y', z') = \{[x+\eta_x(r)], [y+\eta_y(r)], [z+\eta_z(r)]\} \quad (11)$$

Therefore, when non-linear gradients are used to sample k-space, the actual image space is $r'=(x',y',z')$, not $r=(x,y,z)$, and the k-space sampling should be represented by the vector $k'=(k_x',k_y',k_z')$ not $k=(k_x,k_y,k_z)$ where:

$$k' = (k_x', k_y', k_z') \quad (12)$$

$$= \left\{ \left[ k_x \frac{(1+\eta_x(r))}{x} \right], \left[ k_y \frac{(1+\eta_y(r))}{y} \right], \left[ k_x \frac{(1+\eta_x(r))}{z} \right] \right\}$$

Equations (11) and (12) are the relations between linear sampling of k-space and non-linear sampling. A geometrically distorted image can thus be corrected in the image space by using the relationship in equation (11).

D. Correcting the Distorted Image

Based on the foregoing, a number of approaches can be used for image distortion compensation in accordance with the invention. In each approach, the time domain data is transformed using a linear transformation, specifically, a fast Fourier transform. Literature references to fast Fourier transform techniques include O. E. Brigham. The Fast Fourier Transform. Prentice-Hall, Englewood Cliffs, N. J., 1974 and Nussbaumer, H. J. 1982, fast Fourier Transform and Convolution Algorithms (New York: Springer-Verlag), the contents of which are incorporated herein by reference.

In what may be considered a primary approach for performing image distortion compensation, instead of using equation (11) directly, the transformation to the undistorted image space is performed by solving a system of nonlinear equations:

$$B_x(r') = B_x^L(r) \quad (13)$$

where $B_x(r') = [B_x^x(r'), B_x^y(r'), B_x^z(r')]^T$ and $B_x^L(r) = [xG_x^L, yG_y^L, zG_z^L]^T$.

For a given image point having directional vector r, equation (13) will yield a new image point r'. The geometric distorted image is corrected by using the new image space $r'=(x',y',z')$.

Figure 3:
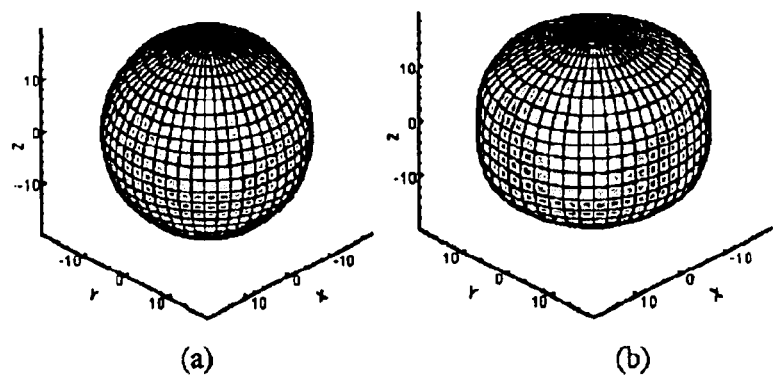
FIG. 3 illustrates a three dimensional geometrically distorted image, where
Figure 4:
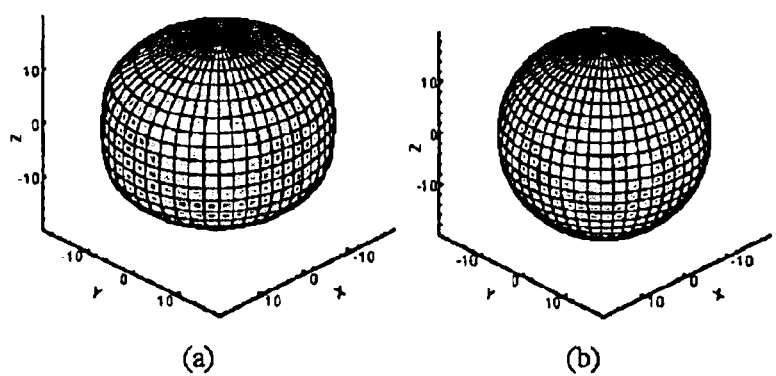
FIG. 4 illustrates transformation of image space to correct a distorted image, where

FIGS. 3 and 4 illustrate the process. FIG. 3a shows a spherical object which is to be imaged, and FIG. 3b shows the distorted image obtained as a result of the use of gradient magnets that produce non-linear gradients. FIG. 4a is the distorted image of FIG. 3b and FIG. 4b shows the corrected image obtained using the new image space $r'=(x',y',z')$.

The set of equations (13) can be written out as:

$$\begin{cases} B_z^x(r', \theta', \phi') = xG_x^L \\ B_z^y(r', \theta', \phi') = yG_y^L \\ B_z^x(r', \theta', \phi') = zG_z^L \end{cases} \quad (13A)$$

where $\{B_x^x(r',\theta',\phi'), B_x^y(r',\theta',\phi'), B_x^z(r',\theta',\phi')\}$ have their harmonic expansion. Therefore, $(r',\theta',\phi')$ can be find by solving the nonlinear equation (13A). Then the coordinates of $(r', \theta',\phi')$ can be transformed to $(x',y',z')$ using $$\begin{cases} x' = r'\sin\theta' \cos\phi' \\ y' = r'\sin\theta' \sin\phi' \\ z' = r'\cos\theta' \end{cases}$$

For a particular time dependent gradient scheme, $\xi(t)$, to sample k-space, equation (13) becomes:

$$B_x(r') \cdot \xi(t) = B_x^L(r) \cdot \xi(t) \quad (14)$$

This can always be rewritten in the same form as equation (13). Equation (14) shows that the geometric distortion of the image is independent of the temporal manner in which k-space coverage is generated (see the Appendix set forth below). Therefore, the distortion behavior only depends on the gradient coil set themselves. Once the gradient field is established, the correction of an image can be always obtained.

E. Origin of the MRI System

As well known in the art, an MRI system contains the following three major hardware components:

(1) A main magnet which generates a $B_0$ magnetic field with its field vector oriented in what is commonly designated the z direction.

(2) Orthogonal gradient magnets which consist of an X-gradient magnet, a Y-gradient magnet and a Z-gradient magnet, which generate, respectively, magnetic fields $B_X$, $B_Y$ and $B_Z$. These vector magnetic fields are all in the z direction, and are intended to produce the gradients $G_X = \partial B_X/\partial x$, $G_Y = \partial B_Y/\partial y$ and $G_Z = \partial B_Z/\partial z$, respectively.

(3) An RF coil, which generates a $B_1$ magnetic field with the field vector for this field being perpendicular to the z direction.

As discussed above, the present invention is concerned with $B_0$ and $G_X$, $G_Y$ and $G_Z$.

In the design of an MRI system, the main magnet is designed on its own. The useful $B_0$ field region is referred to in the art as the Diameter Sensitive Volume (DSV) or Volume of Interested (VOI) and has its own defined center (origin), say $O_0$.

The X, Y, and Z gradient magnets are designed separately from one another and from the main magnet. In the design process, accommodations need to be made so that these magnets will spatially fit with one another in the finished MRI system. Their DSV's or VOI's also have their own centers (origins), say $O_X$, $O_Y$, and $O_Z$, respectively.

In the manufacturing process, the main magnet is normally fabricated on its own. The X, Y, and Z gradient magnets are typically fabricated together as one unit. However, due to engineering limitations, the centers $O_X$, $O_Y$, $O_Z$ of the magnets essentially never coincide on a single center point $O_G$ nor are the gradient field generating devices pure.

When the gradient magnets are fitted into the main magnet, the engineering process is likely to use the center of one of the gradient magnets as a reference center (say $O_X$). The difference between this center and the main magnet center $O_0$ is then minimized during the assembly process.

Every MRI system has a fixed center (origin) of the image region, say $O_I$. In the system, all the imaging software has its coordinate reference center (origin) set at $O_I$, and all the image data is given at coordinate positions (x, y, z) with respect to the origin $O_I$. In this application and in the claims, the origin defined by the MRI system is preferably $O_I$.

$O_I$ can be the same point as $O_0$, or $O_I$ and $O_0$ can be separated by a small difference. However, because $O_0$ and each of $O_X$, $O_Y$, $O_Z$ are essentially never coincident, the full set of centers, i.e., $O_I$, $O_0$, $O_X$, $O_Y$ and $O_Z$, are essentially never at the same point.

Moreover, in the real world, it is very hard to find the exact locations of $O_0$, $O_X$, $O_Y$ and $O_Z$. Many factors effect the center positions. For example, in the main magnet design, $O_0$ will be the field symmetry point. However, after magnet installation, there are environment effects and passive shimming effects. These effects are very unlikely to be symmetric. So, a perfect 3 dimensional symmetry point of a real $B_0$ field many never be found.

When mapping the main and gradient fields, the center, $O_C$, of the field camera is preferably in a position as close to the center $O_I$ of the image region as possible. Also, $O_C$ should not be changed between the individual field plots. The harmonic coefficients obtained from such a field plot analysis give a true measure of the effects of non-linearities in the gradient magnet's fields (geometrical distortion in an image).

In view of these considerations, whether $O_I$, $O_0$, $O_X$, $O_Y$ and $O_Z$ are at the same point or not, or whether the gradient field generating devices are completely pure, or whether the gradient field axes are perfectly aligned with the system's and main magnet's axes, are not problems, as long as the field plot measurements are all referenced to the same origin, i.e., $O_C$. Because the MR images are referenced to $O_I$, for a true field representation, $O_C$ should be the same point as $O_I$. As MRI systems provide a laser marker and a data display showing the position of the marker, $O_I$ is easy to find and the center $O_C$ of the field camera can be readily aligned with $O_I$.

As discussed fully above, in accordance with the present invention, all the imaging distorting effects of the gradient magnets are preferably taken into account. Therefore, in the preferred embodiments of the invention, corrections involving not only high order terms or harmonics to deal with non-linear gradient field effects are included in the correction process, but also low order terms or harmonics ($a_{0,0}$, $b_{1,0}$, etc.), which relate to $O_0$, $O_X$, $O_Y$ and $O_Z$ not being coincident, as well as to rotational misalignments of the field generating devices and/or winding/design errors in those devices.

The above considerations regarding the origin of an MRI system apply to both symmetrical and non-symmetrical systems.

VI. DESCRIPTION OF PREFERRED EMBODIMENTS

FIGS. 5–10 illustrate preferred procedures for correcting distorted MR images in accordance with the invention.

Figure 5:
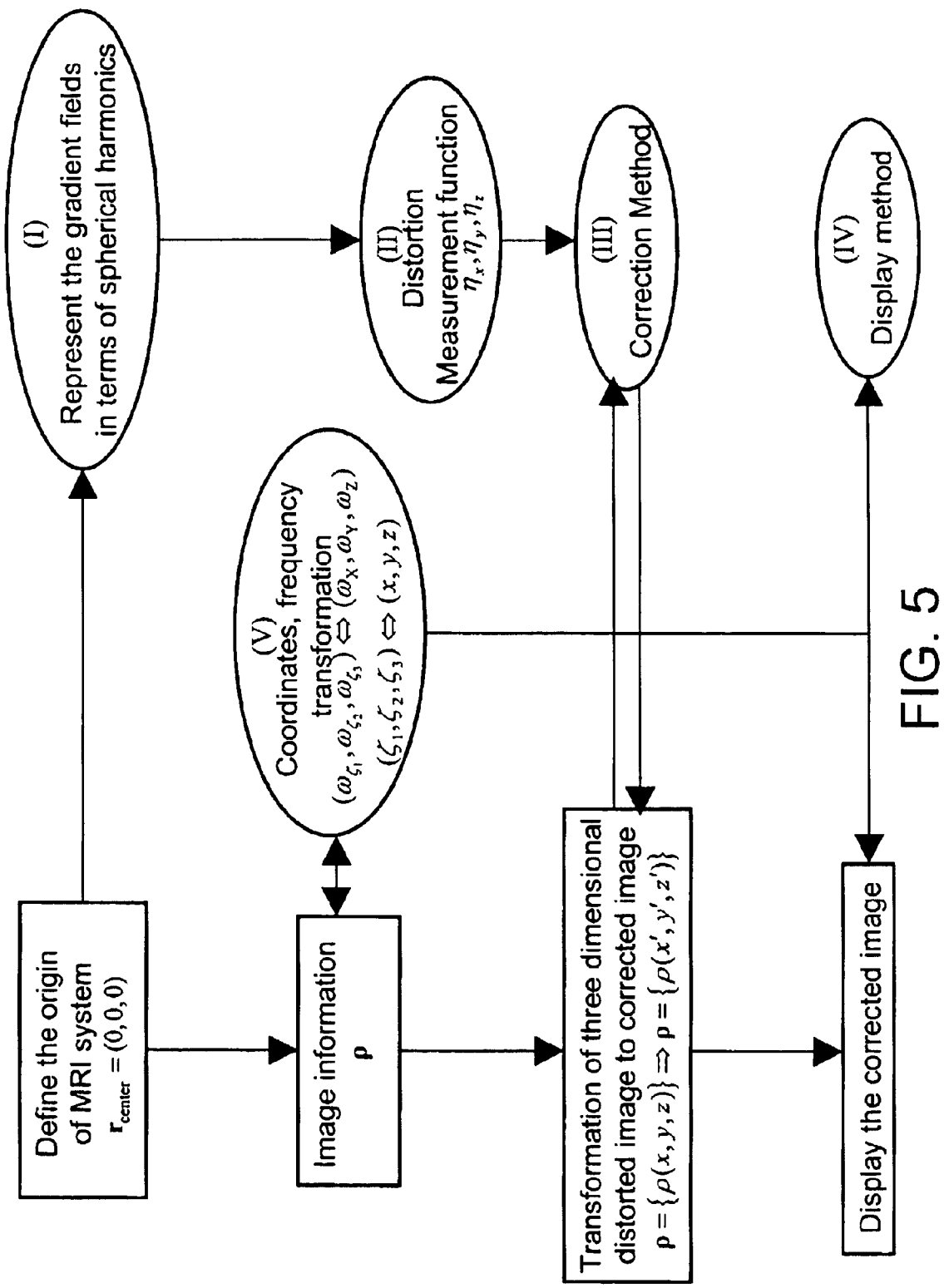
FIG. 5 is a general flow chart illustrating the overall process of the invention from determination of the non-linearity of the gradient fields to displaying corrected MR images.
Figure 6:
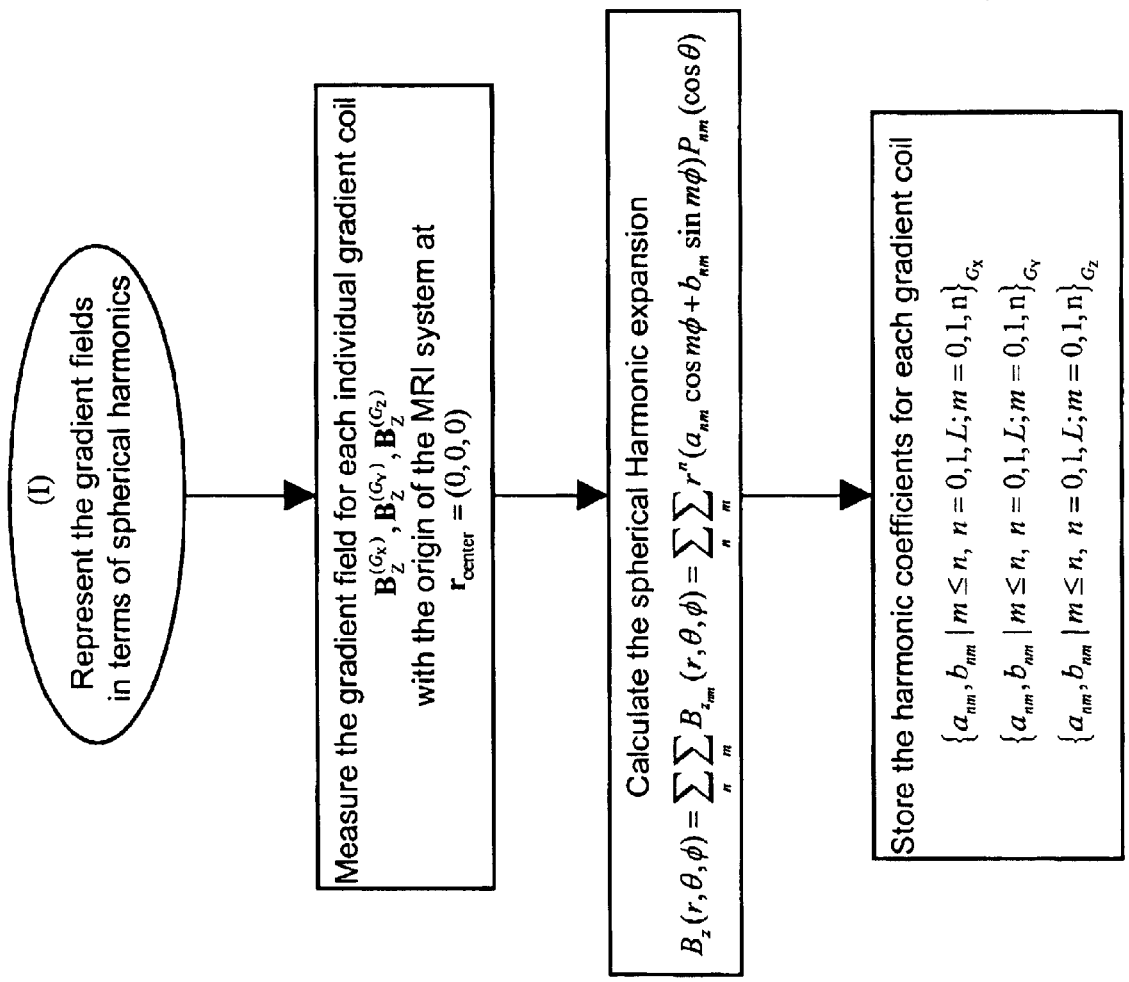
FIG. 6 is a more specific flow chart illustrating the step of determining the non-linearity of the gradient fields in terms of a spherical harmonic expansion.
Figure 7:
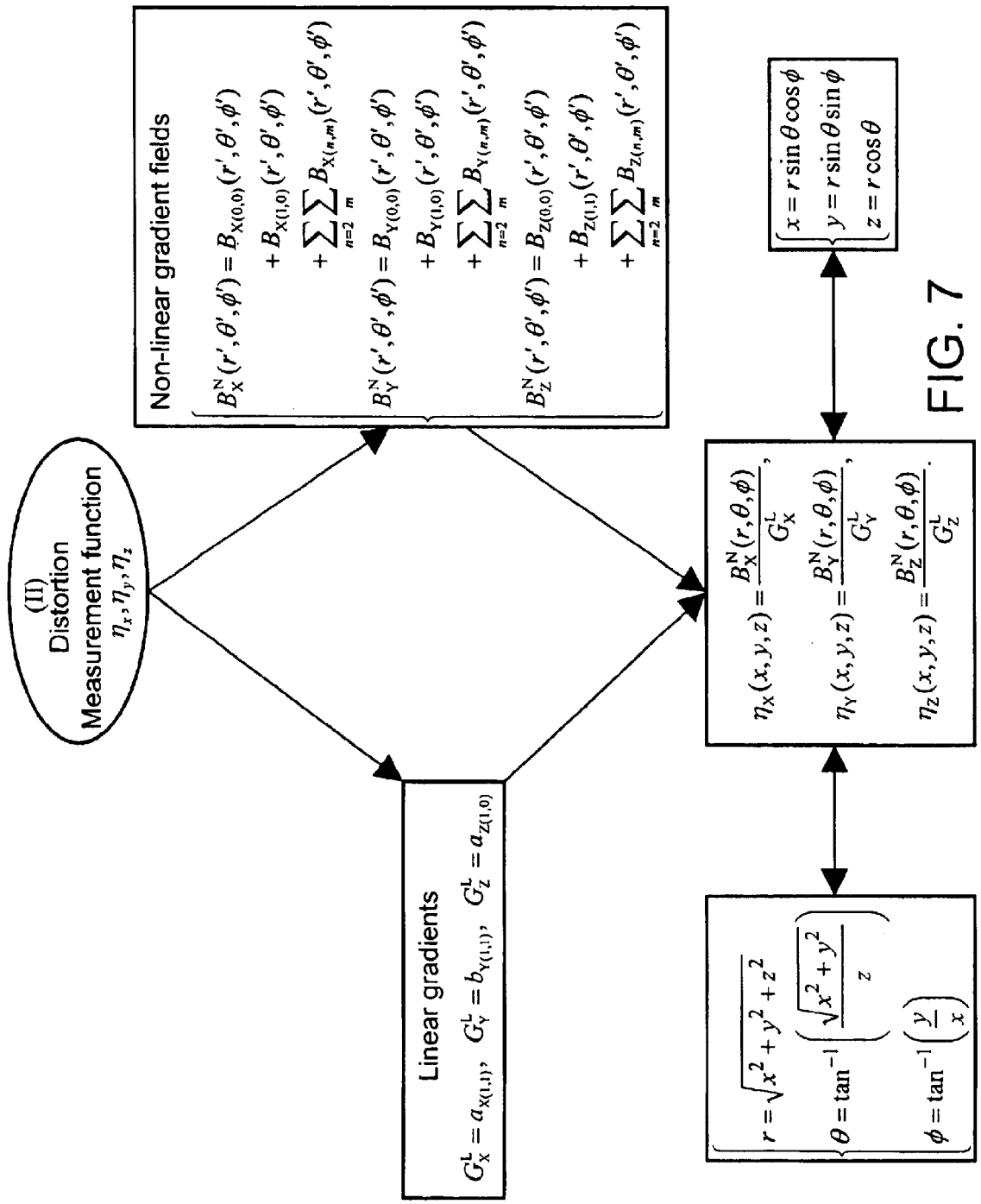
FIG. 7 is a more specific flow chart illustrating a preferred approach for representing the linear and non-linear components of the gradient fields.
Figure 9:
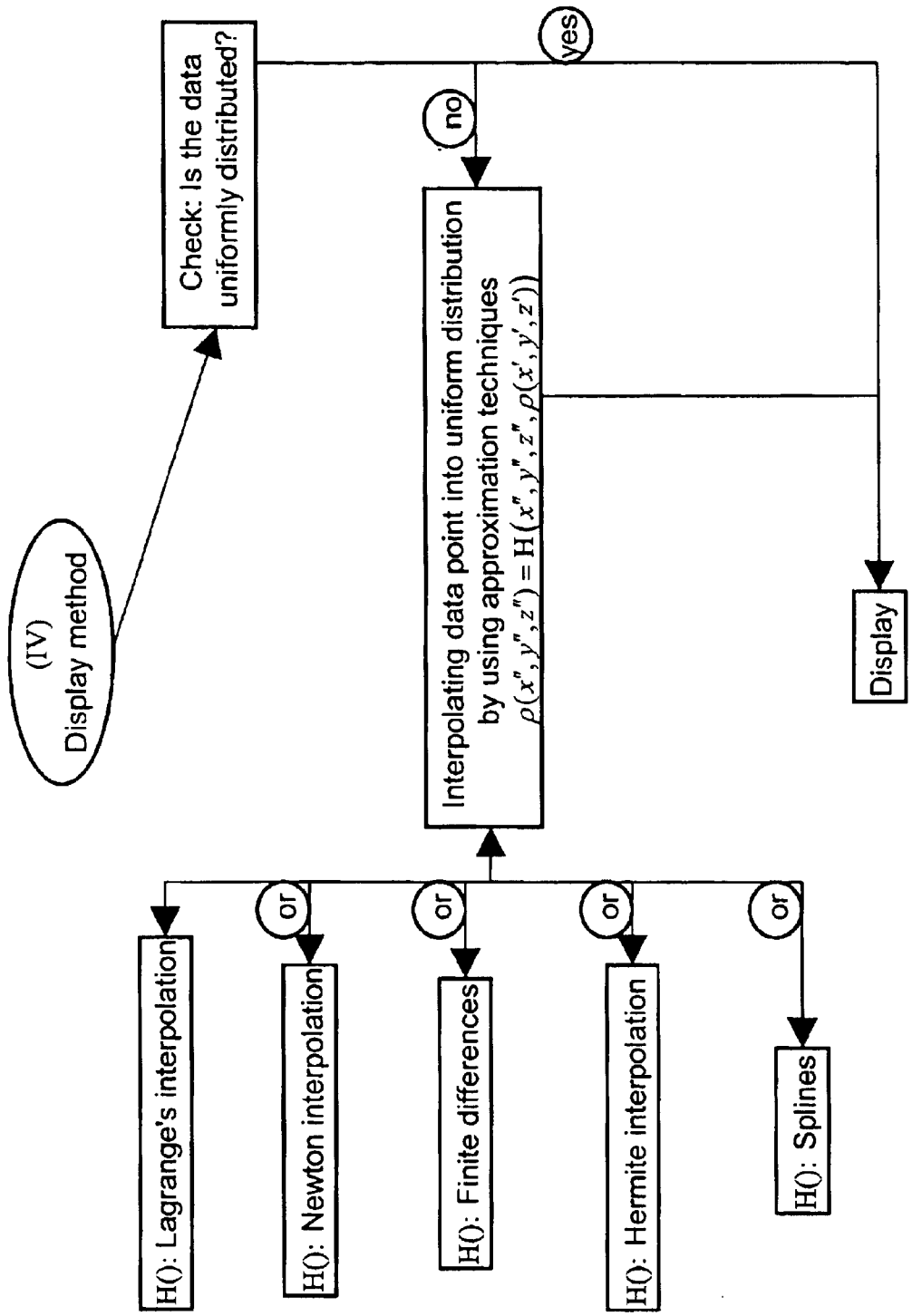
FIG. 9 is a more specific flow chart illustrating preferred approaches for displaying corrected images where the corrected data points are not uniformly distributed.
Figure 10:
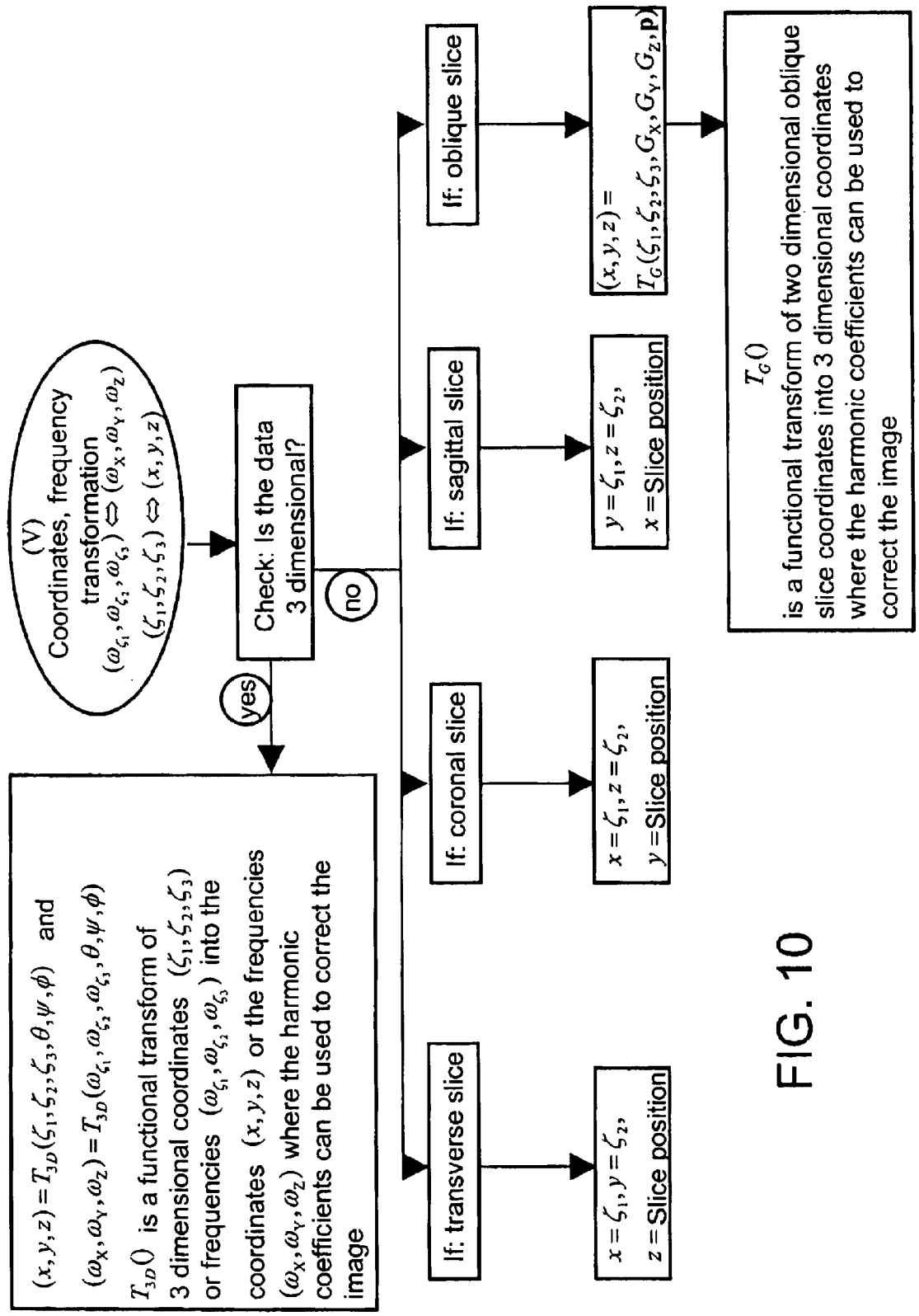
FIG. 10 is a more specific flowchart illustrating variations of the method when applied to (i) the correction of slice, including oblique slice, images, and (ii) arbitrarily-oriented 3D images.

FIG. 5 is a general flow chart illustrating the overall process of the invention from determination of the non-linearity of the gradient fields (Step (I) in FIG. 5) to displaying corrected MR images (Step (IV) in FIG. 5). FIGS. 6–9 illustrate, respectively, Steps (I) through (IV) of FIG. 5 in more detail, while FIG. 10 shows variations of the method for two dimensional data (see Step (V) in FIG. 5; see also the fourth through sixth aspects of the invention discussed above) and arbitrarily-oriented 3D imaging (see again Step (V) in FIG. 5; see also the first through third aspects of the invention discussed above). The following discussion sets forth the mathematical nomenclature used in these figures.

With reference to equation (5) above (see also FIG. 6), the linear and non-linear components of the gradient field are respectively given by the following equations (15) and (16), where for convenience, as in various of the equations set forth above, the subscript z has been dropped from $B_z$:

$$(G_X^L = a_{X(1,1)}, \ G_Y^L = b_{Y(1,1)}, \ G_Z^L = a_{Z(1,0)}) \qquad (15)$$

and $$\begin{cases} B_X^N(r', \theta', \phi') = B_{X(0,0)}(r', \theta', \phi') + \\ \quad B_{X(1,0)}(r', \theta', \phi') + \sum_{n=2}\sum_{m} B_{X(n,m)}(r', \theta', \phi') \\ B_Y^N(r', \theta', \phi') = B_{Y(0,0)}(r', \theta', \phi') + \\ \quad B_{Y(1,0)}(r', \theta', \phi') + \sum_{n=2}\sum_{m} B_{Y(n,m)}(r', \theta', \phi') \\ B_Z^N(r', \theta', \phi') = B_{Z(0,0)}(r', \theta', \phi') + \\ \quad B_{Z(1,1)}(r', \theta', \phi') + \sum_{n=2}\sum_{m} B_{Z(n,m)}(r', \theta', \phi') \end{cases} \qquad (16)$$

For the base case, the magnitudes of the X(0,0), X(1,0), Y(0,0), Y(1,0), and Z(0,0) field components are zero or effectively zero.

From here, it is useful to define the following terms (see FIG. 7):

$$\begin{cases} \eta_X(x, y, z) = \dfrac{B_X^N(r, \theta, \phi)}{G_X^L} \\ \eta_Y(x, y, z) = \dfrac{B_Y^N(r, \theta, \phi)}{G_Y^L} \\ \eta_Z(x, y, z) = \dfrac{B_Z^N(r, \theta, \phi)}{G_Z^L} \end{cases} \qquad (17)$$

where

-continued $$\begin{cases} r = \sqrt{x^2+y^2+z^2} \\ \theta = \tan^{-1}\left(\frac{\sqrt{x^2+y^2}}{z}\right) \\ \phi = \tan^{-1}\left(\frac{y}{x}\right) \end{cases} \quad (18)$$

Correction of image distortion can now be simply written as:

$$\rho(x',y',z') = \rho(x,y,z) \quad (19)$$

where $$\begin{cases} x' = x - \eta_X(x',y',z') \\ y' = y - \eta_Y(x',y',z') \\ z' = z - \eta_Z(x',y',z') \end{cases} \quad (20)$$

Equation (20) can be solved iteratively for (x',y',z') via the following process (see FIG. 8 and, in particular, the first column of that figure; see also the first aspect of the invention discussed above):

$$\begin{cases} x'_1 = x - \eta_X(x,y,z) \\ y'_1 = y - \eta_Y(x,y,z) \\ z'_1 = z - \eta_Z(x,y,z) \end{cases} \quad (21)$$

$$\begin{cases} x'_2 = x - \eta_X(x'_1,y'_1,z'_1) \\ y'_2 = y - \eta_Y(x'_1,y'_1,z'_1) \\ z'_2 = z - \eta_Z(x'_1,y'_1,z'_1) \end{cases}, \ldots, \begin{cases} x'_n = x - \eta_X(x'_{n-1},y'_{n-1},z'_{n-1}) \\ y'_n = y - \eta_Y(x'_{n-1},y'_{n-1},z'_{n-1}) \\ z'_n = z - \eta_Z(x'_{n-1},y'_{n-1},z'_{n-1}) \end{cases}$$

At each stage an error term is calculated as follows:

$$E(n) = \frac{\sqrt{(x'_n - x'_{n-1})^2 + (y'_n - y'_{n-1})^2 + (z'_n - z'_{n-1})^2}}{\sqrt{(x'_n - x)^2 + (y'_n - y)^2 + (z'_n - z)^2}}. \quad (22)$$

When the change of this error term between subsequent iterations drops below a critical tolerance (e.g., 0.01), iteration stops. For a 5th and 7th order discrete solution this equates to 2.94(0.0058) and 2.72(0.0053) mean (stddev) iterations respectively.

Figure 8:
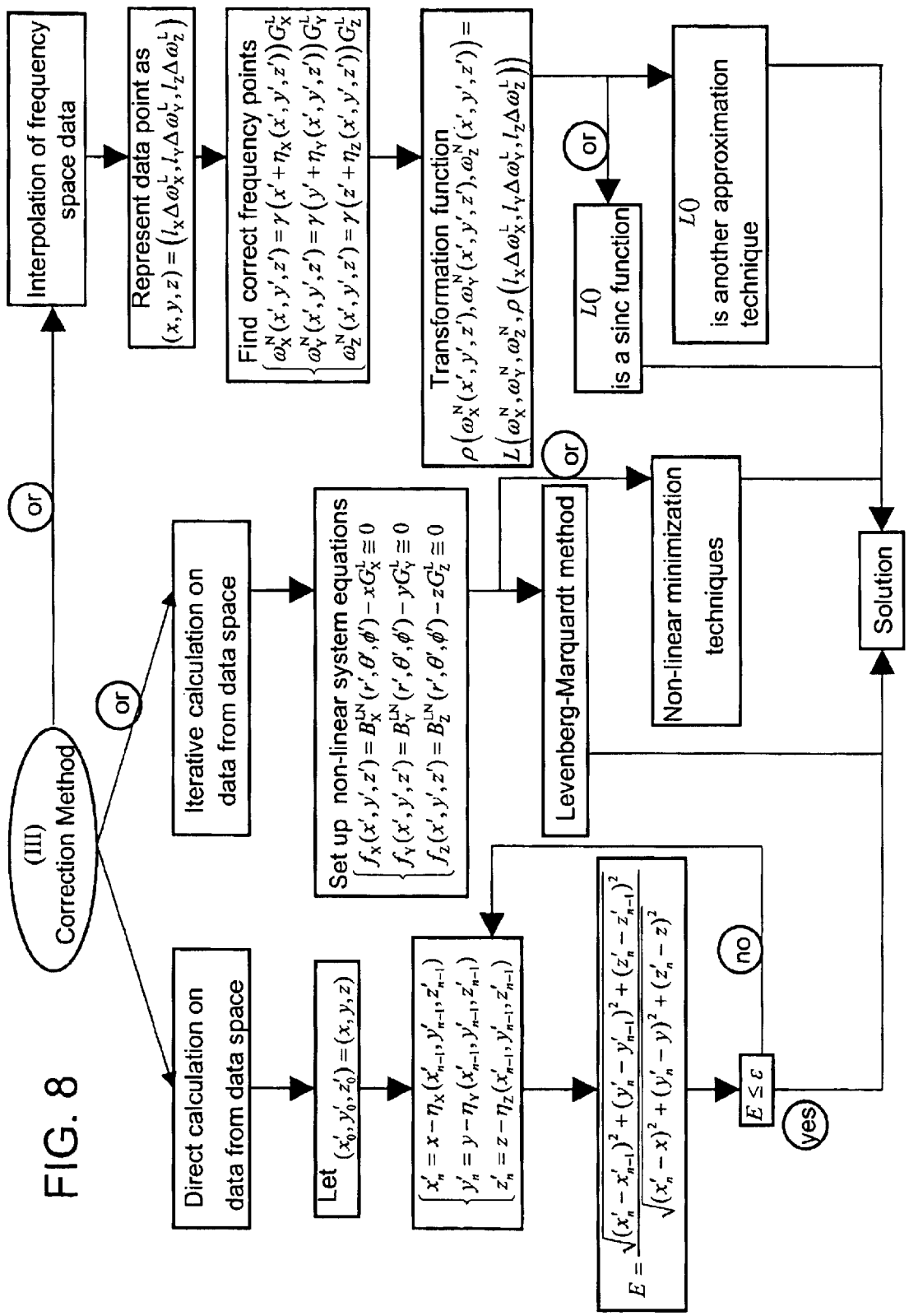
FIG. 8 is a more specific flow chart illustrating three preferred correction methods referred to as "direct calculation on data from data space," "iterative calculation on data from data space," and "interpolation of frequency space data."

As shown in FIG. 8, as alternatives to performing a direct calculation on the data from data space, an iterative calculation on the data from data space can be performed (see the middle column of FIG. 8; see also the second aspect of the invention discussed above) or the corrected image can be obtained by an interpolation of frequency space data (see the last column of FIG. 8; see also the third aspect of the invention discussed above).

The foregoing procedures do not correct for intensity variations arising from the non-linear gradient field dependence nor does it yield pixels having the identical geometric dimensions.

For the method to be most useful in visual data analysis, the pixel dimensions in 2D image data or the voxel dimensions in 3D data, have to be geometrically equal. That is an image is required at a regular set of points ($1_x$,$\Delta x'$,$1_y$,$\Delta y'$,$1_z$, $\Delta z'$). The following operations can be applied to correct both the geometric distortion and the voxel (or pixel) size variations. The corrected coordinates in the (x, y, z) coordinate system are defined as follows:

$$\begin{cases} x_{I_X} = m_{X'}\Delta x' + \eta_X(m_{X'}\Delta x', m_{Y'}\Delta y', m_{Z'}\Delta z') \\ y_{I_Y} = m_{Y'}\Delta y' + \eta_Y(m_{X'}\Delta x', m_{Y'}\Delta y', m_{Z'}\Delta z') \\ z_{I_Z} = m_{Z'}\Delta z' + \eta_Z(m_{X'}\Delta x', m_{Y'}\Delta y', m_{Z'}\Delta z') \end{cases} \quad (23)$$

From this point, a simple non-linear mass preserving resampling of image data using a discrete solution to the deformations expressed in equation (23) is required as per Langlois et al, supra. FIG. 9 further describes specific approaches for obtaining a corrected image at a regular set of points.

The foregoing methods for correcting gradient-based distortion are preferably practiced on a digital computer system configured by suitable programming to perform the various computational steps. The programming can be done in various programming languages known in the art. A preferred programming language is the C++ language which is particularly well-suited to performing scientific calculations and can reduce computing time by a factor of 100:1 compared to general purpose scientific computing packages such as MATH LAB. Other languages which can be used include FORTRAN, BASIC, PASCAL, C, and the like. The program can be embodied as an article of manufacture comprising a computer usable medium, such as a magnetic disc, an optical disc, or the like, upon which the program is encoded.

The computer system can comprise a general purpose scientific computer and its associated peripherals, such as the computers and peripherals currently being manufactured by DIGITAL EQUIPMENT CORPORATION, IBM, HEWLETT-PACKARD, SUN MICROSYSTEMS, SGI or the like. Alternatively and preferably, the computer system can be the same system used by an MRI machine to control the operation of the machine and to record and process image data obtained from the machine. The system should include means for inputting data and means for outputting the results of the image correction process both in electronic and visual form. The output can also be stored on a disk drive, tape drive, or the like for further analysis and/or subsequent display.

VII. EXAMPLES

In order that the invention may be more fully understood and put into practice, preferred embodiments thereof will now be described by way of the following examples and their accompanying drawings. It is to be understood that these specific examples are not intended to limit the scope of the appended claims.

A. Example 1

A set of high speed SONATA gradients manufactured by SIEMENS AKTIENGESELLSCHAFT in Germany was analyzed. The set of SONATA gradients was interfaced to an OXFORD MAGNET TECHNOLOGY 4T whole body magnet and the gradient inhomogeneities were measured using a 24 plane spherical harmonic deconvolution NMR plot. The shimmed magnet was plotted first, followed by two more plots in which a constant current was applied to the X and Z gradients respectively. The harmonics for the shimmed field were subtracted from those generated by the gradients. For simplicity, in this case, it was assumed that the X and Y gradient distortions were identical.

Figure 11:
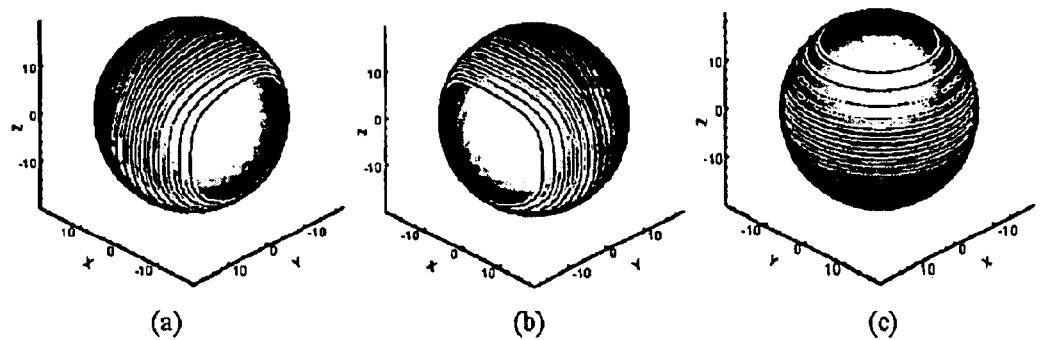
FIG. 11 illustrates the magnetic field distribution on a sphere at a radius of 18 cm for a SONATA gradient set where

The harmonics of interest are listed in Table 1A. Only $4^{th}$ order harmonics are listed as this was sufficient for image correction. For reference, Table 1B shows the harmonics to 7$^{th}$ order. The magnetic field distributions for the X, Y, and Z gradients are shown in FIG. 11.

It is clear from these isomagnetic plots that the gradients produce inhomogeneous magnetic fields and it is likely that image distortion will result when such gradients are used for MRI.

Figure 12:
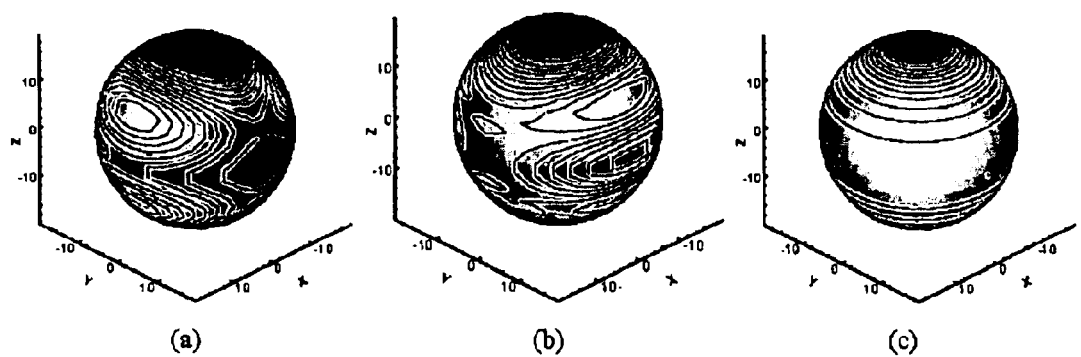
FIG. 12 illustrates Γ(r) plots on a sphere at radius 18 cm using the harmonics from the Table 1A, where

In order to visualize the results, it is useful to introduce the following parameter. For any gradient field, the quality of the linear gradient component can be measured by:

$$\Gamma(r') = \frac{G_V^N(r')}{G_V^L}, \|r'\| \leq r_{dsv} \quad (24)$$

where $r_{dsv}$ is the radius of the DSV. The effect of non-linearity of a gradient field increases as the image volume increases to such an extent that for the SONATA gradients the effective dsv has a radius of less than 10 cm. (As shown below, the effective imaging space is best described by an elliptical volume). In older whole-body MRI instruments, the parameter $\Gamma$ remains within 5% of the desired value over the imaging dsv. However, the compromised linearity of the SONATA gradient set is illustrated in FIG. 12 which shows plots of the $\Gamma$ function. The non-linearity is readily apparent. In particular, the figure demonstrates that the non-linear behavior increases with the displacement from the origin of the MRI system.

It must be appreciated that this gradient set was clearly not designed to optimize gradient linearity; compromises were clearly made to achieve the excellent rise times exhibited by these gradients. Such rise times are critical for cardiac imaging and any other methodology requiring short inter-echo spacing for EPI.

Tables 2A, 2B, and 2C show a second set of harmonic coefficients for these high speed SONATA gradient magnets obtained by a 24 plane spherical harmonic deconvolution NMR plot without the assumption that the X and Y gradient magnets are simply a 90 degree transposition with respect to one another. The zero order harmonics are included in these tables.

In particular, Tables 2A and 2B give the harmonic coefficients for the X and Y gradient magnets, respectively, and Table 2C gives the coefficients for the Z gradient magnet. It should be noted that Tables 2B and 2C contain substantial a(0,0) coefficients and Table 2A contains a small, but non-zero, value for this coefficient, all of which is indicative of the three gradient magnets having at least a displaced center from the origin of the MRI system. In terms of correcting non-linearities in the gradient fields, this offset in the symmetry points of the gradient magnets is easily handled by simply including at least the a(0,0) terms in equation (16). The difference in the signs of the coefficients of Table 2A and the coefficients of Tables 1A and 1B for the X gradient magnet are due to the direction of current used in the gradient coil for the field plot.

In order to speed correction, a discrete solution expressed as a grid function of vectors over an area of interest (+/−120 mm from the origin in x, y and z) with a regular spacing of 5 mm can be generated from the set of spherical harmonic coefficients. Each vector in the volume is generated by iterating towards the solution using the method described in the previous section at each point in the grid and storing the resultant delta values (see equations (20) through (23)).

This set of deformation vectors can then be applied to any data set within its coverage of space. The time taken to non-linearly resample a 256$^3$ image using this approach is ~20 minutes using average computing hardware (RISC 300 Mhz), and the generation of the 5 mm 3D field only takes on the order of seconds. It is important to note that mass preservation resampling can be easily achieved using the above discrete technique via simple multiplication of the Jacobian determinant plus one of the deformation field as part of the resampling. This type of resampling is often termed "mass-preservation resampling."

B. Example 2

As discussed in Example 1, a spherical harmonic deconvolution of the X, Y, Z gradients of a SONATA gradient set was carried out at 4T. It was assumed that the same gradient impurities are present with all manufactured SONATA gradients and the harmonic deconvolution of the gradients at 4T can be used to correct images acquired using a 1.5T SIEMENS SONATA scanner. Otherwise, as discussed above, the particular gradients for a given scanner should be mapped and stored in a look-up table and applied to correct distorted images.

Imaging experiments to assess gradient linearity were performed using a phantom manufactured by BRUKER MEDICAL in Germany. This phantom consists of a cylinder having perfectly flat ends. The diameter of the phantom is 18.5 cm and the depth 3 cm. Within the phantom there are point markers, the spacing between which is a known distance, namely, 2 cm for the main grid. Imaging was performed at 1.5T using a turbo spin echo sequence with a 256×256 mm field of view (matrix size 512×512). The slice thickness was set at 5 mm, TR was set at 500 ms, and TE at 25 ms.

Imaging of such a phantom placed in the XY plane of the magnet should generate an image of a perfect circle. As well, the point markers can be used to map the imaging volume of the gradients by moving the phantom fixed distances along the X, Y, and Z axes. The phantom is depicted in FIG. 13.

FIG. 14*a* shows a 2D image of the phantom sliced in the XY plane with the center of the phantom placed at the center of the imaging domain, i.e. the origin of the MRI system. Note the appearance of the grid markers in the image. A circle has been superimposed onto this image for comparison, and it is clear that there are significant distortions.

The image was then corrected using the harmonics listed in Table 1A and the method of equation (13) above. In particular, the iterative approach of equation (21) was used with a quitting parameter of 1% in equation (22) since this was a proof of concept experiment. In practice, a quitting parameter of 0.1% or less is generally more preferred. The resultant corrected image is shown in FIG. 14*b*. Note that the superimposed circle now fits the image. The background of the image has also been corrected, illustrating that the non-linear gradient behavior of the gradients is increasing dramatically for points further removed from the origin of the MRI system.

To examine the non-linearity over a larger volume, the grid markers from the image obtained with the phantom at the origin of the MRI system was noted and the phantom was re-imaged but its center was moved 10 cm along the Z axis. The grid markers positions were re-measured. The results are shown In FIG. 15, where the open circles show the position of the grid markers acquired from imaging the re-positioned phantom. The dots are the positions the open circles are moved to on application of the same correction used to correct the image in FIG. 14*a*.

FIG. 15 clearly shows that the effective dsv of the SONATA gradients is limited to an elliptical volume having elongation along the Z axis but with limited homogeneous extent in the X and Y directions.

The procedures used to generate FIG. 15 were repeated using the harmonic coefficients of Tables 2A, 2B, and 2C. The results of this experiment are shown in FIG. 16. A comparison of this figure with FIG. 15 reveals that the correction of FIG. 16 is far more accurate because the assumption that the harmonics of the X gradient magnet and the Y gradient magnet are simply 90 degree transpositions of one another is incorrect. Rather, to achieve the highest levels of correction, each gradient coil set must be mapped individually. Also, in FIG. 16, the a(0,0) and b(0,0) harmonic terms are included, i.e., this correction does not, among other things, assume that the main magnet and the gradient magnets have symmetry points which are coincident with the origin of the MRI system.

VII. APPENDIX

In the imaging experiment, the k-space sampling is performed by incrementing the strengths of at least one gradient for 2D imaging and two gradients for 3D imaging. A dimension of k-space is always determined by a constant read gradient. The question arises does the incrementation, the step size of the gradient increment, or the gradient rise time effect the distortion. Or, in other words, is equation (14) generally correct even for an incremented gradient?

Consider the case of a gradient having a rise and fall time $t_2$, which is applied for a constant time T. Suppose the rate of change of gradient during the rise and fall is constant. Further suppose the gradient scaling factor is a. That is, a represents the amount the gradient is incremented to obtain k-space encoding induced by that gradient.

In Table 3, the effective gradient, gradient field, and the effects of scaling are given for the rise time, the gradient on time, and the effect of the scaling factor. It can be clearly seen from this table that the gradient distortion factor can always be separated from the temporal dependence.

IX. CONCLUSION

The methods of this invention correct image distortions induced by gradient non-linearity. Such distortions pose a serious problem for the generation of meaningful images using high speed gradient sets. Although it might be possible to correct such distortions using translation, warping, and twisting matrices, any such attempt will always be empirical. According to this invention, if the gradient field is quantified using an appropriate expansion, then the exact characteristics of the gradient set can be used to correct an image while still employing fast Fourier transform techniques to produce the image data, thus allowing the technique to be routinely used in a clinical setting.

The methods of this invention also correct distortions associated with translational and/or rotational misalignments of the field generating devices, as well as winding and/or design errors in such devices. Like the correction of non-linearities in the gradient fields, these corrections allow for more effective use of MR imaging in clinical settings.

Although specific embodiments of the invention have been described and illustrated, it is to be understood that a variety of modifications which do not depart from the scope and spirit of the invention will be evident to persons of ordinary skill in the art from the foregoing disclosure.

TABLE 1A

| Harmonic | Effect of 2 mT/mX | Effect of 2 mT/mZ |
|---|---|---|
| a(1, 0) | 2.76 | 129.69 |
| a(1, 1) | 142.60 | −0.20 |
| b(1, 1) | −3.03 | −0.05 |
| a(2, 0) | −0.33 | 0.61 |
| a(2, 1) | 0.75 | 0.01 |
| a(2, 2) | 0.06 | 0.10 |
| b(2, 1) | 0.74 | 0.14 |
| b(2, 2) | 1.13 | 0.02 |
| a(3, 0) | −0.50 | −13.76 |
| a(3, 1) | −16.48 | −0.02 |
| a(3, 2) | 0.04 | −0.01 |
| a(3, 3) | 0.07 | −0.05 |
| b(3, 1) | 0.42 | 0.01 |
| b(3, 2) | −0.02 | 0.02 |
| b(3, 3) | 0.06 | −0.01 |
| a(4, 0) | −0.14 | 0.88 |
| a(4, 1) | 0.74 | 0.16 |
| a(4, 2) | −0.01 | 0.00 |
| a(4, 3) | −0.03 | −0.02 |
| a(4, 4) | −0.11 | 0.01 |
| b(4, 1) | −0.07 | −0.57 |
| b(4, 2) | −0.32 | −0.04 |
| b(4, 3) | 0.05 | −0.04 |
| b(4, 4) | −0.21 | −0.47 |

TABLE 1B

| Harmonic | Effect of 2 mT/mGX | Effect of 2 mT/mGZ |
|---|---|---|
| a[1][0] | 2.763 | 129.685 |
| a[1][1] | 142.603 | −0.2 |
| b[1][1] | −3.03 | −0.054 |
| a[2][0] | −0.333 | 0.606 |
| a[2][1] | 0.749 | 0.009 |
| a[2][2] | 0.063 | 0.098 |
| b[2][1] | 0.744 | 0.137 |
| b[2][2] | 1.13 | 0.019 |
| a[3][0] | −0.496 | −13.763 |
| a[3][1] | −16.481 | −0.023 |
| a[3][2] | 0.042 | −0.011 |
| a[3][3] | 0.07 | −0.046 |
| b[3][1] | 0.424 | 0.012 |
| b[3][2] | −0.024 | 0.018 |
| b[3][3] | 0.055 | −0.014 |
| a[4][0] | −0.143 | 0.882 |
| a[4][1] | 0.742 | 0.164 |
| a[4][2] | −0.009 | 0.002 |
| a[4][3] | −0.028 | −0.024 |
| a[4][4] | −0.111 | 0.014 |
| b[4][1] | −0.072 | −0.566 |
| b[4][2] | −0.32 | −0.04 |
| b[4][3] | 0.051 | −0.038 |
| b[4][4] | −0.212 | −0.468 |
| a[5][0] | −0.099 | −12.393 |
| a[5][1] | −10.861 | 0.022 |
| a[5][2] | 0.035 | 0.055 |
| a[5][3] | 0.523 | −0.049 |
| a[5][4] | −0.019 | −0.037 |
| a[5][5] | −0.482 | −0.067 |
| b[5][1] | 0.263 | −0.047 |
| b[5][2] | 0.067 | −0.031 |
| b[5][3] | −0.023 | −0.012 |
| b[5][4] | −0.008 | −0.006 |
| b[5][5] | −0.017 | −0.017 |
| a[6][0] | 0.126 | −0.738 |
| a[6][1] | −0.536 | −0.04 |
| a[6][2] | −0.03 | −0.005 |
| a[6][3] | −0.044 | 0.003 |
| a[6][4] | −0.038 | 0.002 |
| a[6][5] | 0.017 | 0.007 |
| a[6][6] | −0.045 | −0.004 |
| b[6][1] | 0.556 | 0.314 |
| b[6][2] | 0.223 | −0.002 |

TABLE 1B-continued

| Harmonic | Effect of 2 mT/mGX | Effect of 2 mT/mGZ |
|---|---|---|
| b[6][3] | 0.042 | 0.012 |
| b[6][4] | −0.029 | −0.016 |
| b[6][5] | 0.02 | 0.016 |
| b[6][6] | 0.014 | −0.002 |
| a[7][0] | 0.091 | 6.245 |
| a[7][1] | 5.248 | −0.023 |
| a[7][2] | −0.019 | −0.022 |
| a[7][3] | −0.077 | 0.009 |
| a[7][4] | 0.005 | −0.011 |
| a[7][5] | −0.092 | −0.031 |
| a[7][6] | −0.004 | 0.005 |
| a[7][7] | 0.111 | −0.054 |
| b[7][1] | −0.117 | −0.009 |
| b[7][2] | −0.021 | −0.014 |
| b[7][3] | 0.021 | 0.007 |
| b[7][4] | 0.009 | 0.001 |
| b[7][5] | −0.005 | −0.003 |
| b[7][6] | −0.009 | −0.001 |
| b[7][7] | 0.015 | 0.004 |

TABLE 2A

| | | | |
|---|---|---|---|
| a[ 0][ 0] = | 0.0838331648 | b[ 0][ 0] = | 0.0000000000 |
| a[ 1][ 0] = | −1.2716538010 | b[ 1][ 0] = | 0.0000000000 |
| a[ 1][ 1] = | −132.7221691372 | b[ 1][ 1] = | 0.4872918143 |
| a[ 2][ 0] = | −0.2381165388 | b[ 2][ 0] = | 0.0000000000 |
| a[ 2][ 1] = | −0.2759006621 | b[ 2][ 1] = | 1.4427267559 |
| a[ 2][ 2] = | 0.2001160068 | b[ 2][ 2] = | 0.2912038525 |
| a[ 3][ 0] = | 0.1084286246 | b[ 3][ 0] = | 0.0000000000 |
| a[ 3][ 1] = | 8.8803817563 | b[ 3][ 1] = | −0.1482455512 |
| a[ 3][ 2] = | 0.0050844080 | b[ 3][ 2] = | 0.0094718750 |
| a[ 3][ 3] = | −0.0216072875 | b[ 3][ 3] = | 0.0033958941 |
| a[ 4][ 0] = | −0.1042437507 | b[ 4][ 0] = | 0.0000000000 |
| a[ 4][ 1] = | −0.1180010844 | b[ 4][ 1] = | −0.0985654494 |
| a[ 4][ 2] = | −0.0053855068 | b[ 4][ 2] = | −0.0349448661 |
| a[ 4][ 3] = | 0.0009040250 | b[ 4][ 3] = | −0.0026821858 |
| a[ 4][ 4] = | −0.0007279481 | b[ 4][ 4] = | −0.0076957988 |
| a[ 5][ 0] = | 0.1853253763 | b[ 5][ 0] = | 0.0000000000 |
| a[ 5][ 1] = | 3.3493296624 | b[ 5][ 1] = | −0.0421231386 |
| a[ 5][ 2] = | 0.0019933987 | b[ 5][ 2] = | 0.0132843302 |
| a[ 5][ 3] = | −0.0037497794 | b[ 5][ 3] = | −0.0011028998 |
| a[ 5][ 4] = | 0.0000549870 | b[ 5][ 4] = | 0.0001423985 |
| a[ 5][ 5] = | 0.0009245438 | b[ 5][ 5] = | 0.0001627726 |
| a[ 6][ 0] = | −0.0526977040 | b[ 6][ 0] = | 0.0000000000 |
| a[ 6][ 1] = | 0.0690612955 | b[ 6][ 1] = | −0.0612896014 |
| a[ 6][ 2] = | −0.0021269878 | b[ 6][ 2] = | 0.0156958466 |
| a[ 6][ 3] = | 0.0001534714 | b[ 6][ 3] = | −0.0009898018 |
| a[ 6][ 4] = | 0.0001344698 | b[ 6][ 4] = | 0.0004817628 |
| a[ 6][ 5] = | −0.0000004363 | b[ 6][ 5] = | −0.0000151077 |
| a[ 6][ 6] = | −0.0000533362 | b[ 6][ 6] = | 0.0000327604 |
| a[ 7][ 0] = | −0.0749886150 | b[ 7][ 0] = | 0.0000000000 |
| a[ 7][ 1] = | −1.1365618341 | b[ 7][ 1] = | 0.0011569473 |
| a[ 7][ 2] = | 0.0002171400 | b[ 7][ 2] = | 0.0007699258 |
| a[ 7][ 3] = | 0.0000281824 | b[ 7][ 3] = | 0.0001162698 |
| a[ 7][ 4] = | 0.0000260411 | b[ 7][ 4] = | 0.0000979892 |
| a[ 7][ 5] = | −0.0000263748 | b[ 7][ 5] = | −0.0000055753 |
| a[ 7][ 6] = | 0.0000001887 | b[ 7][ 6] = | −0.0000000282 |
| a[ 7][ 7] = | 0.0000039212 | b[ 7][ 7] = | 0.0000023658 |
| a[ 8][ 0] = | −0.0176657736 | b[ 8][ 0] = | 0.0000000000 |
| a[ 8][ 1] = | −0.0064519349 | b[ 8][ 1] = | −0.0207338626 |
| a[ 8][ 2] = | −0.0020002342 | b[ 8][ 2] = | −0.0036056198 |
| a[ 8][ 3] = | 0.0000914662 | b[ 8][ 3] = | −0.0001925300 |
| a[ 8][ 4] = | −0.0000146165 | b[ 8][ 4] = | −0.0000735141 |
| a[ 8][ 5] = | −0.0000029495 | b[ 8][ 5] = | −0.0000000932 |
| a[ 8][ 6] = | 0.0000015070 | b[ 8][ 6] = | −0.0000011350 |
| a[ 8][ 7] = | −0.0000000174 | b[ 8][ 7] = | −0.0000000008 |
| a[ 8][ 8] = | −0.0000001488 | b[ 8][ 8] = | 0.0000007631 |
| a[ 9][ 0] = | 0.0217232335 | b[ 9][ 0] = | 0.0000000000 |
| a[ 9][ 1] = | 0.2659468856 | b[ 9][ 1] = | 0.0107102715 |
| a[ 9][ 2] = | −0.0008638085 | b[ 9][ 2] = | 0.0001375060 |
| a[ 9][ 3] = | 0.0001659842 | b[ 9][ 3] = | −0.0000572176 |
| a[ 9][ 4] = | 0.0000038719 | b[ 9][ 4] = | 0.0000101177 |
| a[ 9][ 5] = | 0.0000013578 | b[ 9][ 5] = | 0.0000009867 |

TABLE 2A-continued

| | | | |
|---|---|---|---|
| a[ 9][ 6] = | 0.0000000921 | b[ 9][ 6] = | 0.0000003657 |
| a[ 9][ 7] = | −0.0000000908 | b[ 9][ 7] = | −0.0000000731 |
| a[ 9][ 8] = | 0.0000000006 | b[ 9][ 8] = | 0.0000000009 |
| a[ 9][ 9] = | −0.0000000101 | b[ 9][ 9] = | 0.0000000037 |

TABLE 2B

| | | | |
|---|---|---|---|
| a[ 0][ 0] = | −3.7900460580 | b[ 0][ 0] = | 0.0000000000 |
| a[ 1][ 0] = | −1.7034159709 | b[ 1][ 0] = | 0.0000000000 |
| a[ 1][ 1] = | −0.7458272678 | b[ 1][ 1] = | −133.7624412246 |
| a[ 2][ 0] = | 1.2758197311 | b[ 2][ 0] = | 0.0000000000 |
| a[ 2][ 1] = | −0.0245587807 | b[ 2][ 1] = | 1.8586775306 |
| a[ 2][ 2] = | −0.0136067897 | b[ 2][ 2] = | 0.0242797720 |
| a[ 3][ 0] = | 0.3999316676 | b[ 3][ 0] = | 0.0000000000 |
| a[ 3][ 1] = | 0.1273432588 | b[ 3][ 1] = | 8.4831640354 |
| a[ 3][ 2] = | 0.0248818876 | b[ 3][ 2] = | −0.0108483922 |
| a[ 3][ 3] = | −0.0047739069 | b[ 3][ 3] = | −0.0136944022 |
| a[ 4][ 0] = | 1.3460911143 | b[ 4][ 0] = | 0.0000000000 |
| a[ 4][ 1] = | −0.0095272670 | b[ 4][ 1] = | 0.0736128110 |
| a[ 4][ 2] = | 0.0402609427 | b[ 4][ 2] = | 0.0027441584 |
| a[ 4][ 3] = | 0.0003820184 | b[ 4][ 3] = | 0.0003540819 |
| a[ 4][ 4] = | 0.0018301692 | b[ 4][ 4] = | 0.0013841028 |
| a[ 5][ 0] = | 0.0810368957 | b[ 5][ 0] = | 0.0000000000 |
| a[ 5][ 1] = | 0.0446932968 | b[ 5][ 1] = | 3.6451221575 |
| a[ 5][ 2] = | 0.0037185706 | b[ 5][ 2] = | −0.0018942448 |
| a[ 5][ 3] = | −0.0003278117 | b[ 5][ 3] = | 0.0036104840 |
| a[ 5][ 4] = | −0.0000689792 | b[ 5][ 4] = | 0.0000270191 |
| a[ 5][ 5] = | −0.0001414358 | b[ 5][ 5] = | 0.0002476716 |
| a[ 6][ 0] = | −1.0619062402 | b[ 6][ 0] = | 0.0000000000 |
| a[ 6][ 1] = | 0.0340525475 | b[ 6][ 1] = | −0.1716021492 |
| a[ 6][ 2] = | −0.0146978298 | b[ 6][ 2] = | −0.0010369322 |
| a[ 6][ 3] = | 0.0006276642 | b[ 6][ 3] = | −0.0003491291 |
| a[ 6][ 4] = | 0.0000708561 | b[ 6][ 4] = | 0.0000313502 |
| a[ 6][ 5] = | −0.0000037154 | b[ 6][ 5] = | −0.0000048289 |
| a[ 6][ 6] = | 0.0000092214 | b[ 6][ 6] = | −0.0000008364 |
| a[ 7][ 0] = | −0.0892241782 | b[ 7][ 0] = | 0.0000000000 |
| a[ 7][ 1] = | −0.0004486569 | b[ 7][ 1] = | −1.2170744655 |
| a[ 7][ 2] = | −0.0002592919 | b[ 7][ 2] = | 0.0015161165 |
| a[ 7][ 3] = | 0.0001990317 | b[ 7][ 3] = | −0.0001196626 |
| a[ 7][ 4] = | −0.0000162520 | b[ 7][ 4] = | −0.0000103351 |
| a[ 7][ 5] = | −0.0000012237 | b[ 7][ 5] = | 0.0000002515 |
| a[ 7][ 6] = | 0.0000002358 | b[ 7][ 6] = | −0.0000004439 |
| a[ 7][ 7] = | −0.0000004771 | b[ 7][ 7] = | −0.0000002674 |
| a[ 8][ 0] = | 0.2532602297 | b[ 8][ 0] = | 0.0000000000 |
| a[ 8][ 1] = | 0.0041351665 | b[ 8][ 1] = | 0.0003812365 |
| a[ 8][ 2] = | 0.0010215207 | b[ 8][ 2] = | −0.0015776826 |
| a[ 8][ 3] = | 0.0001747977 | b[ 8][ 3] = | −0.0001514782 |
| a[ 8][ 4] = | −0.0000090466 | b[ 8][ 4] = | −0.0000037004 |
| a[ 8][ 5] = | −0.0000005470 | b[ 8][ 5] = | −0.0000010101 |
| a[ 8][ 6] = | −0.0000000852 | b[ 8][ 6] = | 0.0000003016 |
| a[ 8][ 7] = | −0.0000000056 | b[ 8][ 7] = | 0.0000000194 |
| a[ 8][ 8] = | 0.0000000392 | b[ 8][ 8] = | −0.0000000776 |
| a[ 9][ 0] = | 0.0188808812 | b[ 9][ 0] = | 0.0000000000 |
| a[ 9][ 1] = | 0.0007637099 | b[ 9][ 1] = | 0.3207591713 |
| a[ 9][ 2] = | −0.0012611680 | b[ 9][ 2] = | −0.0008898966 |
| a[ 9][ 3] = | 0.0000071491 | b[ 9][ 3] = | −0.0001651029 |
| a[ 9][ 4] = | −0.0000030393 | b[ 9][ 4] = | 0.0000026581 |
| a[ 9][ 5] = | −0.0000013149 | b[ 9][ 5] = | −0.0000016304 |
| a[ 9][ 6] = | −0.0000002780 | b[ 9][ 6] = | 0.0000001876 |
| a[ 9][ 7] = | 0.0000000082 | b[ 9][ 7] = | −0.0000000141 |
| a[ 9][ 8] = | 0.0000000007 | b[ 9][ 8] = | 0.0000000006 |
| a[ 9][ 9] = | 0.0000000008 | b[ 9][ 9] = | 0.0000000009 |

TABLE 2C

| | | | |
|---|---|---|---|
| a[ 0][ 0] = | −2.9197922708 | b[ 0][ 0] = | 0.0000000000 |
| a[ 1][ 0] = | 134.7194531231 | b[ 1][ 0] = | 0.0000000000 |
| a[ 1][ 1] = | 0.2203294195 | b[ 1][ 1] = | −0.0408927434 |
| a[ 2][ 0] = | 0.5751081253 | b[ 2][ 0] = | 0.0000000000 |
| a[ 2][ 1] = | −0.0115660272 | b[ 2][ 1] = | 0.2668607814 |
| a[ 2][ 2] = | −0.0077521442 | b[ 2][ 2] = | −0.1452645899 |
| a[ 3][ 0] = | −12.8839436574 | b[ 3][ 0] = | 0.0000000000 |
| a[ 3][ 1] = | −0.0575748576 | b[ 3][ 1] = | 0.0946294096 |
| a[ 3][ 2] = | −0.0070006958 | b[ 3][ 2] = | 0.0034441459 |

TABLE 2C-continued

| | | | |
|---|---|---|---|
| a[ 3 ][ 3 ] = | 0.0064933013 | b[ 3 ][ 3 ] = | 0.0149741926 |
| a[ 4 ][ 0 ] = | 0.9411507001 | b[ 4 ][ 0 ] = | 0.0000000000 |
| a[ 4 ][ 1 ] = | 0.0012817171 | b[ 4 ][ 1 ] = | 0.1877344309 |
| a[ 4 ][ 2 ] = | −0.0011771563 | b[ 4 ][ 2 ] = | −0.0128646297 |
| a[ 4 ][ 3 ] = | 0.0001564982 | b[ 4 ][ 3 ] = | 0.0004787819 |
| a[ 4 ][ 4 ] = | −0.0003930348 | b[ 4 ][ 4 ] = | −0.0016388996 |
| a[ 5 ][ 0 ] = | −8.3848174247 | b[ 5 ][ 0 ] = | 0.0000000000 |
| a[ 5 ][ 1 ] = | −0.0080397919 | b[ 5 ][ 1 ] = | 0.0197622842 |
| a[ 5 ][ 2 ] = | 0.0059353707 | b[ 5 ][ 2 ] = | −0.0001947300 |
| a[ 5 ][ 3 ] = | 0.0004152310 | b[ 5 ][ 3 ] = | 0.0016120543 |
| a[ 5 ][ 4 ] = | −0.0000037362 | b[ 5 ][ 4 ] = | −0.0000028929 |
| a[ 5 ][ 5 ] = | 0.0000333087 | b[ 5 ][ 5 ] = | 0.0001533149 |
| a[ 6 ][ 0 ] = | −0.6168255111 | b[ 6 ][ 0 ] = | 0.0000000000 |
| a[ 6 ][ 1 ] = | 0.0100151346 | b[ 6 ][ 1 ] = | −0.1142332863 |
| a[ 6 ][ 2 ] = | −0.0001338772 | b[ 6 ][ 2 ] = | −0.0003409922 |
| a[ 6 ][ 3 ] = | 0.0001450525 | b[ 6 ][ 3 ] = | −0.0000470285 |
| a[ 6 ][ 4 ] = | −0.0000475882 | b[ 6 ][ 4 ] = | −0.0001474247 |
| a[ 6 ][ 5 ] = | −0.0000013591 | b[ 6 ][ 5 ] = | −0.0000027479 |
| a[ 6 ][ 6 ] = | −0.0000048596 | b[ 6 ][ 6 ] = | −0.0000141927 |
| a[ 7 ][ 0 ] = | 3.7400714270 | b[ 7 ][ 0 ] = | 0.0000000000 |
| a[ 7 ][ 1 ] = | −0.0057047519 | b[ 7 ][ 1 ] = | 0.0139664804 |
| a[ 7 ][ 2 ] = | −0.0002811764 | b[ 7 ][ 2 ] = | 0.0006680224 |
| a[ 7 ][ 3 ] = | 0.0001117112 | b[ 7 ][ 3 ] = | 0.0001400607 |
| a[ 7 ][ 4 ] = | 0.0000079969 | b[ 7 ][ 4 ] = | 0.0000091899 |
| a[ 7 ][ 5 ] = | 0.0000056569 | b[ 7 ][ 5 ] = | 0.0000121548 |
| a[ 7 ][ 6 ] = | 0.0000001838 | b[ 7 ][ 6 ] = | 0.0000000655 |
| a[ 7 ][ 7 ] = | 0.0000003814 | b[ 7 ][ 7 ] = | 0.0000005579 |
| a[ 8 ][ 0 ] = | 0.1597615139 | b[ 8 ][ 0 ] = | 0.0000000000 |
| a[ 8 ][ 1 ] = | 0.0014713576 | b[ 8 ][ 1 ] = | 0.0113239099 |
| a[ 8 ][ 2 ] = | −0.0002586594 | b[ 8 ][ 2 ] = | −0.0020528581 |
| a[ 8 ][ 3 ] = | 0.0000584724 | b[ 8 ][ 3 ] = | −0.0000534010 |
| a[ 8 ][ 4 ] = | −0.0000080827 | b[ 8 ][ 4 ] = | −0.0000199362 |
| a[ 8 ][ 5 ] = | 0.0000000023 | b[ 8 ][ 5 ] = | −0.0000000348 |
| a[ 8 ][ 6 ] = | −0.0000005618 | b[ 8 ][ 6 ] = | −0.0000008039 |
| a[ 8 ][ 7 ] = | −0.0000000025 | b[ 8 ][ 7 ] = | 0.0000000073 |
| a[ 8 ][ 8 ] = | −0.0000000236 | b[ 8 ][ 8 ] = | −0.0000000721 |

TABLE 3

| | linear gradient | Non-linear gradient |
|---|---|---|
| Gradient parameter for the Y gradient. | $G_y$ | $G_y\left(1 + \dfrac{\eta(r)}{y}\right)$ |
| Field during the time $t_2$ (gradient rise and fall time) | $B_z^L = yG_y t_2$, where $t_2 = 0 \ldots \tau$ | $B_z^N = yG_y\left(1 + \dfrac{\eta(r)}{y}\right) t_2$, where $t_2 = 0 \ldots \tau$ |
| Field during the time T (the steady state) | $B_z^L = yG_y \tau$ | $B_z^N = yG_y\left(1 + \dfrac{\eta(r)}{y}\right) \tau$ |
| For change the strength (scale factor $\alpha$) | $B_z^L = yG_y t_2 \alpha$, or $B_z^L = yG_y \tau \alpha$ | $B_z^N = yG_y\left(1 + \dfrac{\eta(r)}{y}\right) t_2 \alpha$, or $B_z^N = yG_y\left(1 + \dfrac{\eta(r)}{y}\right) \tau \alpha$ |

What is claimed is:

1. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function ρ(x,y,z) from the MR data set by a process which comprises performing a three dimensional fast Fourier transform on said data set; and (C) producing a corrected image function ρ(x',y',z') from the uncorrected image function ρ(x,y,z), where the coordinates (x',y',z') represent a corrected position in the x,y,z-coordinate system for the value of the image function at (x,y,z), said (x',y',z') coordinates being determined using an iterative mapping which employs coefficients of spherical harmonic expansions for the magnetic fields produced by the X, Y, and Z gradient magnets (the "spherical harmonic coefficients").

2. The method of claim 1 wherein:

$a_{V(n,m)}$ and $b_{V(n,m)}$ are the spherical harmonic coefficients, where the subscript V is one of X, Y, and Z; and the iterative mapping is of the form:

$$\begin{cases} x' = x - \eta_X(x', y', z') \\ y' = y - \eta_Y(x', y', z') \\ z' = z - \eta_Z(x', y', z') \end{cases}$$

where:
$$\begin{cases} x'_1 = x - \eta_X(x, y, z) \\ y'_1 = y - \eta_Y(x, y, z) \\ z'_1 = z - \eta_Z(x, y, z) \end{cases}$$

$$\begin{cases} x'_2 = x - \eta_X(x'_1, y'_1, z'_1) \\ y'_2 = y - \eta_Y(x'_1, y'_1, z'_1) \\ z'_2 = z - \eta_Z(x'_1, y'_1, z'_1) \end{cases}, \ldots, \begin{cases} x'_n = x - \eta_X(x'_{n-1}, y'_{n-1}, z'_{n-1}) \\ y'_n = y - \eta_Y(x'_{n-1}, y'_{n-1}, z'_{n-1}) \\ z'_n = z - \eta_Z(x'_{n-1}, y'_{n-1}, z'_{n-1}) \end{cases}$$

where n is the iteration number and $\eta_X(x,y,z)$, $\eta_Y(x,y,z)$, and $\eta_Z(x,y,z)$ are given by:

$$\begin{cases} \eta_X(x, y, z) = \dfrac{B_X^N(r, \theta, \phi)}{G_X^L} \\ \eta_Y(x, y, z) = \dfrac{B_Y^N(r, \theta, \phi)}{G_Y^L} \\ \eta_Z(x, y, z) = \dfrac{B_Z^N(r, \theta, \phi)}{G_Z^L} \end{cases}$$

where:

(a) $(r,\theta,\phi)$ values are related to $(x,y,z)$ values by:

$$\begin{cases} r = \sqrt{x^2 + y^2 + z^2} \\ \theta = \tan^{-1}\left(\dfrac{\sqrt{x^2+y^2}}{z}\right); \\ \phi = \tan^{-1}\left(\dfrac{y}{x}\right) \end{cases}$$

(b) $(G_X{}^L = a_{X(1,1)},\ G_Y{}^L = b_{Y(1,1)},\ G_Z{}^L = a_{Z(1,0)})$ represent the linear parts of the gradients $(G_X, G_Y, G_Z)$ of the magnetic fields produced by the X, Y, and Z gradient magnets, respectively; and (c)

$$\begin{cases} B_X^N(r',\theta',\phi') = B_{X(0,0)}(r',\theta',\phi') + \\ \qquad B_{X(1,0)}(r',\theta',\phi') \sum_{n=2}\sum_m B_{X(n,m)}(r',\theta',\phi') \\ B_Y^N(r',\theta',\phi') = B_{Y(0,0)}(r',\theta',\phi') + \\ \qquad B_{Y(1,0)}(r',\theta',\phi') + \sum_{n=2}\sum_m B_{Y(n,m)}(r',\theta',\phi') \\ B_Z^N(r',\theta',\phi') = B_{Z(0,0)}(r',\theta',\phi') + \\ \qquad B_{Z(1,1)}(r',\theta',\phi') + \sum_{n=2}\sum_m B_{Z(n,m)}(r',\theta',\phi') \end{cases}$$

represent the non-linear parts of the magnetic fields produced by the X, Y, and Z gradient magnets, where:

(i) m and n are the indices of the summations and satisfy the relationship $m \leq n$; and (ii) the $B_{V(n,m)}(r,\theta,\phi)$ are given by:

$$B_{V(n,m)}(r,\theta,\phi) = r^n [a_{V(n,m)}\cos(m\phi) + b_{V(n,m)}\sin(m\phi)] P_{(n,m)}(\cos\theta),$$

where the $P_{(n,m)}(\cos\theta)$ are the associated Legendre functions and the subscript V is one of X, Y, and Z.

3. The method of claim 2 wherein the iterative mapping is continued until the following condition is satisfied:

$$\frac{\sqrt{(x'_n - x'_{n-1})^2 + (y'_n - y'_{n-1})^2 + (z'_n - z'_{n-1})^2}}{\sqrt{(x'_n - x)^2 + (y'_n - y)^2 + (z'_n - z)^2}} \leq \varepsilon,$$

where $\varepsilon$ is a predetermined constant and n is the iteration number.

4. The method of claim 3 wherein $$\varepsilon = 10^{-3}.$$

5. The method of claim 4 wherein the iteration number is greater than or equal to 2 and less than or equal to 4.

6. The method of claim 1 wherein the data space of step (A) comprises:

(a) k-space;
(b) time space;
(c) phase space;
(d) frequency space;
(e) time space along at least one coordinate direction and phase space along at least one other coordinate direction; or
(f) time space along at least one coordinate direction and frequency space along at least one other coordinate direction.

7. The method of claim 1 further comprising displaying $\rho(x',y',z')$ as a corrected image.

8. The method of claim 1 further comprising producing an image function $\rho(x'',y'',z'')$ having uniform pixel dimensions from $\rho(x',y',z')$ by performing an interpolation of the form:

$$\rho(x'',y'',z'') = H(x'',y'',z'',\rho(x',y',z'))$$

where H is an interpolation function and $(x'',y'',z'')$ are uniformly distributed point coordinates in the x,y,z-coordinate system.

9. The method of claim 8 wherein the interpolation comprises Lagrange interpolation, Newton interpolation, finite differences interpolation, Hermite interpolation, spline interpolation, or combinations thereof.

10. The method of claim 8 further comprising displaying $\rho(x'',y'',z'')$ as a corrected image.

11. The method of claim 1 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$;

(b) in step (B), the three dimensional fast Fourier transform is performed on the MR data set in the $\zeta$ coordinate system to produce an uncorrected image function $\rho(\zeta_1,\zeta_2,\zeta_3)$ and thereafter, the uncorrected image function $\rho(x,y,z)$ is produced from $\rho(\zeta_1,\zeta_2,\zeta_3)$ by a transformation from the $\zeta$ coordinate system to the x,y,z-coordinate system; and (c) after step (C), a corrected image function $\rho(\zeta'_1,\zeta'_2,\zeta'_3)$ in the $\zeta$ coordinate system is produced from the corrected image function $\rho(x',y',z')$ of step (C) by a transformation from the x,y,z-coordinate system to the $\zeta$ coordinate system.

12. The method of claim 11 further comprising displaying $\rho(\zeta'_1,\zeta'_2,\zeta'_3)$ as a corrected image.

13. The method of claim 11 further comprising producing an image function $\rho(\zeta''_1,\zeta''_2,\zeta''_3)$ having uniform pixel dimensions from $\rho(\zeta'_1,\zeta'_2,\zeta'_3)$ by performing an interpolation of the form:

$$\rho(\zeta''_1,\zeta''_2,\zeta''_3) = H(\zeta''_1,\zeta''_2,\zeta''_3,\rho(\zeta'_1,\zeta'_2,\zeta'_3))$$

where H is an interpolation function and $(\zeta''_1,\zeta''_2,\zeta''_3)$ are uniformly distributed point coordinates in the; coordinate system.

14. The method of claim 13 further comprising displaying $\rho(\zeta''_1,\zeta''_2,\zeta''_3)$ as a corrected image.

15. The method of claim 1 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$;

(b) in step (B), the three dimensional fast Fourier transform is performed on the MR data set in the $\zeta$ coordinate system to produce an uncorrected image function $\rho(\zeta_1,\zeta_2,\zeta_3)$ and thereafter, the uncorrected image function $\rho(x,y,z)$ is produced from $\rho(\zeta_1,\zeta_2,\zeta_3)$ by a transformation from the $\zeta$ coordinate system to the x,y,z-coordinate system; and (c) after step (C), an image function $\rho(x'',y'',z'')$ having uniform pixel dimensions is produced from $\rho(x',y',z')$ by performing an interpolation of the form:

$$\rho(x'',y'',z'') = H(x'',y'',z'',\rho(x',y',z'))$$

where H is an interpolation function and (x",y",z") are uniformly distributed point coordinates in the x,y,z-coordinate system; and (d) thereafter, a corrected image function $\rho(\zeta'_1,\zeta'_2,\zeta'_3)$ in the $\zeta$ coordinate system is produced from the image function $\rho(x",y",z")$ by a transformation from the x,y,z-coordinate system to the $\zeta$ coordinate system.

16. The method of claim 15 further comprising displaying $\rho(\zeta'_1,\zeta'_2,\zeta'_3)$ as a corrected image.

17. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function $\rho(x,y,z)$ from the MR data set by a process which comprises performing a three dimensional fast Fourier transform on said data set; and (C) producing a corrected image function $\rho(x',y',z')$ from the uncorrected image function $\rho(x,y,z)$, where the coordinates (x',y',z') represent a corrected position in the x,y,z-coordinate system for the value of the image function at (x,y,z), said (x',y',z') coordinates being determined by solving a system of non-linear equations so that an error function f(x',y',z') satisfies the relationship:

$$\|f(x',y',z')\| \leq \epsilon,$$

where $\epsilon$ is a predetermined constant;

wherein the system of non-linear equations employs coefficients of spherical harmonic expansions for the magnetic fields produced by the X, Y, and Z gradient magnets (the "spherical harmonic coefficients").

18. The method of claim 17 wherein:

$a_{V(n,m)}$ and $b_{V(n,m)}$ are the spherical harmonic coefficients, where the subscript V is one of X, Y, and Z;

the system of non-linear equations is solved iteratively using ($x_0'=x$, $y_0'=y$, $z_0'=z$) as the initial (x',y',z') values; and the error function and the system of non-linear equations are of the form:

$$f(x', y', z') = \begin{cases} f_X(x', y', z') = B_X^{LN}(r', \theta', \phi') - xG_X^L \cong 0 \\ f_Y(x', y', z') = B_Y^{LN}(r', \theta', \phi') - yG_Y^L \cong 0 \\ f_Z(x', y', z') = B_Z^{LN}(r', \theta', \phi') - zG_Z^L \cong 0 \end{cases}$$

where:

(a) (x', y', z') values and (r', $\theta'$, $\phi'$) values are related by:

$$\begin{cases} r' = \sqrt{x'^2 + y'^2 + z'^2} \\ \theta' = \tan^{-1}\left(\frac{\sqrt{x'^2 + y'^2}}{z'}\right) \\ \phi' = \tan^{-1}\left(\frac{y'}{x'}\right) \end{cases}$$

(b) ($G_X^L = a_{X(1,1)}$, $G_Y^L = b_{Y(1,1)}$, $G_Z^L = a_{Z(1,0)}$) represent the linear parts of the gradients ($G_X$, $G_Y$, $G_Z$) of the magnetic fields produced by the X, Y, and Z gradient magnets, respectively; and $$\begin{cases} B_X^{LN}(r', \theta', \phi') = \sum_{n=0} \sum_m B_{X(n,m)}(r', \theta', \phi') \\ B_Y^{LN}(r', \theta', \phi') = \sum_{n=0} \sum_m B_{Y(n,m)}(r', \theta', \phi') \\ B_Z^{LN}(r', \theta', \phi') = \sum_{n=0} \sum_m B_{Z(n,m)}(r', \theta', \phi') \end{cases}$$

represent the linear and non-linear parts of the magnetic fields produced by the X, Y, and Z gradient magnets, where:

(i) m and n are the indices of the summations and satisfy the relationship $m \leq n$; and (ii) $B_{V(n,m)}(r',\theta',\phi')$ is given by:

$$B_{V(n,m)}(r;\theta',\phi')=r'^n[a_{V(n,m)}\cos(m\phi')+b_{V(n,m)}\sin(m\phi')]P_{(n,m)}(\cos\theta')$$

where the $P_{(n,m)}(\cos\theta')$ are associated Legendre functions and the subscript V is one of X, Y, and Z.

19. The method of claim 18 wherein a Levenberg-Marquardt non-linear curve fitting technique is used in solving the system of non-linear equations.

20. The method of claim 18 wherein a non-linear minimization technique is used in solving the system of non-linear equations.

21. The method of claim 17 wherein:

$$\epsilon = R_{es} \times 10^{-3},$$

where $R_{es}$ is the resolution of the image given by:

$$R_{es} = A_{image}/N_{pix},$$

where $A_{image}$ is the area of the image and $N_{pix}$ is total number of pixels making up the image.

22. The method of claim 17 wherein the data space of step (A) comprises:

(a) k-space;
(b) time space;
(c) phase space;
(d) frequency space;
(e) time space along at least one coordinate direction and phase space along at least one other coordinate direction; or
(f) time space along at least one coordinate direction and frequency space along at least one other coordinate direction.

23. The method of claim 17 further comprising displaying $\rho(x',y',z')$ as a corrected image.

24. The method of claim 17 further comprising producing an image function $\rho(x",y",z")$ having uniform pixel dimen sions from ρ(x',y',z') by performing an interpolation of the form:

$$\rho(x'',y'',z'')=H(x'',y'',z'',\rho(x',y',z'))$$

where H is an interpolation function and (x',y',z') are uniformly distributed point coordinates in the x,y,z-coordinate system.

25. The method of claim 24 wherein the interpolation comprises Lagrange interpolation, Newton interpolation, finite differences interpolation, Hermite interpolation, spline interpolation, or combinations thereof.

26. The method of claim 24 further comprising displaying ρ(x",y",z") as a corrected image.

27. The method of claim 17 wherein:
(a) in step (A), the MR data set is acquired in a Cartesian coordinate system ζ which has a common origin with the x,y,z-coordinate system but is rotated with respect to that coordinate system, the axes of the ζ coordinate system being $(\zeta_1, \zeta_2, \zeta_3)$;
(b) in step (B), the three dimensional fast Fourier transform is performed on the MR data set in the ζ coordinate system to produce an uncorrected image function $\rho(\zeta_1, \zeta_2, \zeta_3)$ and thereafter, the uncorrected image function ρ(x,y,z) is produced from $\rho(\zeta_1, \zeta_2, \zeta_3)$ by a transformation from the ζ coordinate system to the x,y,z-coordinate system; and
(c) after step (C), a corrected image function $\rho(\zeta'_1, \zeta'_2, \zeta'_3)$ in the ζ coordinate system is produced from the corrected image function ρ(x',y',z') of step (C) by a transformation from the x,y,z-coordinate system to the ζ coordinate system.

28. The method of claim 27 further comprising displaying $\rho(\zeta'_1, \zeta'_2, \zeta'_3)$ as a corrected image.

29. The method of claim 27 further comprising producing an image function $\rho(\zeta''_1, \zeta''_2, \zeta''_3)$ having uniform pixel dimensions from $\rho(\zeta'_1, \zeta'_2, \zeta'_3)$ by performing an interpolation of the form:

$$\rho(\zeta''_1, \zeta''_2, \zeta''_3)=H(\zeta''_1, \zeta''_2, \zeta''_3, \rho(\zeta'_1, \zeta'_2, \zeta'_3))$$

where H is an interpolation function and $(\zeta''_1, \zeta''_2, \zeta''_3)$ are uniformly distributed point coordinates in the ζ coordinate system.

30. The method of claim 29 further comprising displaying $\rho(\zeta''_1, \zeta''_2, \zeta''_3)$ as a corrected image.

31. The method of claim 17 wherein:
(a) in step (A), the MR data set is acquired in a Cartesian coordinate system ζ which has a common origin with the x,y,z-coordinate system but is rotated with respect to that coordinate system, the axes of the ζ coordinate system being $(\zeta_1, \zeta_2, \zeta_3)$;
(b) in step (B), the three dimensional fast Fourier transform is performed on the MR data set in the ζ coordinate system to produce an uncorrected image function $\rho(\zeta_1, \zeta_2, \zeta_3)$ and thereafter, the uncorrected image function ρ(x,y,z) is produced from $\rho(\zeta_1, \zeta_2, \zeta_3)$ by a transformation from the ζ coordinate system to the x,y,z-coordinate system; and
(c) after step (C), an image function ρ(x",y",z") having uniform pixel dimensions is produced from ρ(x',y',z') by performing an interpolation of the form:

$$\rho(x'',y'',z'')=H(x'',y'',z'',\rho(x',y',z'))$$

where H is an interpolation function and (x",y",z") are uniformly distributed point coordinates in the x,y,z-coordinate system; and (d) thereafter, a corrected image function $\rho(\zeta'_1, \zeta'_2, \zeta'_3)$ in the ζ coordinate system is produced from the image function ρ(x",y",z") by a transformation from the x,y,z-coordinate system to the ζ coordinate system.

32. The method of claim 31 further comprising displaying $\rho(\zeta'_1, \zeta'_2, \zeta'_3)$ as a corrected image.

33. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients $(G_X, G_Y, G_Z)$, respectively, said method comprising:

(A) acquiring a magnetic resonance signal data set (the "MR data set") for the object in three dimensions in data space using the X, Y, and Z gradient magnets, where the MR data set is of the form $s(m_X\Delta t_X, m_Y\Delta t_Y, m_Z\Delta t_Z)$ where:
(i) $m_X$, $m_Y$ and $m_Z$ are indices for the data points in the x, y, and z directions, respectively; and
(ii) $\Delta t_X$, $\Delta t_Y$ and $\Delta t_Z$ are equivalent time steps in the x, y, and z directions, respectively;

(B) producing an uncorrected image function $\rho(l_X\Delta\omega_X^L, l_Y\Delta\omega_Y^L, l_Z\Delta\omega_Z^L)$ from the MR data set by a process which comprises performing a three dimensional fast Fourier transform on said data set, said uncorrected image function being in frequency space at a set of frequency points given by $(l_X\Delta\omega_X^L, l_Y\Delta\omega_Y^L, l_Z\Delta\omega_Z^L)$ where:
(i) $l_X$, $l_Y$ and $l_Z$ are indices for the frequency points in the $\omega_X^L$, $\omega_Y^L$ and $\omega_Z^L$ directions, respectively;
(ii) $\Delta\omega_X^L$, $\Delta\omega_Y^L$ and $\Delta\omega_Z^L$ are frequency steps in the $\omega_X^L$, $\omega_Y^L$ and $\omega_Z^L$ directions, respectively;
(iii) $\omega_X^L=\gamma x G_X^L$, $\omega_Y^L=\gamma y G_Y^L$, $\omega_Z^L=\gamma z G_Z^L$, where:
  (a) γ is a constant; and
  (b) $G_X^L$, $G_Y^L$, and $G_Z^L$ represent the linear parts of the gradients $(G_X, G_Y, G_Z)$ of the magnetic fields produced by the X, Y, and Z gradient magnets, respectively;
(iv) the ranges of $l_X$, $l_Y$, and $l_Z$ are selected so that $l_X\cdot\Delta\omega_X^L$, $l_Y\cdot\Delta\omega_Y^L$, and $l_Z\cdot\Delta\omega_Z^L$ respectively span the frequency ranges that would arise from the X, Y, and Z gradient magnets if those magnets produced purely linear gradient fields in the x, y, and z directions of the x,y,z-coordinate system; and
(v) the fast Fourier transform is of the form:

$$\rho(l_X\Delta\omega_X^L, l_Y\Delta\omega_Y^L, l_Z\Delta\omega_Z^L) = \sum_{m_X}\sum_{m_Y}\sum_{m_Z} s(m_X\Delta t_X, m_Y\Delta t_Y, m_Z\Delta t_Z)$$

$$e^{i(l_X\Delta\omega_X^L\cdot m_X\Delta t_X + l_Y\Delta\omega_Y^L\cdot m_Y\Delta t_Y + l_Z\Delta\omega_Z^L\cdot m_Z\Delta t_Z)}$$

$$\Delta t_X \Delta t_Y \Delta t_Z$$

(C) producing a corrected image function ρ(x',y',z') at (x',y',z') in the x,y,z-coordinate system from the uncorrected image function $\rho(l_X\Delta\omega_X^L, l_Y\Delta\omega_Y^L, l_Z\Delta\omega_Z^L)$ using an interpolation function L in frequency space of the form:

$$\rho(\omega_X^N, \omega_Y^N, \omega_Z^N) = L(\omega_X^N, \omega_Y^N, \omega_Z^N, \rho(l_X\Delta\omega_X^L, l_Y\Delta\omega_Y^L, l_Z\Delta\omega_Z^L))$$

where:
(i) $\omega_X^N$, $\omega_Y^N$, and $\omega_Z^N$ are each a function of (x',y',z'); and
(ii) $\rho(\omega_X^N, \omega_Y^N, \omega_Z^N)$ equals the desired ρ(x',y',z');

wherein $G_X^L$, $G_Y^L$, $G_Z^L$, $\omega_X^N$, $\omega_Y^N$, and $\omega_Z^N$ are determined using coefficients of spherical harmonic expansions for the magnetic fields produced by the X, Y, and Z gradient magnets (the "spherical harmonic coefficients").

34. The method of claim 33 wherein:

(a) $a_{V(n,m)}$ and $b_{V(n,m)}$ are the spherical harmonic coefficients, where the subscript V is one of X, Y, and Z;

(b) $G_X^L = a_{X(1,1)}$, $G_Y^L = b_{Y(1,1)}$, and $G_Z^L = a_{Z(1,0)}$; and (c), $\omega_X^N$, $\omega_Y^N$, and $\omega_Z^N$ are given by:

$$\begin{cases} \omega_X^N = \gamma(x' + \eta_X(x',y',z'))G_X^L \\ \omega_Y^N = \gamma(y' + \eta_Y(x',y',z'))G_Y^L \\ \omega_Z^N = \gamma(z' + \eta_Z(x',y',z'))G_Z^L \end{cases}$$

where $\eta_X(x',y',z')$, $\eta_Y(x',y',z')$ and $\eta_Z(x',y',z')$ are given by:

$$\begin{cases} \eta_X(x',y',z') = \frac{B_X^N(r',\theta',\phi')}{G_X^L} \\ \eta_Y(x',y',z') = \frac{B_Y^N(r',\theta',\phi')}{G_Y^L} \\ \eta_Z(x',y',z') = \frac{B_Z^N(r',\theta',\phi')}{G_Z^L} \end{cases}$$

where $$\begin{cases} B_X^N(r',\theta',\phi') = B_{X(0,0)}(r',\theta',\phi') + \\ \quad B_{X(1,0)}(r',\theta',\phi') + \sum_{n=2}\sum_m B_{X(n,m)}(r',\theta',\phi') \\ B_Y^N(r',\theta',\phi') = B_{Y(0,0)}(r',\theta',\phi') + \\ \quad B_{Y(1,0)}(r',\theta',\phi') + \sum_{n=2}\sum_m B_{Y(n,m)}(r',\theta',\phi') \\ B_Z^N(r',\theta',\phi') = B_{Z(0,0)}(r',\theta',\phi') + \\ \quad B_{Z(1,1)}(r',\theta',\phi') + \sum_{n=2}\sum_m B_{Z(n,m)}(r',\theta',\phi') \end{cases}$$

represent the non-linear parts of the magnetic fields produced by the X, Y, and Z gradient magnets, where:

(i) m and n are the indices of the summations and satisfy the relationship $m \leq n$;

(ii) $B_{V(n,m)}(r',\theta',\phi')$ is given by:

$$B_{V(n,m)}(r',\theta',\phi') = r'^n[a_{V(n,m)}\cos(m\phi') + b_{V(n,m)}\sin(m\phi')]P_{(n,m)}(\cos\theta')$$

where the $P_{(n,m)}(\cos\theta')$ are associated Legendre functions and the subscript V is one of X, Y, and Z; and (iii) (x', y', z') values and (r', θ', φ') values are related by:

$$\begin{cases} r' = \sqrt{x'^2 + y'^2 + z'^2} \\ \theta' = \tan^{-1}\left(\frac{\sqrt{x'^2 + y'^2}}{z'}\right) \\ \phi' = \tan^{-1}\left(\frac{y'}{x'}\right) \end{cases}$$

35. The method of claim 33 wherein the interpolation function L is a sinc function such that:

$$L(\omega_X^N, \omega_Y^N, \omega_Z^N, \rho(l_X\Delta\omega_X^L, l_Y\Delta\omega_Y^L, l_Z\Delta\omega_Z^L)) = $$

$$\sum_{l_Z}\sum_{l_Y}\sum_{l_X} \rho(l_X\Delta\omega_X^L, l_Y\Delta\omega_Y^L, l_Z\Delta\omega_Z^L)$$

$$\text{sinc}\left(\frac{\omega_X^N}{\Delta\omega_X^L} - l_X, \frac{\omega_Y^N}{\Delta\omega_Y^L} - l_Y, \frac{\omega_Z^N}{\Delta\omega_Z^L} - l_Z\right).$$

36. The method of claim 33 wherein the interpolation function L is of the form:

$$L(\omega_X^N, \omega_Y^N, \omega_Z^N, \rho(l_X\Delta\omega_X^L, l_Y\Delta\omega_Y^L, l_Z\Delta\omega_Z^L)) = $$

$$\sum_{l_Z}\sum_{l_Y}\sum_{l_X} C_{(l_X,l_Y,l_Z)}\psi_{X(l_X)}(\omega_X^N)\psi_{Y(l_Y)}(\omega_Y^N)\psi_{Z(l_Z)}(\omega_Z^N)$$

where:

(a) $\psi_{X(l_X)}$, $\psi_{Y(l_Y)}$ and $\psi_{Z(l_Z)}$ are orthogonal bases functions; and (b) the $C_{(l_X,l_Y,l_Z)}$ are coefficients which satisfy the matrix equation:

$$AC = \rho$$

where the vector C is of the form:

$$C = [C_{(1,1,1)}\ C_{(2,1,1)}\ \ldots\ C_{(l_X,l_Y,l_Z)}]^T$$

the vector ρ is of the form:

$$\rho[\rho(\omega_{X(1)}^L,\omega_{Y(1)}^L,\omega_{Z(1)}^L)\rho(\omega_{X(2)}^L,\omega_{Y(1)}^L,\omega_{Z(1)}^L)\ldots\rho(\omega_{X(l_X)}^L,\omega_{Y(l_Y)}^L,\omega_{Z(l_Z)}^L)]^T$$

and the matrix A is of the form;

$$\begin{bmatrix} \beta_{(1,1)} & \beta_{(1,2)} & \cdots & \beta_{(1,q)} \\ \beta_{(2,1)} & \beta_{(2,2)} & \cdots & \beta_{(2,q)} \\ \vdots & \vdots & \ddots & \vdots \\ \beta_{(q,1)} & \beta_{(q,2)} & \cdots & \beta_{(q,q)} \end{bmatrix}$$

where $\beta_{(1,1)} = \psi_{X(1)}(\omega_{X(1)}^L)\psi_{Y(1)}(\omega_{Y(1)}^L)\psi_{Z(1)}(\omega_{Z(1)}^L)$, $\beta_{(1,2)} = \psi_{X(2)}(\omega_{X(1)}^L)\psi_{Y(1)}(\omega_{Y(1)}^L)\psi_{Z(1)}(\omega_{Z(1)}^L)$, $\vdots$ $\beta_{(1,q)} = \psi_{X(l_X)}(\omega_{X(1)}^L)\psi_{Y(l_Y)}(\omega_{Y(1)}^L)\psi_{Z(l_Z)}(\omega_{Z(1)}^L)$;

$\beta_{(2,1)} = \psi_{X(1)}(\omega_{X(2)}^L)\psi_{Y(1)}(\omega_{Y(1)}^L)\psi_{Z(1)}(\omega_{Z(1)}^L)$, $\beta_{(2,2)} = \psi_{X(2)}(\omega_{X(2)}^L)\psi_{Y(1)}(\omega_{Y(1)}^L)\psi_{Z(1)}(\omega_{Z(1)}^L)$, $\vdots$ $\beta_{(2,q)} = \psi_{X(l_X)}(\omega_{X(2)}^L)\psi_{Y(l_Y)}(\omega_{Y(1)}^L)\psi_{Z(l_Z)}(\omega_{Z(1)}^L)$;

$\vdots$ $\beta_{(q,1)} = \psi_{X(1)}(\omega_{X(l_X)}^L)\psi_{Y(1)}(\omega_{Y(l_Y)}^L)\psi_{Z(1)}(\omega_{Z(l_Z)}^L)$, $\beta_{(q,2)} = \psi_{X(2)}(\omega_{X(l_X)}^L)\psi_{Y(1)}(\omega_{Y(l_Y)}^L)\psi_{Z(1)}(\omega_{Z(l_Z)}^L)$, $\beta_{(q,q)} = \psi_{X(l_X)}(\omega_{X(l_X)}^L)\psi_{Y(l_Y)}(\omega_{Y(l_Y)}^L)\psi_{Z(l_Z)}(\omega_{Z(l_Z)}^L)$, where $q \leq [l_X \times l_Y \times l_Z]_{\max}$.

37. The method of claim 36 wherein the interpolation comprises Lagrange's interpolation, Newton interpolation, finite difference interpolation, Hermite interpolation, spline interpolation, or combinations thereof.

38. The method of claim 36 wherein the interpolation is applied to all of the data points obtained by performing the three dimensional fast Fourier transform on the MR data set.

39. The method of claim 36 wherein the interpolation is applied to a subset of the data points obtained by performing the three dimensional fast Fourier transform on the MR data set, said subset being in the vicinity of a region of interest of the object being imaged.

40. The method of claim 33 further comprising displaying $\rho(x',y',z')$ as a corrected image.

41. The method of claim 33 further comprising producing an image function $\rho(x'',y'',z'')$ having uniform pixel dimensions from $\rho(x',y',z')$ by performing an interpolation of the form:

$$\rho(x'',y'',z'')=H(x'',y'',z'',\rho(x',y',z'))$$

where H is an interpolation function and $(x'',y'',z'')$ are uniformly distributed point coordinates in the x,y,z-coordinate system.

42. The method of claim 41 wherein the interpolation comprises Lagrange interpolation, Newton interpolation, finite differences interpolation, Hermite interpolation, spline interpolation, or combinations thereof.

43. The method of claim 42 further comprising displaying $\rho(x'',y'',z'')$ as a corrected image.

44. The method of claim 33 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$ and the transformation between the x,y,z and $\zeta$ coordinate systems (the "xyz-$\zeta$ transformation") being of the form:

$$r = A\zeta \text{ and } \zeta = A^{-1}r$$

where $$r = [x, y, z]^T,$$

$$\zeta = [\zeta_1, \zeta_2, \zeta_3]^T, \text{ and}$$

$$A = \begin{bmatrix} c_{11} & c_{12} & c_{13} \\ c_{21} & c_{22} & c_{23} \\ c_{31} & c_{32} & c_{33} \end{bmatrix} \text{ (the "A matrix"),}$$

where the c's are direction cosines;

(b) in step (B), the three dimensional fast Fourier transform is performed on the MR data set in the $\zeta$ coordinate system to produce an uncorrected image function in $(\omega_{\zeta_1},\omega_{\zeta_2},\omega_{\zeta_3})$ frequency space, and thereafter, an uncorrected image function in $(\omega_X,\omega_Y,\omega_Z)$ frequency space is produced by a transformation of the $(\omega_{\zeta_1},\omega_{\zeta_2},\omega_{\zeta_3})$ frequencies to the $(\omega_X,\omega_Y,\omega_Z)$ frequencies of the form:

$$\omega_{(X,Y,Z)}=A\omega_{(\zeta_1,\zeta_2,\zeta_3)}$$

where $\omega_{(X,Y,Z)}=[\omega_X,\omega_Y,\omega_Z]^T$, $\omega_{(\zeta_1,\zeta_2,\zeta_3)}=[\omega_{\zeta_1},\omega_{\zeta_2},\omega_{\zeta_3}]^T$, and A is the A matrix; and (c) after step (C), a corrected image function $\rho(\zeta'_1,\zeta'_2,\zeta'_3)$ in the $\zeta$ coordinate system is produced from the corrected image function $\rho(x',y',z')$ of step (C) using the xyz-$\zeta$ transformation.

45. The method of claim 44 further comprising displaying $\rho(\zeta'_1,\zeta'_2,\zeta'_3)$ as a corrected image.

46. The method of claim 44 further comprising producing an image function $\rho(\zeta''_1,\zeta''_2,\zeta''_3)$ having uniform pixel dimensions from $\rho(\zeta'_1,\zeta'_2,\zeta'_3)$ by performing an interpolation of the form:

$$\rho(\zeta''_1,\zeta''_2,\zeta''_3)=H(\zeta''_1,\zeta''_2,\zeta''_3,\rho(\zeta'_1,\zeta'_2,\zeta'_3))$$

where H is an interpolation function and $(\zeta''_1,\zeta''_2,\zeta''_3)$ are uniformly distributed point coordinates in the $\zeta$ coordinate system.

47. The method of claim 46 further comprising displaying $\rho(\zeta''_1,\zeta''_2,\zeta''_3)$ as a corrected image.

48. The method of claim 33 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$ and the transformation between the x,y,z and $\zeta$ coordinate systems (the "xyz-$\zeta$ transformation") being of the form:

$$A = \begin{bmatrix} c_{11} & c_{12} & c_{13} \\ c_{21} & c_{22} & c_{23} \\ c_{31} & c_{32} & c_{33} \end{bmatrix} \text{ (the "A matrix"),}$$

where the c's are direction cosines;

(b) in step (B), the three dimensional fast Fourier transform is performed on the MR data set in the $\zeta$ coordinate system to produce an uncorrected image function in $(\omega_{\zeta_1},\omega_{\zeta_2},\omega_{\zeta_3})$ frequency space, and thereafter, an uncorrected image function in $(\omega_X,\omega_Y,\omega_Z)$ frequency space is produced by a transformation of the $(\omega_{\zeta_1},\omega_{\zeta_2},\omega_{\zeta_3})$ frequencies to the $(\omega_X,\omega_Y,\omega_Z)$ frequencies of the form:

$$\omega_{(X,Y,Z)}=A\omega_{(\zeta_1,\zeta_2,\zeta_3)}$$

where $\omega_{(X,Y,Z)}=[\omega_X,\omega_Y,\omega_Z]^T$, $\omega_{(\zeta_1,\zeta_2,\zeta_3)}=[\omega_{\zeta_1},\omega_{\zeta_2},\omega_{\zeta_3}]^T$, and A is the A matrix; and (c) after step (C), an image function $\rho(x'',y'',z'')$ having uniform pixel dimensions is produced from $\rho(x',y',z')$ by performing an interpolation of the form:

$$\rho(x'',y'',z'')=H(x'',y'',z'',\rho(x',y',z'))$$

where H is an interpolation function and $(x'',y'',z'')$ are uniformly distributed point coordinates in the x,y,z-coordinate system; and (d) thereafter, a corrected image function $\rho(\zeta'_1,\zeta'_2,\zeta'_3)$ in the $\zeta$ coordinate system is produced from the image function $\rho(x'',y'',z'')$ using the xyz-$\zeta$ transformation.

49. The method of claim 48 further comprising displaying $\rho(\zeta'_1,\zeta'_2,\zeta'_3)$ as a corrected image.

50. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients $(G_X, G_Y, G_Z)$, respectively, said method comprising:

(A) acquiring a magnetic resonance signal data set (the "MR data set") for a slice of the object in two dimensions in data space using a linear combination of the X, Y, and Z gradient magnets;

(B) producing an uncorrected image function $\rho(\zeta_1,\zeta_2)$ from the MR data set by a process which comprises performing a two dimensional fast Fourier transform on said data set, where $\zeta_1$ and $\zeta_2$ are read and phase encoding coordinates, respectively, of a $(\zeta_1,\zeta_2,\zeta_3)$ coordinate system wherein:

(i) a slice select gradient is given in the $(\zeta_1,\zeta_2,\zeta_3)$ coordinate system by:

$$G_3=(p_{X3}G_X, p_{Y3}G_Y, p_{Z3}G_Z)$$

where $(p_{X3}, p_{Y3}, p_{Z3})$ are gradient strength coefficients of the X, Y, and Z gradient magnets $(G_X, G_Y, G_Z)$, respectively, and the axis direction of the slice gradient is:

$$\hat{\zeta}_3 = (\sin\theta_3\cos\phi_3, \sin\theta_3\sin\phi_3, \cos\theta_3)$$

where $$\theta_3 = \tan^{-1}\frac{\sqrt{(p_{X3}G_X)^2+(p_{Y3}G_Y)^2}}{p_{Z3}G_Z}, \text{ and}$$

$$\phi_3 = \tan^{-1}\left(\frac{p_{Y3}G_Y}{p_{X3}G_X}\right);$$

(ii) a phase encoding gradient for the slice is given in the $(\zeta_1,\zeta_2,\zeta_3)$ coordinate system by:

$$G_2=(p_{X2}G_X, p_{Y2}G_Y, p_{Z2}G_Z) \text{ such that } \hat{\zeta}_3\cdot\hat{\zeta}_2=0,$$

where $(p_{X2}, p_{Y2}, p_{Z2})$ are gradient strength coefficients of the X, Y and Z gradient magnets $(G_X, G_Y, G_Z)$, respectively, and the axis direction of the phase encoding gradient is:

$$\hat{\zeta}_2 = (\sin\theta_2\cos\phi_2, \sin\theta_2\sin\phi_2, \cos\theta_2)$$

where $$\theta_2 = \tan^{-1}\frac{\sqrt{(p_{X2}G_X)^2+(p_{Y2}G_Y)^2}}{p_{Z2}G_Z}, \text{ and}$$

$$\phi_2 = \tan^{-1}\left(\frac{p_{Y2}G_Y}{p_{X2}G_X}\right); \text{ and}$$

(iii) a read gradient for the slice is given in the $(\zeta_1,\zeta_2,\zeta_3)$ coordinate system by:

$$G_1=(p_{X1}G_X, p_{Y1}G_Y, p_{Z1}G_Z), \text{ such that } \hat{\zeta}_3\cdot\hat{\zeta}_1=0,$$

where $(p_{X1}, p_{Y1}, P_{Z1})$ are gradient strength coefficients of the X, Y and Z gradient magnets $(G_X, G_Y, G_Z)$, respectively, and the axis direction of the read gradient is:

$$\hat{\zeta}_1 = (\sin\theta_1\cos\phi_1, \sin\theta_1\sin\phi_1, \cos\theta_1)$$

where $$\theta_1 = \tan^{-1}\frac{\sqrt{(p_{X1}G_X)^2+(p_{Y1}G_Y)^2}}{p_{Z1}G_Z}, \text{ and}$$

$$\phi_1 = \tan^{-1}\left(\frac{p_{Y1}G_Y}{p_{X1}G_X}\right);$$

(C) producing a corrected image function $\rho(\zeta_1',\zeta_2')$ from the uncorrected image function $\rho(\zeta_1,\zeta_2)$, where the coordinates $(\zeta_1',\zeta_2')$ represent a corrected position in the $(\zeta_1,\zeta_2,\zeta_3)$ coordinate system for the value of the image function at $(\zeta_1,\zeta_2)$, said $(\zeta_1',\zeta_2')$ coordinates being determined using an iterative mapping which employs coefficients of spherical harmonic expansions for the magnetic fields produced by the X, Y, and Z gradient magnets (the "spherical harmonic coefficients").

51. The method of claim 50 wherein:
the iterative mapping is of the form:

$$\begin{cases} \zeta_1' = \zeta_1 - \eta_1(\zeta_1',\zeta_2') \\ \zeta_2' = \zeta_2 - \eta_2(\zeta_1',\zeta_2') \end{cases}$$

where $$\begin{cases} \zeta_{1(1)}' = \zeta_1 - \eta_1(\zeta_1,\zeta_2) \\ \zeta_{2(1)}' = \zeta_2 - \eta_2(\zeta_1,\zeta_2) \end{cases}, \begin{cases} \zeta_{1(2)}' = \zeta_1 - \eta_1(\zeta_{1(1)}',\zeta_{2(1)}') \\ \zeta_{2(2)}' = \zeta_2 - \eta_2(\zeta_{1(1)}',\zeta_{2(1)}') \end{cases}, \ldots,$$

$$\begin{cases} \zeta_{1(n)}' = \zeta_1 - \eta_1(\zeta_{1(n-1)}',\zeta_{2(n-1)}') \\ \zeta_{2(n)}' = \zeta_2 - \eta_2(\zeta_{1(n-1)}',\zeta_{2(n-1)}') \end{cases}$$

where n is the iteration number and $\eta_1(\zeta_1,\zeta_2)=\eta_1(\zeta_1,\zeta_2,\zeta_3)$ and $\eta_2(\zeta_1,\zeta_2)=\eta_2(\zeta_1,\zeta_2,\zeta_3)$ are given by:

$$\begin{cases} \eta_1(\zeta_1,\zeta_2,\zeta_3) = \dfrac{B_1^N(r,\theta,\phi)}{G_1^L\cdot\hat{\zeta}_1} \\ \eta_2(\zeta_1,\zeta_2,\zeta_3) = \dfrac{B_2^N(r,\theta,\phi)}{G_2^L\cdot\hat{\zeta}_2} \end{cases}$$

(a) r, $\theta$ and $\phi$ are defined relative to the same origin as the $\zeta_1$, $\zeta_2$ and $\zeta_3$ coordinate system and are given by:
(i) $r=r_0+A\cdot(\zeta-\zeta_0)$; and
(ii)

$$\left(r = \sqrt{x^2+y^2+z^2}, \quad \theta = \tan^{-1}\left(\frac{\sqrt{x^2+y^2}}{z}\right), \quad \phi = \tan^{-1}\left(\frac{y}{x}\right)\right);$$

(b) $(G_1^L, G_2^L)$ represent the linear part of the gradients $(G_1, G_2)$ of the magnetic fields produced by the X, Y, and Z gradient magnets; and (c)

$$\begin{cases} B_1^N(r,\theta,\phi) = \\ p_{X1}\left(B_{X(0,0)}(r,\theta,\phi) + B_{X(1,0)}(r,\theta,\phi) + \sum_{n=2}\sum_m B_{X(n,m)}(r,\theta,\phi)\right) + \\ p_{Y1}\left(B_{Y(0,0)}(r,\theta,\phi) + B_{Y(1,0)}(r,\theta,\phi) + \sum_{n=2}\sum_m B_{Y(n,m)}(r,\theta,\phi)\right) + \\ p_{Z1}\left(B_{Z(0,0)}(r,\theta,\phi) + B_{Z(1,1)}(r,\theta,\phi) + \sum_{n=2}\sum_m B_{Z(n,m)}(r,\theta,\phi)\right) \\ B_2^N(r,\theta,\phi) = \\ p_{X2}\left(B_{X(0,0)}(r,\theta,\phi) + B_{X(1,0)}(r,\theta,\phi) + \sum_{n=2}\sum_m B_{X(n,m)}(r,\theta,\phi)\right) + \\ p_{Y2}\left(B_{Y(0,0)}(r,\theta,\phi) + B_{Y(1,0)}(r,\theta,\phi) + \sum_{n=2}\sum_m B_{Y(n,m)}(r,\theta,\phi)\right) + \\ p_{Z2}\left(B_{Z(0,0)}(r,\theta,\phi) + B_{Z(1,1)}(r,\theta,\phi) + \sum_{n=2}\sum_m B_{Z(n,m)}(r,\theta,\phi)\right) \end{cases}$$

represent the non-linear parts of the magnetic fields produced by the X, Y, and Z gradient magnets; where (i) m and n are the indices of the summations and satisfy the relationship $m \leq n$;

(ii) the $B_{V(n,m)}(r,\theta,\phi)$ are given by:

$$B_{V(n,m)}(r,\theta,\phi)=r^n[a_{V(n,m)}\cos(m\phi)+b_{V(n,m)}\sin(m\phi)]P_{(n,m)}(\cos\theta),$$

where the $P_{(n,m)}(\cos\theta)$ are the associated Legendre functions and the subscript V is one of X, Y, and Z; and (iii) $a_{V(n,m)}$ and $b_{V(n,m)}$ are the spherical harmonic coefficients, where the subscript V is one of X, Y, and Z.

52. The method of claim 51 wherein the iterative mapping is continued until the following condition is satisfied:

$$\frac{\sqrt{(\zeta'_{1(n)}-\zeta'_{1(n-1)})^2+(\zeta'_{2(n)}-\zeta'_{2(n-1)})^2}}{\sqrt{(\zeta'_{1(n)}-\zeta_1)^2+(\zeta'_{2(n)}-\zeta_2)^2}} \leq \varepsilon.$$

53. The method of claim 52 wherein:

$$\epsilon=10^{-3}.$$

54. The method of claim 53 wherein the iteration number is greater than or equal to 2 and less than or equal to 4.

55. The method of claim 50 further comprising displaying $\rho(\zeta_1', \zeta_2')$ as a corrected image.

56. The method of claim 50 further comprising producing an image function $\rho(\zeta_1'',\zeta_2'')$ having uniform pixel dimensions from $\rho(\zeta_1',\zeta_2')$ by performing an interpolation of the form:

$$\rho(\zeta_1'',\zeta_2'')=H(\zeta_1'',\zeta_2'',\rho(\zeta_1',\zeta_2'))$$

where H is an interpolation function and $(\zeta_1'',\zeta_2'')$ are uniformly distributed point coordinates in the $(\zeta_1,\zeta_2,\zeta_3)$ coordinate system.

57. The method of claim 56 wherein the interpolation comprises Lagrange interpolation, Newton interpolation, finite differences interpolation, Hermite interpolation, spline interpolation, or combinations thereof.

58. The method of claim 56 further comprising displaying $\rho(\zeta_1'',\zeta_2'')$ as a corrected image.

59. A method for forming an image of an object using a magnetic resonance imaging system which (i) comprises X, Y and Z gradient magnets and (ii) defines an origin of an (x, y, z) coordinate system (the "x, y, z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice of the object in two dimensions in data space using a linear combination of the X, Y, and Z gradient magnets;

(B) producing an uncorrected image function $\rho(\zeta_1,\zeta_2)$ from the MR data set by a process which comprises performing a two dimensional fast Fourier transform on said data set, where $\zeta_1$ and $\zeta_2$ are read and phase encoding coordinates, respectively, of a $(\zeta_1,\zeta_2,\zeta_3)$ coordinate system wherein:

(i) a slice select gradient is given in the $(\zeta_1,\zeta_2,\zeta_3)$ coordinate system by:

$$G_3=(p_{X3}G_X, p_{Y3}G_Y, p_{Z3}G_Z)$$

where ($p_{X3}$, $p_{Y3}$, $p_{Z3}$) are gradient strength coefficients of the X, Y, and Z gradient magnets ($G_X$, $G_Y$, $G_Z$), respectively, and the axis direction of the slice gradient is:

$$\hat{\zeta}_3=(\sin\theta_3\cos\phi_3, \sin\theta_3\sin\phi_3, \cos\theta_3)$$

where $$\theta_3=\tan^{-1}\frac{\sqrt{(p_{X3}G_X)^2+(p_{Y3}G_Y)^2}}{p_{Z3}G_Z}, \text{ and}$$

$$\phi_3=\tan^{-1}\left(\frac{p_{Y3}G_Y}{p_{X3}G_X}\right);$$

(ii) a phase encoding gradient for the slice is given in the $(\zeta_1,\zeta_2,\zeta_3)$ coordinate system by:

$$G_2=(p_{X2}G_X, p_{Y2}G_Y, p_{Z2}G_Z) \text{ such that } \hat{\zeta}_3\cdot\hat{\zeta}_2=0,$$

where ($p_{X2}$, $p_{Y2}$, $p_{Z2}$) are gradient strength coefficients of the X, Y and Z gradient magnets ($G_X$, $G_Y$, $G_Z$), respectively, and the axis direction of the phase encoding gradient is:

$$\hat{\zeta}_2=(\sin\theta_2\cos\phi_2, \sin\theta_2\sin\phi_2, \cos\theta_2)$$

where $$\theta_2=\tan^{-1}\frac{\sqrt{(p_{X2}G_X)^2+(p_{Y2}G_Y)^2}}{p_{Z2}G_Z}, \text{ and}$$

$$\phi_2=\tan^{-1}\left(\frac{p_{Y2}G_Y}{p_{X2}G_X}\right); \text{ and}$$

(iii) a read gradient for the slice is given in the $(\zeta_1, \zeta_2, \zeta_3)$ coordinate system by:

$$G_1=(p_{X1}G_X, p_{Y1}G_Y, p_{Z1}G_Z), \text{ such that } \hat{\zeta}_3\cdot\hat{\zeta}_1=0,$$

where ($p_{X1}$, $p_{Y1}$, $p_{Z1}$) are gradient strength coefficients of the X, Y and Z gradient magnets ($G_X$, $G_Y$, $G_Z$), respectively, and the axis direction of the read gradient is:

$$\hat{\zeta}_1=(\sin\theta_1\cos\phi_1, \sin\theta_1\sin\phi_1, \cos\theta_1)$$

where $$\theta_1=\tan^{-1}\frac{\sqrt{(p_{X1}G_X)^2+(p_{Y1}G_Y)^2}}{p_{Z1}G_Z}, \text{ and}$$

$$\phi_1=\tan^{-1}\left(\frac{p_{Y1}G_Y}{p_{X1}G_X}\right);$$

(C) producing a corrected image function $\rho(\zeta_1',\zeta_2')$ from the uncorrected image function $\rho(\zeta_1,\zeta_2)$, where the coordinates $(\zeta_1',\zeta_2')$ represent a corrected position in the $(\zeta_1,\zeta_2,\zeta_3)$ coordinate system for the value of the image function at $(\zeta_1,\zeta_2)$, said $(\zeta_1',\zeta_2')$ coordinates being determined by solving a system of non-linear equations so that an error function $f(\zeta_1',\zeta_2')$ satisfies the relationship:

$$\|f(\zeta_1',\zeta_2')\|\leq\epsilon$$

where $\epsilon$ is a predetermined constant;

wherein the system of non-linear equations employs coefficients of spherical harmonic expansions for the magnetic fields produced by the X, Y, and Z gradient magnets (the "spherical harmonic coefficients").

60. The method of claim 59 wherein the system of non-linear equations is solved iteratively using $\zeta_{1(0)}'=\zeta_1$ and $\zeta_{2(0)}'=\zeta_2$ as the initial $(\zeta_1',\zeta_2')$ values and an error function and system of non-linear equations of the form:

$$f(\zeta_1',\zeta_2') = \begin{cases} f_1(\zeta_1',\zeta_2',\zeta_3') = B_1^{LN}(r',\theta',\phi') - G_1^L \cdot \zeta_1 \cong 0 \\ f_2(\zeta_1',\zeta_2',\zeta_3') = B_2^{LN}(r',\theta',\phi') - G_2^L \cdot \zeta_2 \cong 0 \end{cases}$$

where:

(a) $(r',\theta',\phi')$ and $(\zeta_1',\zeta_2',\zeta_3')$ values are related by:

$$\left( r' = \sqrt{x'^2+y'^2+z'^2}, \theta' = \tan^{-1}\left(\frac{\sqrt{x'^2+y'^2}}{z'}\right), \phi' = \tan^{-1}\left(\frac{y'}{x'}\right)\right) \text{ and}$$

$$r' = r_0' + A \cdot (\zeta' - \zeta_0')$$

(b) $(G_1^L, G_2^L)$ represent the linear part of the gradients $(G_1, G_2)$ of the magnetic fields produced by the X, Y, and Z gradient magnets; and (c)

$$\begin{cases} B_1^{LN}(r,\theta,\phi) = p_{X1}\left(\sum_{n=0}\sum_m B_{X(n,m)}(r,\theta,\phi)\right) + \\ \qquad p_{Y1}\left(\sum_{n=0}\sum_m B_{Y(n,m)}(r,\theta,\phi)\right) + p_{Z1}\left(\sum_{n=0}\sum_m B_{Z(n,m)}(r,\theta,\phi)\right) \\ B_2^{LN}(r,\theta,\phi) = p_{X2}\left(\sum_{n=0}\sum_m B_{X(n,m)}(r,\theta,\phi)\right) + \\ \qquad p_{Y2}\left(\sum_{n=0}\sum_m B_{Y(n,m)}(r,\theta,\phi)\right) + p_{Z2}\left(\sum_{n=0}\sum_m B_{Z(n,m)}(r,\theta,\phi)\right) \end{cases}$$

represent the linear and non-linear parts of the magnetic fields produced by the X, Y, and Z gradient magnets, where (i) m and n are the indices of the summations and satisfy the relationship $m \leq n$;

(ii) the $B_{V(n,m)}(r',\theta',\phi')$ are given by:

$$B_{V(n,m)}(r',\theta',\phi')=r'^n[a_{V(n,m)}\cos(m\phi')+b_{V(n,m)}\sin(m\phi')]P_{(n,m)}(\cos\theta')$$

where the $P_{(n,m)}(\cos\theta')$ are the associated Legendre functions and the subscript V is one of X, Y, and Z; and (iii) $a_{V(n,m)}$ and $b_{V(n,m)}$ are the spherical harmonic coefficients, where the subscript V is one of X, Y, and Z.

61. The method of claim 60 wherein a Levenberg-Marquardt non-linear curve fitting technique is used in solving the system of non-linear equations.

62. The method of claim 60 wherein a non-linear minimization technique is used in solving the system of non-linear equations.

63. The method of claim 59 wherein:

$$\epsilon = R_{es} \times 10^{-3},$$

where $R_{es}$ is the resolution of the image given by:

$$R_{es} = A_{image}/N_{pix},$$

where $A_{image}$ is the area of the image and $N_{pix}$ is total number of pixels making up the image.

64. The method of claim 59 further comprising displaying $\rho(\zeta_1',\zeta_2')$ as a corrected image.

65. The method of claim 59 further comprising producing an image function $\rho(\zeta_1'',\zeta_2'')$ having uniform pixel dimensions from $\rho(\zeta_1',\zeta_2')$ by performing an interpolation of the form:

$$\rho(\zeta_1'',\zeta_2'')=H(\zeta_1'',\zeta_2'',\rho(\zeta_1',\zeta_2'))$$

where H is an interpolation function and $(\zeta_1'',\zeta_2'')$ are uniformly distributed point coordinates in the $(\zeta_1,\zeta_2,\zeta_3)$ coordinate system.

66. The method of claim 65 wherein the interpolation comprises Lagrange interpolation, Newton interpolation, finite differences interpolation, Hermite interpolation, spline interpolation, or combinations thereof.

67. The method of claim 65 further comprising displaying $\rho(\zeta_1'',\zeta_2'')$ as a corrected image.

68. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients $(G_X, G_Y, G_Z)$, respectively, said method comprising:

(A) acquiring a magnetic resonance signal data set (the "MR data set") for a slice of the object in two dimensions in data space using a linear combination of the X, Y, and Z gradient magnets, where the MR data set is of the form $s(m_1\Delta t_1, m_2\Delta t_2)$ where:

(i) $m_1$ and $m_2$ are respectively indices for the k-space data points in $\hat{\zeta}_1$ and $\hat{\zeta}_2$ directions, where $\zeta_1$ and $\zeta_2$ are read and phase encoding coordinates, respectively, of a $(\zeta_1,\zeta_2,\zeta_3)$ coordinate system wherein:

(a) a slice select gradient is given in the $(\zeta_1, \zeta_2, \zeta_3)$ coordinate system by:

$$G_3=(p_{X3}G_X, p_{Y3}G_Y, p_{Z3}G_Z)$$

where $(p_{X3}, p_{Y3}, p_{Z3})$ are gradient strength coefficients of the X, Y, and Z gradient magnets $(G_X, G_Y, G_Z)$, respectively, and the axis direction of the slice gradient is:

$$\hat{\zeta}_3 = (\sin\theta_3\cos\phi_3, \sin\theta_3\sin\phi_3, \cos\theta_3)$$

where $$\theta_3 = \tan^{-1}\frac{\sqrt{(p_{X3}G_X)^2+(p_{Y3}G_Y)^2}}{p_{Z3}G_Z}, \text{ and}$$

$$\phi_3 = \tan^{-1}\left(\frac{p_{Y3}G_Y}{p_{X3}G_X}\right);$$

(b) a phase encoding gradient for the slice is given in the $(\zeta_1,\zeta_2,\zeta_3)$ coordinate system by:

$$G_2=(p_{X2}G_X, p_{Y2}G_Y, p_{Z2}G_Z) \text{ such that } \hat{\zeta}_3 \cdot \hat{\zeta}_2 = 0,$$

where $(p_{X2}, p_{Y2}, p_{Z2})$ are gradient strength coefficients of the X, Y and Z gradient magnets $(G_X, G_Y, G_Z)$, respectively, and the axis direction of the phase encoding gradient is:

$$\hat{\zeta}_2 = (\sin\theta_2\cos\phi_2, \sin\theta_2\sin\phi_2, \cos\theta_2)$$

where $$\theta_2 = \tan^{-1}\frac{\sqrt{(p_{X2}G_X)^2+(p_{Y2}G_Y)^2}}{p_{Z2}G_Z}, \text{ and}$$

$$\phi_2 = \tan^{-1}\left(\frac{p_{Y2}G_Y}{p_{X2}G_X}\right); \text{ and}$$

(c) a read gradient for the slice is given in the $(\zeta_1,\zeta_2,\zeta_3)$ coordinate system by:

$$G_1=(p_{X1}G_X, p_{Y1}G_Y, p_{Z1}G_Z), \text{ such that } \hat{\zeta}_3 \cdot \hat{\zeta}_1 = 0,$$

where $(P_{X1}, P_{Y1}, p_{Z1})$ are gradient strength coefficients of the X, Y and Z gradient magnets $(G_X, G_Y, G_Z)$, respectively, and the axis direction of the read gradient is:

$$\hat{\zeta}_1 = (\sin\theta_1\cos\phi_1, \sin\theta_1\sin\phi_1, \cos\theta_1)$$

where $$\theta_1 = \tan^{-1}\frac{\sqrt{(p_{X1}G_X)^2+(p_{Y1}G_Y)^2}}{p_{Z1}G_Z}, \text{ and}$$

$$\phi_1 = \tan^{-1}\left(\frac{p_{Y1}G_Y}{p_{X1}G_X}\right); \text{ and}$$

(ii) $\Delta t_1$ and $\Delta t_2$ are respectively equivalent time steps in k-space for the $\hat{\zeta}_1$ and $\hat{\zeta}_2$ directions;

(B) producing an uncorrected image function $\rho(l_1\Delta\omega_1{}^L, l_2\Delta\omega_2{}^L)$ from the MR data set by a process which comprises performing a two dimensional fast Fourier transform on said data set, said uncorrected image function being in frequency space at a set of frequency points given by $(l_1\Delta\omega_1{}^L, l_2\Delta\omega_2{}^L)$ where:

(i) $l_1$ and $l_2$ are indices for the frequency points in the $\omega_1{}^L$ and $\omega_2{}^L$ directions, respectively;

(ii) $\Delta\omega_1{}^L$ and $\Delta\omega_2{}^L$ are frequency steps in the $\omega_1{}^L$ and $\omega_2{}^L$ directions, respectively;

(iii) $\omega_1{}^L=\gamma G_1{}^L\cdot\zeta_1$, $\omega_2{}^L=\gamma G_2{}^L\cdot\zeta_2$, where:
  (a) $\gamma$ is a constant; and
  (b) $(G_1{}^L, G_2{}^L)$ represent the linear parts of the gradients $(G_1, G_2)$ of the magnetic fields produced by the X, Y, and Z gradient magnets;

(iv) the range of $l_1$ is selected so that $l_2\cdot\Delta\omega_1{}^L$ spans the frequency range that would arise from the $G_1$ gradient if that gradient were purely linear in the $\hat{\zeta}_1$ direction and the range of $l_1$ is selected so that $l_1\cdot\Delta\omega_1{}^L$ spans the frequency range that would arise from the $G_2$ gradient if that gradient were purely linear field in the $\hat{\zeta}_2$ direction; and (v) the fast Fourier transform is of the form:

$$\rho(l_1\Delta\omega_1^L, l_2\Delta\omega_2^L) = \sum_{m_2}\sum_{m_1} s(m_1\Delta t_1, m_2\Delta t_2)e^{i(l_1\Delta\omega_1^L\cdot m_1\Delta t_1 + l_2\Delta\omega_2^L\cdot m_2\Delta t_2)}\Delta t_1\Delta t_2$$

(C) producing a corrected image function $\rho(\zeta_1',\zeta_2')$ in frequency space at $(\zeta_1', \zeta_2', \zeta_3')$ in the $(\zeta_1, \zeta_2, \zeta_3)$ coordinate system from the uncorrected image function $\rho(l_1\Delta\omega_1{}^L, l_2\Delta\omega_2{}^L)$ using an interpolation function L in frequency space of the form:

$$\rho(\omega_1^N(\zeta_1',\zeta_2',\zeta_3'),\omega_2^N(\zeta_1',\zeta_2',\zeta_3'))=L(\omega_1^N,\omega_2^N,\rho(l_1\Delta\omega_1^L,l_2\Delta\omega_2^L))$$

where:

(i) $\rho(\omega_1^N(\zeta_1',\zeta_2',\zeta_3'),\omega_2^N(\zeta_1',\zeta_2',\zeta_3'))$ is the desired $\rho(\zeta_1', \zeta_2')$; and (ii) $G_1{}^L$, $G_2{}^L$, $\omega_1^N(\zeta_1',\zeta_2',\zeta_3')$, and $\omega_2^N(\zeta_1',\zeta_2',\zeta_3')$ are determined using coefficients of spherical harmonic expansions for the magnetic fields produced by the X, Y, and Z gradient magnets (the "spherical harmonic coefficients").

69. The method of claim 68 wherein:

(a) $a_{V(n,m)}$ and $b_{V(n,m)}$ are the spherical harmonic coefficients, where the subscript V is one of X, Y, and Z;

(b) $G_1{}^L=p_{X1}a_{X(1,1)}+p_{Y1}a_{Y(1,1)}+p_{Z1}a_{Z(1,0)}$, and $$G_2{}^L=p_{X2}a_{X(1,1)}+p_{Y2}a_{Y(1,1)}+p_{Z2}a_{Z(1,0)}; \text{ and}$$

(c) $\omega_1^N(\zeta_1',\zeta_2',\zeta_3')$ and $\omega_2^N(\zeta_1',\zeta_2',\zeta_3')$ are given by:

$$\begin{cases}\omega_1^N(\zeta_1',\zeta_2',\zeta_3') = \gamma(\zeta_1' + \eta_1(\zeta_1',\zeta_2',\zeta_3'))(G_1^L\cdot\hat{\zeta}_1) \\ \omega_2^N(\zeta_1',\zeta_2',\zeta_3') = \gamma(\zeta_2' + \eta_2(\zeta_1',\zeta_2',\zeta_3'))(G_2^L\cdot\hat{\zeta}_2)\end{cases}$$

where $\eta_1(\zeta_1',\zeta_2',\zeta_3')$ and $\eta_2(\zeta_1',\zeta_2',\zeta_3')$ are given by:

$$\begin{cases}\eta_1(\zeta_1',\zeta_2',\zeta_3') = \dfrac{B_1^N(r',\theta',\phi')}{G_1^L\cdot\hat{\zeta}_1} \\ \eta_2(\zeta_1',\zeta_2',\zeta_3') = \dfrac{B_2^N(r',\theta',\phi')}{G_2^L\cdot\hat{\zeta}_2}\end{cases}$$

where $$\begin{cases}B_1^N(r,\theta,\phi) = \\ p_{X1}\left(B_{X(0,0)}(r,\theta,\phi)+B_{X(1,0)}(r,\theta,\phi)+\sum_{n=2}\sum_m B_{X(n,m)}(r,\theta,\phi)\right)+ \\ p_{Y1}\left(B_{Y(0,0)}(r,\theta,\phi)+B_{Y(1,0)}(r,\theta,\phi)+\sum_{n=2}\sum_m B_{Y(n,m)}(r,\theta,\phi)\right)+ \\ p_{Z1}\left(B_{Z(0,0)}(r,\theta,\phi)+B_{Z(1,1)}(r,\theta,\phi)+\sum_{n=2}\sum_m B_{Z(n,m)}(r,\theta,\phi)\right) \\ B_2^N(r,\theta,\phi) = \\ p_{X2}\left(B_{X(0,0)}(r,\theta,\phi)+B_{X(1,0)}(r,\theta,\phi)+\sum_{n=2}\sum_m B_{X(n,m)}(r,\theta,\phi)\right)+ \\ p_{Y2}\left(B_{Y(0,0)}(r,\theta,\phi)+B_{Y(1,0)}(r,\theta,\phi)+\sum_{n=2}\sum_m B_{Y(n,m)}(r,\theta,\phi)\right)+ \\ p_{Z2}\left(B_{Z(0,0)}(r,\theta,\phi)+B_{Z(1,1)}(r,\theta,\phi)+\sum_{n=2}\sum_m B_{Z(n,m)}(r,\theta,\phi)\right)\end{cases}$$

represent the non-linear parts of the magnetic fields produced by the X, Y, and Z gradient magnets, where:

(i) m and n are the indices of the summations and satisfy the relationship $m \leq n$;

(ii) $B_{V(n,m)}(r',\theta',\phi')$ is given by:

$$B_{V(n,m)}(r',\theta',\phi')=r'^n[a_{V(n,m)}\cos(m\phi')+b_{V(n,m)}\sin(m\phi')]P_{(n,m)}(\cos\theta')$$

where the $P_{(n,m)}(\cos\theta')$ are associated Legendre functions and the subscript V is one of X, Y, and Z; and (iii) $(r', \theta', \phi')$ and $(\zeta_1', \zeta_2', \zeta_3')$ values are related by:

$$\left(r' = \sqrt{x'^2+y'^2+z'^2}, \theta' = \tan^{-1}\left(\frac{\sqrt{x'^2+y'^2}}{z'}\right),\right.$$

$$\phi' = \tan^{-1}\left(\frac{y'}{x'}\right)\right) \text{ and}$$

$$r' = r_0' + A\cdot(\zeta'-\zeta_0').$$

70. The method of claim 68 wherein the interpolation function L is a sinc function such that:

$$L(\omega_1^N, \omega_2^N, \rho(l_1\Delta\omega_1^L, l_2\Delta\omega_2^L)) = \sum_{l_2}\sum_{l_1} \rho(l_1\Delta\omega_1^L, l_2\Delta\omega_2^L) \operatorname{sinc}\left(\frac{\omega_1^N}{\Delta\omega_1^L} - l_1, \frac{\omega_2^N}{\Delta\omega_2^L} - l_2\right).$$

71. The method of claim 68 wherein the interpolation function L is of the form:

$$L(\omega_1^N, \omega_2^N, \rho(l_1\Delta\omega_1^L, l_2\Delta\omega_2^L)) = \sum_{l_2}\sum_{l_1} C_{(l_1,l_2)}\psi_{1(l_1)}(\omega_1^N)\psi_{2(l_2)}(\omega_2^N)$$

where:
(a) $\psi_{1(l_1)}$ and $\psi_{2(l_2)}$ are orthogonal bases functions; and
(b) the $C_{(l_1,l_2)}$ are coefficients which satisfy the matrix equation:

$$AC = \rho$$

where the vector C is of the form:

$$C = [C_{(1,1)} C_{(2,1)} \ldots C_{(l_1, l_2)}]^T$$

the vector $\rho$ is of the form:

$$\rho[\rho(\omega_{1(1)}^L, \omega_{2(1)}^L)\ \rho(\omega_{1(2)}^L, \omega_{2(1)}^L) \ldots \rho(\omega_{1(l_1)}^L, \omega_{2(l_2)}^L)]^T$$

and the matrix A is of the form:

$$\begin{bmatrix} \psi_{1(1)}(\omega_{1(1)}^L)\psi_{2(1)}(\omega_{2(1)}^L) & \psi_{1(2)}(\omega_{1(1)}^L)\psi_{2(1)}(\omega_{2(1)}^L) & \cdots & \psi_{1(l_1)}(\omega_{1(1)}^L)\psi_{2(l_2)}(\omega_{2(1)}^L) \\ \psi_{1(1)}(\omega_{1(2)}^L)\psi_{2(1)}(\omega_{2(1)}^L) & \psi_{1(2)}(\omega_{1(2)}^L)\psi_{2(1)}(\omega_{2(1)}^L) & \cdots & \psi_{1(l_1)}(\omega_{1(2)}^L)\psi_{2(l_2)}(\omega_{2(1)}^L) \\ \vdots & \vdots & \ddots & \vdots \\ \psi_{1(1)}(\omega_{1(l_1)}^L)\psi_{2(1)}(\omega_{2(l_2)}^L) & \psi_{1(2)}(\omega_{1(l_1)}^L)_2\psi_{2(1)}(\omega_{2(l_2)}^L) & \cdots & \psi_{1(l_1)}(\omega_{1(l_1)}^L)\psi_{2(l_2)}(\omega_{2(l_2)}^L) \end{bmatrix}.$$

72. The method of claim 71 wherein the interpolation comprises Lagrange's interpolation, Newton interpolation, finite difference interpolation, Hermite interpolation, spline interpolation, or combinations thereof.

73. The method of claim 71 wherein the interpolation is applied to all of the data points obtained by performing the two dimensional fast Fourier transform on the MR data set.

74. The method of claim 71 wherein the interpolation is applied to a subset of the data points obtained by performing the two dimensional fast Fourier transform on the MR data set, said subset being in the vicinity of a region of interest of the object being imaged.

75. The method of claim 68 further comprising displaying $\rho(\zeta_1', \zeta_2')$ as a corrected image.

76. The method of claim 68 further comprising producing an image function $\rho(\zeta_1'', \zeta_2'')$ having uniform pixel dimensions from $\rho(\zeta_1', \zeta_2')$ by performing an interpolation of the form:

$$\rho(\zeta_1'', \zeta_2'') = H(\zeta_1'', \zeta_2'', \rho(\zeta_1', \zeta_2'))$$

where H is an interpolation function and $(\zeta_1'', \zeta_2'')$ are uniformly distributed point coordinates in the $(\zeta_1, \zeta_2, \zeta_3)$ coordinate system.

77. The method of claim 76 wherein the interpolation comprises Lagrange interpolation, Newton interpolation, finite differences interpolation, Hermite interpolation, spline interpolation, or combinations thereof.

78. The method of claim 76 further comprising displaying $\rho(\zeta_1'', \zeta_2'')$ as a corrected image.

79. A method for forming an image of an object using a magnetic resonance imaging system which defines an origin of a coordinate system and comprises (i) a main magnet and (ii) X, Y and Z gradient magnets, said method comprising:
(A) acquiring a magnetic resonance signal data set (the "MR data set") for the object in data space using the X, Y, and Z gradient magnets;
(B) producing an uncorrected image function from the MR data set; and
(C) producing a corrected image function from the uncorrected image function using at least one coefficient selected from the group consisting of:
(i) the spherical harmonic coefficients a(0,0), b(0,0), a(1, 0), b(1,0) and b(1,1) for the X-gradient magnet or corresponding coefficients that arise if a basis set other than spherical harmonics is used to solve Laplace's equation;
(ii) the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation; and
(iii) the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

80. A method for forming an image of an object using a magnetic resonance imaging system which defines an origin of a coordinate system and comprises (i) a main magnet and (ii) X, Y and Z gradient magnets, said method comprising:
(A) acquiring a magnetic resonance signal data set (the "MR data set") for the object in data space using the X, V, and Z gradient magnets;
(B) producing an uncorrected image function from the MR data set; and
(C) producing a corrected image function from the uncorrected image function using at least one coefficient selected from the group consisting of:
(i) the spherical harmonic coefficients a(0,0), b(0,0), a(1, 0), b(1,0) and b(1,1) for the X-gradient magnet or corresponding coefficients that arise if a basis set other than spherical harmonics is used to solve Lapiace's equation;
(ii) the spherical harmonic coefficients a(0,0), b(0,0), a(1,0), a(1,1), and b(1,0) for the Y-gradient magnet or corresponding coefficients that arise if a basis set other than soherical harmonics is used to solve Laplace's equation; and
(iii) the spherical harmonic coefficients a(0,0), b(0,1), a(1,1), b(1,0) and b(1,1) for the Z-gradient magnet or corresponding coefficients that arise if a basis set other than spherical harmonics is used to solve Laplace's equation;
wherein step (B) comprises performing a fast Fourier transform on the MR data set.

81. The method of claim 79 or 80 further comprising displaying the corrected image produced in step (C).

82. The method of claim 79 or 80 wherein the at least one coefficient used in step (C) comprises at least one of the spherical harmonic coefficients a(0,0), b(0,0), a(1,0), b(1.0) and b(1,1) for the X-gradient magnet or corresponding coefficients that arise if a basis set other than spherical harmonics is used to solve Laplace's equation.

83. The method of claim 79 or 80 wherein the at least one coefficient used in step (C) comprises all of the spherical harmonic coefficients a(0,0), b(0,0), a(1,0), b(1.0) and b(1,1) for the X-gradient magnet or corresponding coefficients that arise if a basis set other than spherical harmonics is used to solve Laplace's equation.

84. The method of claim 79 or 80 wherein the at least one coefficient used in step (C) comprises at least one of the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation.

85. The method of claim 79 or 80 wherein the at least one coefficient used in step (C) comprises all of the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation.

86. The method of claim 79 or 80 wherein the at least one coefficient used in step (C) comprises at least one of the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

87. The method of claim 79 or 80 wherein the at least one coefficient used in step (C) comprises all of the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

88. The method of claim 79 or 80 wherein the at least one coefficient used in step (C) comprises at least one of the spherical harmonic coefficients a(0,0), b(0,0), a(1,0), b(1.0) and b(1,1) for the X-gradient magnet or corresponding coefficients that arise if a basis set other than spherical harmonics is used to solve Laplace's equation, at least one of the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation, and at least one of the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

89. The method of claim 79 or 80 wherein the at least one coefficient used in step (C) comprises all of the spherical harmonic coefficients a(0,0), b(0,0), a(1,0), b(1,0) and b(1,1) for the X-gradient magnet or corresponding coefficients that arise if a basis set other than spherical harmonics is used to solve Laplace's equation, all of the spherical harmonic coefficients a(0,0), b(0,0), a(1,0), a(1,1), and b(1,0) for the Y-gradient magnet or corresponding coefficients that arise if a basis set other than spherical harmonics is used to solve Laplace's equation, and all of the spherical harmonic coefficients a(0,0), b(0,0), a(1,1), b(1,0) and b(1,1) for the Z-gradient magnet or corresponding coefficients that arise if a basis set other than spherical harmonics is used to solve Laplace's equation.

90. The method of claim 79 or 80 wherein said at least one coefficient or a numerical value derived therefrom is stored in a computer memory and retrieved from the memory during the performance of step (C).

91. The method of claim 79 or 80 wherein the MR data set acquired in step (A) comprises three dimensional data for the object.

92. The method of claim 79 or 80 wherein the MR data set acquired in step (A) comprises two dimensional data for the object.

93. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function ρ(x,y,z) from the MR data set by a process which comprises performing a three dimensional fast Fourier transform on said data set; and (C) producing a corrected image function ρ(x',y',z') from the uncorrected image function ρ(x,y,z), where the coordinates (x',y',z') represent a corrected position in the x,y,z-coordinate system for the value of the image function at (x,y,z), said (x',y',z') coordinates being determined using an iterative mapping which employs coefficients of expansions for the magnetic fields produced by the X, Y, and Z gradient magnets, said expansions and coefficients being for a basis set that satisfies Laplace's equation.

94. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets;

(B) producing an uncorrected image function ρ(x,y,z) from the MR data set by a process which comprises performing a three dimensional fast Fourier transform on said data set; and (C) producing a corrected image function ρ(x',y',z') from the uncorrected image function ρ(x,y,z), where the coordinates (x',y',z') represent a corrected position in the x,y,z-coordinate system for the value of the image function at (x,y,z), said (x',y',z') coordinates being determined by solving a system of non-linear equations so that an error function f(x',y',z') satisfies the relationship:

$$\|f(x',y',z')\| \leq \epsilon,$$

where $\epsilon$ is a predetermined constant;

wherein the system of non-linear equations employs coefficients of expansions for the magnetic fields produced by the X, Y, and Z gradient magnets, said expansions and coefficients being for a basis set that satisfies Laplace's equation.

95. The method of claim 94 wherein a Levenberg-Marquardt non-linear curve fitting technique is used in solving the system of non-linear equations.

96. The method of claim 94 wherein a non-linear minimization technique is used in solving the system of non-linear equations.

97. The method of claim 94 wherein:

$$\epsilon = R_{es} \times 10^{-3},$$

where $R_{es}$ is the resolution of the image given by:

$$R_{es} = A_{image}/N_{pix},$$

where $A_{image}$ is the area of the image and $N_{pix}$ is total number of pixels making up the image.

98. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for the object in three dimensions in data space using the X, Y, and Z gradient magnets, where the MR data set is of the form $s(m_X \Delta t_X, m_Y \Delta t_Y, m_Z \Delta t_Z)$ where:

(i) $m_X$, $m_Y$ and $m_Z$ are indices for the data points in the x, y, and z directions, respectively; and (ii) $\Delta t_X$, $\Delta t_Y$ and $\Delta t_Z$ are equivalent time steps in the x, y, and z directions, respectively;

(B) producing an uncorrected image function $\rho(l_X \Delta \omega_X^L, l_Y \Delta \omega_Y^L, l_Z \Delta \omega_Z^L)$ from the MR data set by a process which comprises performing a three dimensional fast Fourier transform on said data set, said uncorrected image function being in frequency space at a set of frequency points given by $(l_X \Delta \omega_X^L, l_Y \Delta \omega_Y^L, l_Z \Delta \omega_Z^L)$ where:

(i) $l_X$, $l_Y$ and $l_Z$ are indices for the frequency points in the $\omega_X^L$, $\omega_Y^L$ and $\omega_Z^L$ directions, respectively;

(ii) $\Delta \omega_X^L$, $\Delta \omega_Y^L$ and $\Delta \omega_Z^L$ are frequency steps in the $\omega_X^L$, $\omega_Y^L$ and $\omega_Z^L$ directions, respectively;

(iii) $\omega_X^L = \gamma x G_X^L$, $\omega_Y^L = \gamma y G_Y^L$, $\omega_Z^L = \gamma z G_Z^L$, where:

(a) $\gamma$ is a constant; and (b) $G_X^L$, $G_Y^L$, and $G_Z^L$ represent the linear parts of the gradients ($G_X$, $G_Y$, $G_Z$) of the magnetic fields produced by the X, Y, and Z gradient magnets, respectively;

(iv) the ranges of $l_X$, $l_Y$, and $l_Z$ are selected so that $l_X \cdot \Delta \omega_X^L$, $l_Y \cdot \Delta \omega_Y^L$, and $l_Z \cdot \Delta \omega_Z^L$ respectively span the frequency ranges that would arise from the X, Y, and Z gradient magnets if those magnets produced purely linear gradient fields in the x, y, and z directions of the x,y,z-coordinate system; and (v) the fast Fourier transform is of the form:

$$\rho(l_X \Delta \omega_X^L, l_Y \Delta \omega_Y^L, l_Z \Delta \omega_Z^L) = \sum_{m_X} \sum_{m_Y} \sum_{m_Z} s(m_X \Delta t_X, m_Y \Delta t_Y, m_Z \Delta t_Z)$$
$$e^{i(l_X \Delta \omega_X^L \cdot m_X \Delta t_X + l_Y \Delta \omega_Y^L \cdot m_Y \Delta t_Y + l_Z \Delta \omega_Z^L \cdot m_Z \Delta t_Z)} \Delta t_X \Delta t_Y \Delta t_Z$$

(C) producing a corrected image function $\rho(x',y',z')$ at $(x',y',z')$ in the x,y,z-coordinate system from the uncorrected image function $\rho(l_X \Delta \omega_X^L, l_Y \Delta \omega_Y^L, l_Z \Delta \omega_Z^L)$ using an interpolation function L in frequency space of the form:

$$\rho(\omega_X^N, \omega_Y^N, \omega_Z^N) = L(\omega_X^N, \omega_Y^N, \omega_Z^N, \rho(l_X \Delta \omega_X^L, l_Y \Delta \omega_Y^L, l_Z \Delta \omega_Z^L))$$

where:

(i) $\omega_X^N$, $\omega_Y^N$, and $\omega_Z^N$ are each a function of $(x',y',z')$; and (ii) $\rho(\omega_X^N, \omega_Y^N, \omega_Z^N)$ equals the desired $\rho(x',y',z')$;

wherein $G_X^L$, $G_Y^L$, $G_Z^L$, $\omega_X^N$, $\omega_Y^N$, and $\omega_Z^N$ are determined using coefficients of expansions for the magnetic fields produced by the X, Y, and Z gradient magnets, said expansions and coefficients being for a basis set that satisfies Laplace's equation.

99. The method of claim 98 wherein the interpolation function L is a sinc function such that:

$$L(\omega_X^N, \omega_Y^N, \omega_Z^N, \rho(l_X \Delta \omega_X^L, l_Y \Delta \omega_Y^L, l_Z \Delta \omega_Z^L)) =$$
$$\sum_{l_Z} \sum_{l_Y} \sum_{l_X} \rho(l_X \Delta \omega_X^L, l_Y \Delta \omega_Y^L, l_Z \Delta \omega_Z^L)$$
$$\text{sinc}\left(\frac{\omega_X^N}{\Delta \omega_X^L} - l_X, \frac{\omega_Y^N}{\Delta \omega_Y^L} - l_Y, \frac{\omega_Z^N}{\Delta \omega_Z^L} - l_Z\right).$$

100. The method of claim 98 wherein the interpolation function L is of the form:

$$L(\omega_X^N, \omega_Y^N, \omega_Z^N, \rho(l_X \Delta \omega_X^L, l_Y \Delta \omega_Y^L, l_Z \Delta \omega_Z^L)) =$$
$$\sum_{l_Z} \sum_{l_Y} \sum_{l_X} C_{(l_X, l_Y, l_Z)} \psi_{X(l_X)}(\omega_X^N) \psi_{Y(l_Y)}(\omega_Y^N) \psi_{Z(l_Z)}(\omega_Z^N)$$

where:

(a) $\psi_{X(l_X)}$, $\psi_{Y(l_Y)}$ and $\psi_{Z(l_Z)}$ are orthogonal bases functions; and (b) the $C_{(l_X, l_Y, l_Z)}$ are coefficients which satisfy the matrix equation:

$$AC = \rho$$

where the vector C is of the form:

$$C = [C_{(1,1,1)} \, C_{(2,1,1)} \, \ldots \, C_{(l_X, l_Y, l_Z)}]^T$$

the vector $\rho$ is of the form:

$$\rho = [\rho(\omega_{X(1)}^L, \omega_{Y(1)}^L, \omega_{Z(1)}^L) \, \rho(\omega_{X(2)}^L, \omega_{Y(1)}^L, \omega_{Z(1)}^L) \, \ldots \, \rho(\omega_{X(l_X)}^L, \omega_{Y(l_Y)}^L, \omega_{Z(l_Z)}^L)]^T$$

and the matrix A is of the form:

$$\begin{bmatrix} \beta_{(1,1)} & \beta_{(1,2)} & \cdots & \beta_{(1,q)} \\ \beta_{(2,1)} & \beta_{(2,2)} & \cdots & \beta_{(2,q)} \\ \vdots & \vdots & \ddots & \vdots \\ \beta_{(q,1)} & \beta_{(q,2)} & \cdots & \beta_{(q,q)} \end{bmatrix}$$

where $\beta_{(1,1)} = \psi_{X(1)}(\omega_{X(1)}^L) \psi_{Y(1)}(\omega_{X(1)}^L) \psi_{Z(1)}(\omega_{Z(1)}^L)$, $\beta_{(1,2)} = \psi_{X(2)}(\omega_{X(1)}^L) \psi_{Y(1)}(\omega_{X(1)}^L) \psi_{Z(1)}(\omega_{Z(1)}^L)$, $\vdots$ $\beta_{(1,q)} = \psi_{X(l_X)}(\omega_{X(1)}^L) \psi_{Y(l_Y)}(\omega_{Y(1)}^L) \psi_{Z(l_Z)}(\omega_{Z(1)}^L)$;

$\beta_{(2,1)} = \psi_{X(1)}(\omega_{X(2)}^L) \psi_{Y(1)}(\omega_{Y(1)}^L) \psi_{Z(1)}(\omega_{Z(1)}^L)$, $\beta_{(2,2)} = \psi_{X(2)}(\omega_{X(2)}^L) \psi_{Y(1)}(\omega_{Y(1)}^L) \psi_{Z(1)}(\omega_{Z(1)}^L)$, $\vdots$ $\beta_{(2,q)} = \psi_{X(l_X)}(\omega_{X(2)}^L) \psi_{Y(l_Y)}(\omega_{Y(1)}^L) \psi_{Z(l_Z)}(\omega_{Z(1)}^L)$;

$\vdots$ $\beta_{(q,1)} = \psi_{X(1)}(\omega_{X(l_X)}^L) \psi_{Y(1)}(\omega_{Y(l_Y)}^L) \psi_{Z(1)}(\omega_{Z(l_Z)}^L)$, $\beta_{(q,2)} = \psi_{X(2)}(\omega_{X(l_X)}^L) \psi_{Y(1)}(\omega_{Y(l_Y)}^L) \psi_{Z(1)}(\omega_{Z(l_Z)}^L)$, $\beta_{(q,q)} = \psi_{X(l_X)}(\omega_{X(l_X)}^L) \psi_{Y(l_Y)}(\omega_{Y(l_Y)}^L) \psi_{Z(l_Z)}(\omega_{Z(l_Z)}^L)$, where $q \leq [l_X \times l_Y \times l_Z]_{max}$.

101. The method of claim 100 wherein the interpolation comprises Lagrange's interpolation, Newton interpolation, finite difference interpolation, Hermite interpolation, spline interpolation, or combinations thereof.

102. The method of claim 100 wherein the interpolation is applied to all of the data points obtained by performing the three dimensional fast Fourier transform on the MR data set.

103. The method of claim 100 wherein the interpolation is applied to a subset of the data points obtained by performing the three dimensional fast Fourier transform on the MR data set, said subset being in the vicinity of a region of interest of the object being imaged.

104. The method of claim 98 wherein:
   (a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1, \zeta_2, \zeta_3)$ and the transformation between the x,y,z and $\zeta$ coordinate systems (the "xyz-$\zeta$ transformation") being of the form:

$$r = A\zeta \text{ and } \zeta = A^{-1}r$$

where $$r = [x, y, z]^T,$$

$$\zeta = [\zeta_1, \zeta_2, \zeta_3]^T, \text{ and}$$

$$A = \begin{bmatrix} c_{11} & c_{12} & c_{13} \\ c_{21} & c_{22} & c_{23} \\ c_{31} & c_{32} & c_{33} \end{bmatrix} \text{ (the "A matrix"),}$$

where the c's are direction cosines;
   (b) in step (B), the three dimensional fast Fourier transform is performed on the MR data set in the $\zeta$ coordinate system to produce an uncorrected image function in $(\omega_{\zeta_1}, \omega_{\zeta_2}, \omega_{\zeta_3})$ frequency space, and thereafter, an uncorrected image function in $(\omega_X, \omega_Y, \omega_Z)$ frequency space is produced by a transformation of the $(\omega_{\zeta_1}, \omega_{\zeta_2}, \omega_{\zeta_3})$ frequencies to the $(\omega_X, \omega_Y, \omega_Z)$ frequencies of the form:

$$\omega_{(X,Y,Z)} = A\omega_{(\zeta_1,\zeta_2,\zeta_3)}$$

where $\omega_{(X,Y,Z)} = [\omega_X, \omega_Y, \omega_Z]^T$, $\omega_{(\zeta_1,\zeta_2,\zeta_3)} = [\omega_{\zeta_1}, \omega_{\zeta_2}, \omega_{\zeta_3}]^T$, and A is the A matrix; and
   (c) after step (C), a corrected image function $\rho(\zeta'_1, \zeta'_2, \zeta'_3)$ in the $\zeta$ coordinate system is produced from the corrected image function $\rho(x',y',z')$ of step (C) using the xyz-$\zeta$ transformation.

105. The method of claim 104 further comprising displaying $\rho(\zeta'_1, \zeta'_2, \zeta'_3)$ as a corrected image.

106. The method of claim 104 further comprising producing an image function $\rho(\zeta''_1, \zeta''_2, \zeta''_3)$ having uniform pixel dimensions from $\rho(\zeta'_1, \zeta'_2, \zeta'_3)$ by performing an interpolation of the form:

$$\rho(\zeta''_1, \zeta''_2, \zeta''_3) = H(\zeta''_1, \zeta''_2, \zeta''_3, \rho(\zeta'_1, \zeta'_2, \zeta'_3))$$

where H is an interpolation function and $(\zeta''_1, \zeta''_2, \zeta''_3)$ are uniformly distributed point coordinates in the $\zeta$ coordinate system.

107. The method of claim 106 further comprising displaying $\rho(\zeta''_1, \zeta''_2, \zeta''_3)$ as a corrected image.

108. The method of claim 98 wherein:
   (a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1, \zeta_2, \zeta_3)$ and the transformation between the x,y,z and $\zeta$ coordinate systems (the "xyz-$\zeta$ transformation") being of the form:

$$r = A\zeta \text{ and } \zeta = A^{-1}r$$

where $$r = [x, y, z]^T,$$

$$\zeta = [\zeta_1, \zeta_2, \zeta_3]^T, \text{ and}$$

$$A = \begin{bmatrix} c_{11} & c_{12} & c_{13} \\ c_{21} & c_{22} & c_{23} \\ c_{31} & c_{32} & c_{33} \end{bmatrix} \text{ (the "A matrix"),}$$

where the c's are direction cosines;
   (b) in step (B), the three dimensional fast Fourier transform is performed on the MR data set in the $\zeta$ coordinate system to produce an uncorrected image function in $(\omega_{\zeta_1}, \omega_{\zeta_2}, \omega_{\zeta_3})$ frequency space, and thereafter, an uncorrected image function in $(\omega_X, \omega_Y, \omega_Z)$ frequency space is produced by a transformation of the $(\omega_{\zeta_1}, \omega_{\zeta_2}, \omega_{\zeta_3})$ frequencies to the $(\omega_X, \omega_Y, \omega_Z)$ frequencies of the form:

$$\omega_{(X,Y,Z)} = A\omega_{(\zeta_1,\zeta_2,\zeta_3)}$$

where $\omega_{(X,Y,Z)} = [\omega_X, \omega_Y, \omega_Z]^T$, $\omega_{(\zeta_1,\zeta_2,\zeta_3)} = [\omega_{\zeta_1}, \omega_{\zeta_2}, \omega_{\zeta_3}]^T$, and A is the A matrix; and
   (c) after step (C), an image function $\rho(x'',y'',z'')$ having uniform pixel dimensions is produced from $\rho(x',y',z')$ by performing an interpolation of the form:

$$\rho(x'',y'',z'') = H(x'',y'',z'',\rho(x',y',z'))$$

where H is an interpolation function and $(x'',y'',z'')$ are uniformly distributed point coordinates in the x,y,z-coordinate system; and
   (d) thereafter, a corrected image function $\rho(\zeta'_1, \zeta'_2, \zeta'_3)$ in the $\zeta$ coordinate system is produced from the image function $\rho(x'',y'',z'')$ using the xyz-$\zeta$ transformation.

109. The method of claim 108 further comprising displaying $\rho(\zeta'_1, \zeta'_2, \zeta'_3)$ as a corrected image.

110. The method of claim 93 or 94 wherein the data space of step (A) comprises:
   (a) k-space;
   (b) time space;
   (c) phase space;
   (d) frequency space;
   (e) time space along at least one coordinate direction and phase space along at least one other coordinate direction; or
   (f) time space along at least one coordinate direction and frequency space along at least one other coordinate direction.

111. The method of claim 93, 94, or 98 further comprising displaying $\rho(x',y',z')$ as a corrected image.

112. The method of claim 93, 94, or 98 further comprising producing an image function $\rho(x'',y'',z'')$ having uniform pixel dimensions from $\rho(x',y',z')$ by performing an interpolation of the form:

$$\rho(x'',y'',z'') = H(x'',y'',z'',\rho(x',y',z'))$$

where H is an interpolation function and $(x'',y'',z'')$ are uniformly distributed point coordinates in the x,y,z-coordinate system.

113. The method of claim 112 wherein the interpolation comprises Lagrange interpolation, Newton interpolation, finite differences interpolation, Hermite interpolation, spline interpolation, or combinations thereof.

114. The method of claim 112 further comprising displaying $\rho(x'',y'',z'')$ as a corrected image.

115. The method of claim 93 or 94 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$;

(b) in step (B), the three dimensional fast Fourier transform is performed on the MR data set in the $\zeta$ coordinate system to produce an uncorrected image function $\rho(\zeta_1,\zeta_2,\zeta_3)$ and thereafter, the uncorrected image function $\rho(x,y,z)$ is produced from $\rho(\zeta_1,\zeta_2,\zeta_3)$ by a transformation from the $\zeta$ coordinate system to the x,y,z-coordinate system; and (c) after step (C), a corrected image function $\rho(\zeta'_1,\zeta'_2,\zeta'_3)$ in the $\zeta$ coordinate system is produced from the corrected image function $\rho(x',y',z')$ of step (C) by a transformation from the x,y,z-coordinate system to the $\zeta$ coordinate system.

116. The method of claim 115 further comprising displaying $\rho(\zeta'_1,\zeta'_2,\zeta'_3)$ as a corrected image.

117. The method of claim 115 further comprising producing an image function $\rho(\zeta''_1,\zeta''_2,\zeta''_3)$ having uniform pixel dimensions from $\rho(\zeta'_1,\zeta'_2,\zeta'_3)$ by performing an interpolation of the form:

$$\rho(\zeta''_1,\zeta''_2,\zeta''_3) = H(\zeta''_1,\zeta''_2,\zeta''_3,\rho(\zeta'_1,\zeta'_2,\zeta'_3))$$

where H is an interpolation function and $(\zeta''_1,\zeta''_2,\zeta''_3)$ are uniformly distributed point coordinates in the $\zeta$ coordinate system.

118. The method of claim 117 further comprising displaying $\rho(\zeta''_1,\zeta''_2,\zeta''_3)$ as a corrected image.

119. The method of claim 93 or 94 wherein:

(a) in step (A), the MR data set is acquired in a Cartesian coordinate system $\zeta$ which has a common origin with the x,y,z-coordinate system but is rotated with respect to that coordinate system, the axes of the $\zeta$ coordinate system being $(\zeta_1,\zeta_2,\zeta_3)$;

(b) in step (B), the three dimensional fast Fourier transform is performed on the MR data set in the $\zeta$ coordinate system to produce an uncorrected image function $\rho(\zeta_1,\zeta_2,\zeta_3)$ and thereafter, the uncorrected image function $\rho(x,y,z)$ is produced from $\rho(\zeta_1,\zeta_2,\zeta_3)$ by a transformation from the $\zeta$ coordinate system to the x,y,z-coordinate system; and (c) after step (C), an image function $\rho(x'',y'',z'')$ having uniform pixel dimensions is produced from $\rho(x',y',z')$ by performing an interpolation of the form:

$$\rho(x'',y'',z'') = H(x'',y'',z'',\rho(x',y',z'))$$

where H is an interpolation function and $(x'',y'',z'')$ are uniformly distributed point coordinates in the x,y,z-coordinate system; and (d) thereafter, a corrected image function $\rho(\zeta'_1,\zeta'_2,\zeta'_3)$ in the $\zeta$ coordinate system is produced from the image function $\rho(x'',y'',z'')$ by a transformation from the x,y,z-coordinate system to the $\zeta$ coordinate system.

120. The method of claim 119 further comprising displaying $\rho(\zeta'_1,\zeta'_2,\zeta'_3)$ as a corrected image.

121. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients $(G_X, G_Y, G_Z)$, respectively, said method comprising:

(A) acquiring a magnetic resonance signal data set (the "MR data set") for a slice of the object in two dimensions in data space using a linear combination of the X, Y, and Z gradient magnets;

(B) producing an uncorrected image function $\rho(\zeta_1, \zeta_2)$ from the MR data set by a process which comprises performing a two dimensional fast Fourier transform on said data set, where $\zeta_1$ and $\zeta_2$ are read and phase encoding coordinates, respectively, of a $(\zeta_1,\zeta_2,\zeta_3)$ coordinate system wherein:

(i) a slice select gradient is given in the $(\zeta_1,\zeta_2,\zeta_3)$ coordinate system by:

$$G_3 = (p_{X3}G_X, p_{Y3}G_Y, p_{Z3}G_Z)$$

where $(p_{X3}, p_{Y3}, p_{Z3})$ are gradient strength coefficients of the X, Y, and Z gradient magnets $(G_X, G_Y, G_Z)$, respectively, and the axis direction of the slice gradient is:

$$\hat{\zeta}_3 = (\sin\theta_3\cos\phi_3, \sin\theta_3\sin\phi_3, \cos\theta_3)$$

where $$\theta_3 = \tan^{-1}\frac{\sqrt{(p_{X3}G_X)^2 + (p_{Y3}G_Y)^2}}{p_{Z3}G_Z}, \text{ and}$$

$$\phi_3 = \tan^{-1}\left(\frac{p_{Y3}G_Y}{p_{X3}G_X}\right);$$

(ii) a phase encoding gradient for the slice is given in the $(\zeta_1,\zeta_2,\zeta_3)$ coordinate system by:

$$G_2 = (p_{X2}G_X, p_{Y2}G_Y, p_{Z2}G_Z) \text{ such that } \hat{\zeta}_3 \cdot \hat{\zeta}_2 = 0,$$

where $(p_{X2}, p_{Y2}, p_{Z2})$ are gradient strength coefficients of the X, Y and Z gradient magnets $(G_X, G_Y, G_Z)$, respectively, and the axis direction of the phase encoding gradient is:

$$\hat{\zeta}_2 = (\sin\theta_2\cos\phi_2, \sin\theta_2\sin\phi_2, \cos\theta_2)$$

where $$\theta_2 = \tan^{-1}\frac{\sqrt{(p_{X2}G_X)^2 + (p_{Y2}G_Y)^2}}{p_{Z2}G_Z}, \text{ and}$$

$$\phi_2 = \tan^{-1}\left(\frac{p_{Y2}G_Y}{p_{X2}G_X}\right); \text{ and}$$

(iii) a read gradient for the slice is given in the $(\zeta_1,\zeta_2,\zeta_3)$ coordinate system by:

$$G_1 = (p_{X1}G_X, p_{Y1}G_Y, p_{Z1}G_Z), \text{ such that } \hat{\zeta}_3 \cdot \hat{\zeta}_1 = 0,$$

where $(p_{X1}, p_{Y1}, p_{Z1})$ are gradient strength coefficients of the X, Y and Z gradient magnets $(G_X, G_Y, G_Z)$, respectively, and the axis direction of the read gradient is:

$$\hat{\zeta}_1 = (\sin\theta_1 \cos\phi_1, \sin\theta_1 \sin\phi_1, \cos\theta_1)$$
where
$$\theta_1 = \tan^{-1} \frac{\sqrt{(p_{X1}G_X)^2 + (p_{Y1}G_Y)^2}}{p_{Z1}G_Z}, \text{ and}$$
$$\phi_1 = \tan^{-1}\left(\frac{p_{Y1}G_Y}{p_{X1}G_X}\right);$$

(C) producing a corrected image function $\rho(\zeta_1',\zeta_2')$ from the uncorrected image function $\rho(\zeta_1,\zeta_2)$, where the coordinates $(\zeta_1',\zeta_2')$ represent a corrected position in the $(\zeta_1,\zeta_2,\zeta_3)$ coordinate system for the value of the image function at $(\zeta_1,\zeta_2)$, said $(\zeta_1',\zeta_2')$ coordinates being determined using an iterative mapping which employs coefficients of expansions for the magnetic fields produced by the X, Y, and Z gradient magnets, said expansions and coefficients being for a basis set that satisfies Laplace's equation.

122. A method for forming an image of an object using a magnetic resonance imaging system which (i) comprises X, Y and Z gradient magnets and (ii) defines an origin of an (x, y, z) coordinate system (the "x,y, z-coordinatesystem"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice of the object in two dimensions in data space using a linear combination of the X, Y, and Z gradient magnets;

(B) producing an uncorrected image function $\rho(\zeta_1,\zeta_2)$ from the MR data set by a process which comprises performing a two dimensional fast Fourier transform on said data set, where $\zeta_1$ and $\zeta_2$ are read and phase encoding coordinates, respectively, of a $(\zeta_1,\zeta_2,\zeta_3)$ coordinate system wherein:

(i) a slice select gradient is given in the $(\zeta_1,\zeta_2,\zeta_3)$ coordinate system by:

$$G_3 = (p_{X3}G_X, p_{Y3}G_Y, p_{Z3}G_Z)$$

where ($P_{X3}$, $P_{Y3}$, $P_{Z3}$) are gradient strength coefficients of the X, Y, and Z gradient magnets ($G_X$, $G_Y$, $G_Z$), respectively, and the axis direction of the slice gradient is:

$$\hat{\zeta}_3 = (\sin\theta_3 \cos\phi_3, \sin\theta_3 \sin\phi_3, \cos\theta_3)$$
where
$$\theta_3 = \tan^{-1} \frac{\sqrt{(p_{X3}G_X)^2 + (p_{Y3}G_Y)^2}}{p_{Z3}G_Z}, \text{ and}$$
$$\phi_3 = \tan^{-1}\left(\frac{p_{Y3}G_Y}{p_{X3}G_X}\right);$$

(ii) a phase encoding gradient for the slice is given in the $(\zeta_1,\zeta_2,\zeta_3)$ coordinate system by:

$$G_2 = (p_{X2}G_X, p_{Y2}G_Y, P_{Z2}G_Z) \text{ such that } \hat{\zeta}_3 \cdot \hat{\zeta}_2 = 0,$$

where ($p_{X2}$, $p_{Y2}$, $p_{Z2}$) are gradient strength coefficients of the X, Y and Z gradient magnets ($G_X$, $G_Y$, $G_Z$), respectively, and the axis direction of the phase encoding gradient is:

$$\hat{\zeta}_2 = (\sin\theta_2 \cos\phi_2, \sin\theta_2 \sin\phi_2, \cos\theta_2) \text{ where}$$
$$\theta_2 = \tan^{-1} \frac{\sqrt{(p_{X2}G_X)^2 + (p_{Y2}G_Y)^2}}{p_{Z2}G_Z}, \text{ and}$$
$$\phi_2 = \tan^{-1}\left(\frac{p_{Y2}G_Y}{p_{X2}G_X}\right); \text{ and}$$

(iii) a read gradient for the slice is given in the $(\zeta_1,\zeta_2,\zeta_3)$ coordinate system by:

$$G_1 = (p_{X1}G_X, p_{Y1}G_Y, p_{Z1}G_Z), \text{ such that } \hat{\zeta}_3 \cdot \hat{\zeta}_1 = 0,$$

where ($p_{X1}$, $p_{Y1}$, $p_{Z1}$) are gradient strength coefficients of the X, Y and Z gradient magnets ($G_X$, $G_Y$, $G_Z$), respectively, and the axis direction of the read gradient is:

$$\hat{\zeta}_1 = (\sin\theta_1 \cos\phi_1, \sin\theta_1 \sin\phi_1, \cos\theta_1) \text{ where}$$
$$\theta_1 = \tan^{-1} \frac{\sqrt{(p_{X1}G_X)^2 + (p_{Y1}G_Y)^2}}{p_{Z1}G_Z}, \text{ and}$$
$$\phi_1 = \tan^{-1}\left(\frac{p_{Y1}G_Y}{p_{X1}G_X}\right);$$

(C) producing a corrected image function $\rho(\zeta_1',\zeta_2')$ from the uncorrected image function $\rho(\zeta_1,\zeta_2)$, where the coordinates $(\zeta_1',{}_2')$ represent a corrected position in the $(\zeta_1,\zeta_2,\zeta_3)$ coordinate system for the value of the image function at $(\zeta_1,\zeta_2)$, said $(\zeta_2',\zeta_2')$ coordinates being determined by solving a system of non-linear equations so that an error function $f(\zeta_1',\zeta')$ satisfies the relationship:

$$\|f(\zeta_1',\zeta')\| \leq \epsilon,$$

where $\epsilon$ is a predetermined constant;

wherein the system of non-linear equations employs coefficients of expansions for the magnetic fields produced by the X, Y, and Z gradient magnets, said expansions and coefficients being for a basis set that satisfies Laplace's equation.

123. The method of claim 122 wherein a Levenberg-Marquardt non-linear curve fitting technique is used in solving the system of non-linear equations.

124. The method of claim 122 wherein a non-linear minimization technique is used in solving the system of non-linear equations.

125. The method of claim 122 wherein:

$$\epsilon = R_{es} \times 10^{-3},$$

where $R_{es}$ is the resolution of the image given by:

$$R_{es} = A_{image}/N_{pix},$$

where $A_{image}$ is the area of the image and $N_{pix}$ is total number of pixels making up the image.

126. A method for forming an image of an object using a magnetic resonance imaging system which (i) comprises X, Y and Z gradient magnets and (ii) defines an origin of an (x, y, z) coordinate system (the "x,y,z-coordinate system"), said X, Y, and Z gradient magnets producing magnetic fields having gradients ($G_X$, $G_Y$, $G_Z$), respectively, said method comprising:

(A) acquiring a magnetic resonance signal data set (the "MR data set") for a slice of the object in two dimensions in data space using a linear combination of the X, Y, and Z gradient magnets, where the MR data set is of the form s ($m_1 \Delta t_1$, $m_2 \Delta t_2$) where:

(i) $m_1$ and $m_2$ are respectively indices for the k-space data points in $\hat{\zeta}_1$ and $\hat{\zeta}_2$ directions, where $\zeta\lambda_1$ and $\zeta_2$ are read and phase encoding coordinates, respectively, of a $(\zeta_1,\zeta_2,\zeta_3)$ coordinate system wherein:

(a) a slice select gradient is given in the $(\zeta_1,\zeta_2,\zeta_3)$ coordinate system by:

$$G_3=(p_{X3}G_X, p_{Y3}G_Y, p_{Z3}G_Z)$$

where $(p_{X3}, p_{Y3}, p_{Z3})$ are gradient strength coefficients of the X, Y, and Z gradient magnets $(G_X, G_Y, G_Z)$, respectively, and the axis direction of the slice gradient is:

$$\hat{\zeta}_3 = (\sin\theta_3\cos\phi_3, \sin\theta_3\sin\phi_3, \cos\theta_3) \text{ where}$$

$$\theta_3 = \tan^{-1}\sqrt{\frac{(p_{X3}G_X)^2 + (p_{Y3}G_Y)^2}{p_{Z3}G_Z}}, \text{ and}$$

$$\phi_3 = \tan^{-1}\left(\frac{p_{Y3}G_Y}{p_{X3}G_X}\right);$$

(b) a phase encoding gradient for the slice is given in the $(\zeta_1,\zeta_2,\zeta_3)$ coordinate system by:

$$G_2=(p_{X2}G_X, p_{Y2}G_Y, p_{Z2}G_Z) \text{ such that } \hat{\zeta}_3\cdot\hat{\zeta}_2=0,$$

where $(p_{X2}, p_{Y2}, p_{Z2})$ are gradient strength coefficients of the X, Y, and Z gradient magnets $(G_X, G_Y, G_Z)$, respectively, and the axis direction of the phase encoding gradient is:

$$\hat{\zeta}_2 = (\sin\theta_2\cos\phi_2, \sin\theta_2\sin\phi_2, \cos\theta_2) \text{ where}$$

$$\theta_2 = \tan^{-1}\sqrt{\frac{(p_{X2}G_X)^2 + (p_{Y2}G_Y)^2}{p_{Z2}G_Z}}, \text{ and}$$

$$\phi_2 = \tan^{-1}\left(\frac{p_{Y2}G_Y}{p_{X2}G_X}\right); \text{ and}$$

(c) a read gradient for the slice is given in the $(\zeta_1,\zeta_2,\zeta_3)$ coordinate system by:

$$G_1=(p_{X1}G_X, p_{Y1}G_Y, p_{Z1}G_Z), \text{ such that } \hat{\zeta}_3\cdot\hat{\zeta}_1=0,$$

where $(P_{X1}, P_{Y1}, p_{Z1})$ are gradient strength coefficients of the X, Y and Z gradient magnets $(G_X, G_Y, G_Z)$, respectively, and the axis direction of the read gradient is:

$$\hat{\zeta}_1 = (\sin\theta_1\cos\phi_1, \sin\theta_1\sin\phi_1, \cos\theta_1) \text{ where}$$

$$\theta_1 = \tan^{-1}\sqrt{\frac{(p_{X1}G_X)^2 + (p_{Y1}G_Y)^2}{p_{Z1}G_Z}}, \text{ and}$$

$$\phi_1 = \tan^{-1}\left(\frac{p_{Y1}G_Y}{p_{X1}G_X}\right);$$

(ii) $\Delta t_1$ and $\Delta t_2$ are respectively equivalent time steps in k-space for the $\hat{\zeta}_1$ and $\hat{\zeta}_2$ directions;

(B) producing an uncorrected image function $\rho(l_1\Delta\omega_1^L, l_2\Delta\omega_2^L)$ from the MR data set by a process which comprises performing a two dimensional fast Fourier transform on said data set, said uncorrected image function being in frequency space at a set of frequency points given by $(l_1\Delta\omega_1^L, l_2\Delta\omega_2^L)$ where:

(i) $l_1$ and $l_2$ are indices for the frequency points in the $\omega_1^L$ and $\omega_2^L$ directions, respectively;

(ii) $\Delta\omega_1^L$ and $\Delta\omega_2^L$ are frequency steps in the $\omega_1^L$ and $\omega_2^L$ directions, respectively;

(iii) $\omega_1^L=\gamma G_1^L\cdot\hat{\zeta}_1$, $\omega_2^L=\gamma G_2^L\cdot\hat{\zeta}_2$, where:
(a) $\gamma$ is a constant; and (b) $(G_1^L, G_2^L)$ represent the linear parts of the gradients $(G_1, G_2)$ of the magnetic fields produced by the X, Y, and Z gradient magnets;

(iv) the range of $l_1$ is selected so that $l_1\cdot\Delta\omega_1^L$ spans the frequency range that would arise from the $G_1$ gradient if that gradient were purely linear in the $\hat{\zeta}_1$ direction and the range of $l_1$ is selected so that $l_1\cdot\Delta\omega_1^L$ spans the frequency range that would arise from the $G_2$ gradient if that gradient were purely linear field in the $\hat{\zeta}_2$ direction; and (v) the fast Fourier transform is of the form:

$$\rho(l_1\Delta\omega_1^L, l_2\Delta\omega_2^L) = \sum_{m_2}\sum_{m_1} s(m_1\Delta t_1, m_2\Delta t_2)$$
$$e^{i(l_1\Delta\omega_1^L\cdot m_1\Delta t_1 + l_2\Delta\omega_2^L\cdot m_2\Delta t_2)}\Delta t_1\Delta t_2$$

(C) producing a corrected image function $\rho(\zeta_1',\zeta_2')$ in frequency space at $(\zeta_1', \zeta_2', \zeta_3')$ in the $(\zeta_1,\zeta_2,\zeta_3)$ coordinate system from the uncorrected image function $\rho(l_1\Delta\omega_1^L, l_2\Delta\omega_2^L)$ using an interpolation function L in frequency space of the form:

$$\rho(\omega_1^N(\zeta_1',\zeta_2',\zeta_3'), \omega_2^N(\zeta_1',\zeta_2',\zeta_3'))=L(\omega_1^N,\omega_2^N,\rho(l_1\Delta\omega_1^L,l_2\Delta\omega_2^L))$$

where:

(i) $\rho(\omega_1^N(\zeta_1',\zeta_2',\zeta_3'),\omega_2^N(\zeta_1',\zeta_2',\zeta_3'))$ is the desired $\rho(\zeta_1', \zeta_2')$; and (ii) $G_1^L$, $G_2^L$, $\omega_1^N(\zeta_1',\zeta_2',\zeta_3')$, and $\omega_2^N(\zeta_1',\zeta_2',\zeta_3')$ are determined using coefficients of expansions for the magnetic fields produced by the X, Y, and Z gradient magnets, said expansions and coefficients being for a basis set that satisfies Laplace's equation.

127. The method of claim 126 wherein the interpolation function L is a sinc function such that:

$$L(\omega_1^N, \omega_2^N, \rho(l_1\Delta\omega_1^L, l_2\Delta\omega_2^L)) = \sum_{l_2}\sum_{l_1}\rho(l_1\Delta\omega_1^L, l_2\Delta\omega_2^L)$$
$$\text{sinc}\left(\frac{\omega_1^N}{\Delta\omega_1^L} - l_1, \frac{\omega_2^N}{\Delta\omega_2^L} - l_2\right).$$

128. The method of claim 126 wherein the interpolation function L is of the form:

$$L(\omega_1^N, \omega_2^N, \rho(l_1\Delta\omega_1^L, l_2\Delta\omega_2^L)) = \sum_{l_2}\sum_{l_1} C_{(l_1,l_2)}\psi_{1(l_1)}(\omega_1^N)\psi_{2(l_2)}(\omega_2^N)$$

where:

(a) $\psi_{1(l_1)}$ and $\psi_{2(l_2)}$ are orthogonal bases functions; and (b) the $C_{(l_1,l_2)}$ are coefficients which satisfy the matrix equation:

$$AC=\rho$$

where the vector C is of the form:

$$C=[C_{(1,1)}\ C_{(2,1)}\ \ldots\ C_{(l_1,l_2)}]^T$$

the vector $\rho$ is of the form:

$$\rho[\rho(\omega_{1(1)}^L,\omega_{2(1)}^L)\ \rho(\omega_{1(2)}^L,\omega_{2(1)}^L)\ \ldots\ \rho(\omega_{1(l_1)}^L,\omega_{2(l_2)}^L)]^T$$

and the matrix A is of the form:

$$\begin{bmatrix} \psi_{1(1)}(\omega_{1(1)}^L)\psi_{2(1)}(\omega_{2(1)}^L) & \psi_{1(2)}(\omega_{1(1)}^L)\psi_{2(1)}(\omega_{2(1)}^L) & \cdots & \psi_{1(l_1)}(\omega_{1(1)}^L)\psi_{2(l_2)}(\omega_{2(1)}^L) \\ \psi_{1(1)}(\omega_{1(2)}^L)\psi_{2(1)}(\omega_{2(1)}^L) & \psi_{1(2)}(\omega_{1(2)}^L)\psi_{2(1)}(\omega_{2(1)}^L) & \cdots & \psi_{1(l_1)}(\omega_{1(2)}^L)\psi_{2(l_2)}(\omega_{2(1)}^L) \\ \vdots & \vdots & \ddots & \vdots \\ \psi_{1(1)}(\omega_{1(l_1)}^L)\psi_{2(1)}(\omega_{2(l_2)}^L) & \psi_{1(2)}(\omega_{1(l_1)}^L)_2\psi_{2(1)}(\omega_{2(l_2)}^L) & \cdots & \psi_{1(l_1)}(\omega_{1(l_1)}^L)\psi_{2(l_2)}(\omega_{2(l_2)}^L) \end{bmatrix}.$$

129. The method of claim 128 wherein the interpolation comprises Lagrange's interpolation, Newton interpolation, finite difference interpolation, Hermite interpolation, spline interpolation, or combinations thereof.

130. The method of claim 128 wherein the interpolation is applied to all of the data points obtained by performing the two dimensional fast Fourier transform on the MR data set.

131. The method of claim 128 wherein the interpolation is applied to a subset of the data points obtained by performing the two dimensional fast Fourier transform on the MR data set, said subset being in the vicinity of a region of interest of the object being imaged.

132. The method of claim 121, 122, or 126 further comprising displaying $\rho(\zeta_1',\zeta_2')$ as a corrected image.

133. The method of claim 121, 122, or 126 further comprising producing an image function $\rho(\zeta_1'',\zeta_2'')$ having uniform pixel dimensions from $\rho(\zeta_1',\zeta_2'')$ by performing an interpolation of the form:

$$\rho(\zeta_1'',\zeta_2'')=H(\zeta_1'',\zeta_2'',\rho(\zeta_1',\zeta_2'))$$

where H is an interpolation function and $(\zeta_1'',\zeta_2'')$ are uniformly distributed point coordinates in the $(\zeta_1,\zeta_2,\zeta_3)$ coordinate system.

134. The method of claim 133 wherein the interpolation comprises Lagrange interpolation, Newton interpolation, finite differences interpolation, Hermite interpolation, spline interpolation, or combinations thereof.

135. The method of claim 133 further comprising displaying $\rho(\zeta_1'',\zeta_2'')$ as a corrected image.

\* \* \* \* \*